US006084069A

United States Patent [19]
Stracke et al.

[11] Patent Number: 6,084,069
[45] Date of Patent: *Jul. 4, 2000

[54] AUTOTAXIN: MOTILITY STIMULATING PROTEIN USEFUL IN CANCER DIAGNOSIS AND THERAPY

[75] Inventors: Mary Stracke, Rockville; Lance Liotta, Potomac; Elliott Schiffmann, Chevy Chase; Henry Krutzch, Bethesda, all of Md.; Jun Murata, Toyama, Japan

[73] Assignee: The United States of America as represented by the Department of Health and Human Services, Washington, D.C.

[*] Notice: This patent is subject to a terminal disclaimer.

[21] Appl. No.: 08/977,221

[22] Filed: Nov. 24, 1997

Related U.S. Application Data

[60] Division of application No. 08/346,455, Nov. 28, 1994, Pat. No. 5,731,167, which is a continuation-in-part of application No. 08/249,182, May 25, 1994, abandoned, which is a continuation-in-part of application No. 07/822,043, Jan. 17, 1992, Pat. No. 5,449,753.

[51] Int. Cl.$^7$ ................................................. C07K 17/00
[52] U.S. Cl. .......................... 530/350; 530/326; 530/324; 530/330; 530/412; 435/69.1; 435/7.92
[58] Field of Search .................................. 530/330, 326, 530/324, 350, 412; 435/69.1, 7.92

[56] References Cited

U.S. PATENT DOCUMENTS

| 5,003,047 | 3/1991 | Yarmush et al. | 530/413 |
| 5,449,753 | 9/1995 | Stracke et al. | 530/326 |

FOREIGN PATENT DOCUMENTS

WO 93/14202   7/1993   WIPO .

OTHER PUBLICATIONS

Henderson et al. (1993) EMBL Database, Accession No. S06727, 1993.
Lawrence et al. (1990) J. Virol. 64:287–299, 1990.
Lawrence et al. (1996) GenBank Database, Accession No. Q69545, 1996.
Zierer et al. (1997) GenBank Database, Accession No. S12888, 1997.
Zierer et al. (1990) FEBS 273:59–62, 1990.
Stainthorpe et al. (1992) GenBank Database, Accession No. JQ0700, 1992.
Stainthorpe et al. (1990) Gene 91:27–34, 1990.
Knight et al. (1990) GenBank Database, Reference No. TN024561, 1990.
Knight et al. (1990) J. Molec. Biol. 215:113–160, 1990.
Buckley et al. (1991) GenBank Database, Accession No. A39216, 1991.
Buckley et al. (1990) J. Biol. Chem. 265:17506–17511, 1990.
Oda et al. (1992) GenBank Database, Accession No. A41179, 1992.
Oda et al. (1991) J. Biol. Chem. 266:16791–16795, 1991.
Culp et al. (1988) GenBank Accession No. A25274, 1988.
Culp et al. (1985) J. Biol. Chem. 260:8320–8324, 1985.
Henderson et al. (1989) Molec. Microbiol. 3/10:1307–1318, 1989.
M. L. Stracke, et al., "Identification, Purification, and Partial Sequence Analysis of Autotaxin, a Novel Motility–stimulating Protein", *The Journal of Biological Chemistry*, vol. 267, Feb. 5, 1992, No. 4, 1992, pp. 2524–2529.
H. Watanabe, et al. "Purification of Human Tumor Cell Autocrine Motility Factor and Molecular Cloning of Its Receptor," *The Journal of Biological Chemistry*, vol. 20, Jul. 15, 1991, pp. 13442–13448.
S. Silletti, et al. "Purification of B16–F1 Melanoma Autocrine Motility Factor and Its Receptor," *Cancer Research*, Jul. 1, 1991, pp. 3507–3511.
T. Ohnishi, et al. "Motility Factor Produced By Malignant Glioma Cells: Role in Tumor Invasion," *J. Neurosurg.*, vol. 73, Dec. 1990, pp. 881–888.
K. Michael Weidner, et al., "Scatter Factor: Molecular Characteristics and Effect on the Invasiveness of Epithelial Cells," *The Journal of Cellular Biology*, vol. 111, Nov. 1990, pp. 2097–2108.
E. M. Rosen, et al. "Purified Scatter Factor Stimulates Epithelial and Vascular Endothelial Cell Migration," *Society for Experimental Biology and Medicine*, Copyright 1990, pp. 34–43.
E. Gherardi, et al., "Purification of Scatter Factor, a Fibroblast–Derived Basic Protein That Modulates Epithelial Interactions and Movement," *Proc. Natl. Acad. Sci.*, vol. 86, Aug. 1989, pp. 5844–5848.
M. L. Stracke, et al., "The Type Insulin–Like Growth Factor Receptor Is A Motility Receptor in Human Melanoma Cells," *The Journal of Biological Chemistry*, vol. 264, Dec. 25, 1989, pp. 21544–21549.
S.L. Schor, et al., "Foetal and Cancer Patient Fibroblasts Produce an Autocrine Migration–Stimulating Factor Not Made by Normal Adult Cells," *Journal of Cell Science*, 1988, pp. 391–399.
K. D. Atnip, et al. "Chemotactic Response of Rat Mammary Adenocarcinoma Cell Clones to Tumor–Derived Cytokines," *Biochemical and Biophysical Research Communications*, vol. 146, Aug. 14, 1987, pp. 996–1002.
L. A. Liotta, et al. "Tumor Cell Autocrine Motility Factor," *Proc. Natl. Acad, Sci.*, vol. 83, May 1986, pp. 3302–3306.
S.J. Singer, et al. "The Directed Migration of Eukaryotic Cells," *Ann. Rev, Cell Biol.*, pp. 337–362. (1986).

(List continued on next page.)

*Primary Examiner*—Rebecca E. Prouty
*Assistant Examiner*—Enrique D. Longton
*Attorney, Agent, or Firm*—Morgan & Finnegan, L.L.P.

[57] ABSTRACT

The present invention relates, in general, to autotaxin. In particular, the present invention relates to a DNA segment encoding autotaxin; recombinant DNA molecules containing the DNA segment; cells containing the recombinant DNA molecule; a method of producing autotaxin; antibodies to autotaxin; and identification of functional domains in autotaxin.

5 Claims, 16 Drawing Sheets

OTHER PUBLICATIONS

I.R. Nabi, et al. "Identification of B16–F1 Melanoma Autocrine Motility–Like Factor Receptor," *Cancer Research*, Jan. 15, 1990, pp. 409–414.

G. J. Todaro, et al. Transforming Growth Factors produced by Certain Human Tumor Cells: Polypeptides That Interact With Epidermal Growth Factor Receptors, *Proc. Natl. Acad., Sci.*, vol. 77, No. 9, Sep. 1990, pp. 5258–5262.

J. Murata, et al., "cDNA Cloning of the Human Tumor Motility–stimulating Protein, Autotaxin, Reveals a Homology with Phosphodiesterases", *The Journal of Biological Chemistry*, vol. 269, No. 48, Dec. 2, 1994 pp. 30479–30484.

M. Narita, et al., "Molecular Cloning, Expression, and Localization of a Brain–Specific Phosphodiesterase I/Nucleotide Pyrophoasphatase (PD–Iα) From Rat Brain," *The Journal of Biological Chemistry*, 1994, pp. 28235–28242.

R. M. Warn, et al, "Motility Factors on the March," *Nature*, vol. 340, Jul. 20, 1989, pp. 186–187.

M. Stoker, et al. "Scatter Factor is a Fibroblast–Derive Modulator of Epithelial Cell Motility," *Nature*, vol. 327, May 1987, pp. 239–242.

B. Alberts, et al. "Molecular Biology of the Cell," Garland Publishing, Inc. (1983).

K. Yoshida, et al. "Studies On The Mechanisms of Invasion in Cancer. I. Isolation and Purification of a Factor Chemotactic For Cancer Cells," *Int. J. Cancer*, 1970, pp. 123–132.

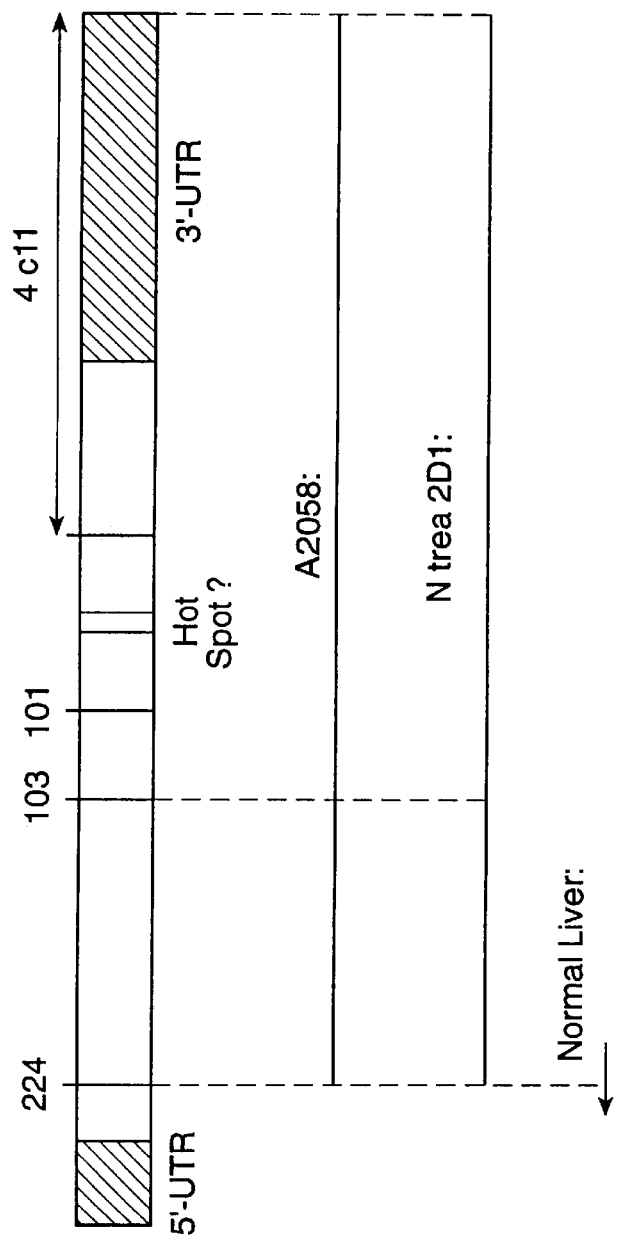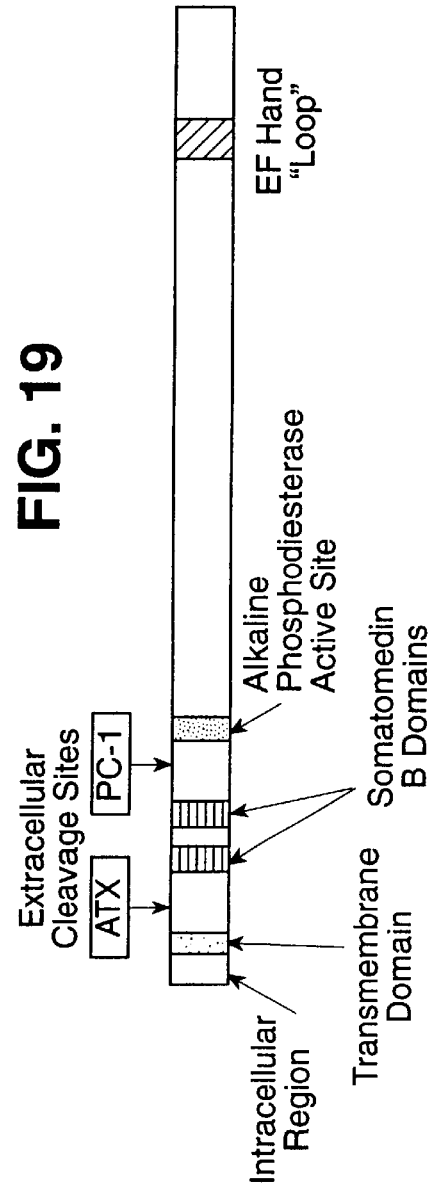

← 125 kDa

FIG. 18A

```
hATX    MARRSFQSCQIISLFTFAVGVSICLGFTAHRIKRAEGWEEGPPTVLSDSPWTNISGGSCKGRCFELQEAGPPDCRCDNLCKSYTSCCHDF    90
                                                          ||||       |||| ||||  |  ||  ||||  |
hPC1    MDVGEEPLEKAARARTAKDPNTYKVLSLVLSVCVLTTIL........GCIFG....LKPSCAKEVK.SCKGRCF...ERTFGNCRCDAACVELGHCCLDY    84 hATX    DELCLKTARGWECTKDRCGEVRNEENACHCSEDCLARGDCCTNYQVVCKGESHWVDDDCEEIKAAECPAGFVRPPLIIFSVDGFRASYMKKGSKVMPNIE    190
         ||||||| || |||| |||||||||||| | |||   |||||||||||||||||||| |||||||| ||| ||| ||||||||||||  ||||| ||
hPC1    QETCIEPEHIWTCNKFRCGEKRLTRSLCACSDDCKDKGDCCINYSSVQQGEKSWVEEPCESINEPQCPAGFETPTLLFSLDGFRAEYLHTWGGLLPVIS    184 hATX    KLRSCGTHSPYMRPVYPTKTFPNLYTLATGLYPESHGIVGNSMYDPVFDATFHLRGREKFNHRWWGGQPLWITATKQGVKAGTFFWS............    272
        || ||||  ||| ||||||||||  ||||||||||||  || ||||||| |||| |||||  |||| || |||| |||||||
hPC1    KLKKCGTYTKNMRPVYPTKTFPNHYSIVTGLYPESHGIIDNKMYDPKMNASFSLKSKEKFNPEWYKGEPIWTAKYQGLKSGTFFWPGSDVEINGIFPDI    284 hATX    ......VVIPHERRILTILRWLTLPDHERPSVYAFYSEQPDFSGHKYGPFGPESSYGSPFTPAKRPKRKVAPKRRQERPVAPPKKRRRKIHRMDHYAAET    372
              |||||||| ||||| ||||||  |||| |||||||||||| ||||||||||||||||||||
hPC1    YKMYNGSVPFEERILAVLQWLQLPKDERPHFYTLYLEEPDSSGHSYGPVSSE.............................................    336 hATX    RQDKMTNPLREIDKIVGQLMDGLKQLMDGLKELNLHRCLNLILTSDHGMEQGSCKKYIYLNKYLGDVKNIKVIYGPAARLRPSDVPDKYYSPNYEGIARNLSCREPN    470
                                        |||  | |||  ||           || |  | ||   |||      |||   | |      ||
hPC1    ......VIKALQRVDGMVGMLMDGLKELNLHRCLNLILTSDHGMEQGSCKKYIYLNKYLGDVKNIKVIYGPAARLRPSDVPDKYYSPNYEGIARNLSCREPN    432 hATX    QHFKPYLKQHLPKRLHYANNRRIEDIHLLVERRWHVARKPLDVKKPSGKCFFQGDHGFDNKVNSMQTVPVGYGPTFKYKTKVPPFENIELYNVMCDLIG    570
        |||||||| |||||||  |||   |  |  |  |  |||||||| |        |         ||  |    ||||||   ||||| |||||| |
hPC1    QHFKPYLKHGLPKRLHFAKSDRIEPLTFYLDPQWQLALNPSE..RKYCGSGF........HGSDNVFSNMQALFVGYGPGFKHGIEADTFENIEVYNLMCDLLN    526
```

FIG. 18B

```
hATX  LKPAPNNGTHGSLNHLLRTNTFRPTMPEEVTRPNYPGIMYLQSDFDLGCTCDDKVEPKNKLD.ELNKRLHTKGSTEERHLLYGRPAVLYRTR.YDILYHT  668
       ||||||||||||| ||||  ||     |       |||||   |              |    ||   |   |||    ||     |    |||  |
hPC1  LTPAPNNGTHGSLNHLLKNPVYTPKHPKEV.HPLVQCPFTRNPRDNLGCSNPSILPIEDFQTQFNLTVAEEKIIKHETLPYGRPRVLQKENTICLLSQH  625 hATX  DFESGYSEIFLMLLWTSYTVSKQAEVSSVPDHLTSCVRPDVRVSPSFSQNCLAYKNDKQMSYGFLFPPYLSSSPEAKY.DAFLVTNMVPMYPAFKRVWNY  767
       ||||||||| || |||||||||       |    || |     |||| ||    |  |||||| |||||  ||||  ||| | ||||||  || ||
hPC1  QFMSGYSQDILMPLWTSYTVDRNDSFS..TEDFSNCLYQDFRIPLSPVHKCSFYKNTKVSYGFLSPPQLNKNSSGIYSEALLTNIVPMYQSFQVIWRY   723 hATX  FQRVLVKKYASERNGVNNISGPIFDYDYDGLHDTEDKIKQ...YVEGSSIPVPTHYSIITSCLDFTQPADKCDGPLSVSSFILPHRPDNEESCNSSEDE  875
        | |  ||| ||||||| ||||| |||||                    | || |      ||    | | |     ||||| |    ||
hPC1  FHDTLLRKYAEERNGVNVVSGPVFDFDYDGRCDSLENLRQKRRVIRNQEILPTHFFIVLTSCKDTSQTPLHCEN.LDTLAFILPHRTDNSESCVHGKHD  822 hATX  SKWVEELMKMHTARVRDIEHLTSLDFFRKTSRSYPEILLTKTYLHTYESEI  915
       |||||||| || |   ||||| |||||
hPC1  SSWVEELLMLHRARITDVEHITGLSFYQQRKEPVSDILKLKTHLPTFSQED  873
```

AUTOTAXIN: MOTILITY STIMULATING PROTEIN USEFUL IN CANCER DIAGNOSIS AND THERAPY

This is a divisional of application Ser. No. 08/346,455 now U.S. Pat. No. 5,731,167 filed Nov. 28, 1994, which is a continuation-in-part of Ser. No. 08/249,182 abandoned filed May 25, 1994, which is a continuation-in-part of application Ser. No. 07/822,043, now U.S. Pat. No. 5,449,753 filed on Jan. 17, 1992.

This application is a continuation-in-part of application Ser. No. 08/249,182 filed May 25, 1994, which is a continuation-in-part of application Ser. No. 07/822,043 filed on Jan. 17, 1992.

FIELD OF THE INVENTION

The present invention relates, in general, to a motility stimulating and compositions comprising the same. In particular, the present invention relates to a purified form of the protein and peptides thereof, for example, autotaxin (herein alternative referred to as "ATX"); a DNA segment encoding autotaxin; recombinant DNA molecules containing the DNA segment; cells containing the recombinant DNA molecule: a method of producing autotaxin; antibodies to autotaxin; and methods of cancer diagnosis and therapy using the above referenced protein or peptides thereof and DNA segments.

BACKGROUND OF THE INVENTION

Cell motility plays an important role in embryonic events, adult tissue remodeling, wound healing, angiogenesis, immune defense, and metastasis of tumor cells (Singer, 1986). In normal physiologic processes, motility is tightly regulated. On the other hand, tumor cell motility may be aberrantly regulated or autoregulated. Tumor cells can respond in a motile fashion to a variety of agents. These include host-derived factors such as scatter factor (Rosen, et al., 1989) and growth factors (Kahan, et al., 1987; Stracke, et al.; Tamm, et al., 1989; Wang, et al. 1990; and Jouanneau, et al. 1991), components of the extracellular matrix (McCarthy, et al. 1984), and tumor-secreted or autocrine factors (Liotta, et al. 1988; Ruff, et al. 1985; Atnip, et al. 1987; Ohnishi, et al. 1990; Silletti, et al. 1991; and Watanabe, et al. 1991).

Many types of host-derived soluble factors act in a paracrine fashion to stimulate cell locomotion. Motility-stimulating proteins called "scatter factors" have been identified which are produced by embryonic fibroblasts and by smooth muscle cells (Stoker, et al. 1987). Scatter factors stimulate random and directed motility by epithelial cells, keratinocytes, vascular endothelial cells and carcinoma cells (Stoker, et al. 1987; Rosen, et al. 1990; and Weidner, et al. 1990), but not fibroblasts. In addition, a number of host-secreted growth factors have been demonstrated to stimulate motility in tumor cells, including nerve growth factor (Kahan, et al. 1987) insulin-like growth factor-I (Stracke, et al. 1988), interleukin-6 (Tamm, et al. 1989), interleukin-8 (Wang, et al. 1990), and acidic fibroblast growth factor (Jouanneau, et al. 1991). These paracrine factors may influence "homing" or the directionality of tumor cell motility.

In contrast to these host-derived factors, many types of tumor cells have been found to produce proteins termed "autocrine motility factors" which stimulate motility by the same tumor cells which make the factor (Liotta, et al. 1986). Autocrine motility factors are not specific for a given type of cancer cell but have a wide spectrum of activity on many types of cancer cells (Kohn, et al. 1990), with little effect on normal fibroblasts or leukocytes.

Autocrine motility factors identified to date act through cell-surface receptors (Stracke, et al. 1987; Nabi, et al. 1990; Watanabe, et al. 1991) resulting in pseudopodial protrusion (Guirguis, et al. 1987) leading to both random and directed migration (Liotta, et al. 1986; Atnip, et al. 1987; Ohnishi, et al. 1990).

Prior studies of human A2058 melanoma cells have demonstrated that these cells are a particularly rich source of autocrine motility factors. An autocrine motility factor with a molecular mass of approximately 60 kDa has been previously isolated from the conditioned media of these cells. (Liotta, et al. 1986). Similar tumor cells derived or induced factors with the same molecular weight have subsequently been reported and purified by several investigators (Atnip, et al. 1987; Schnor, et al. 1988; Ohnishi, et al. 1990; Silletti, et al. 1991; Watanabe et al. 1990). Such factors are thought to play a key role in tumor cell invasion.

Most of the motility factors identified to date have not been purified to homogeneity and have not been sequenced. The novel tumor motility factor of the present invention, named herein as autotaxin ("ATX"), has been purified and verified to be a homogeneous sample by two-dimensional gel electrophoresis. The protein of the present invention is unique from any previously identified or purified motility factor. The molecular size of ATX is about 125 kilo Daltons ("kDa") and it has an isoelectric point of approximately 7.7. ATX stimulates both random and directed migration of human A2058 melanoma cells at picomolar concentrations. The activity of the ATX factor is completely sensitive to inhibition by pertussis toxin. No significant homology has been found to exist between the protein of the invention and any mammalian protein including previous factors known to stimulate cell motility.

There is a great clinical need to predict the aggressiveness of a patient's individual tumor, to predict the local recurrence of treated tumors and to identify patients at high risk for development of invasive tumors. The present invention provides a functional marker which is functionally related to the invasive potential of human cancer. The invention further provides an assay for this secreted marker in body fluids, or in tissues. The assay of the invention can be used in the detection, diagnosis, and treatment of human malignancies and other inflammatory, fibrotic, infectious or healing disorders.

SUMMARY OF THE INVENTION

The present invention relates, generally, to a motility stimulating protein and corresponding peptides thereof, and to a DNA segment encoding same. A human cDNA clone encoding a tumor cell motility-stimulating protein, herein referred to as autotaxin or "ATX", reveals that this protein is an ecto/exoenzyme with significant homology to the plasma cell membrane differentiation antigen PC-1. ATX is a 125 kDa glycoprotein, previously isolated from a human melanoma cell line (A2058), which elicits chemotactic and chemokinetic responses at picomolar to nanomolar concentrations.

It is a specific object of the present invention to provide autotaxin and peptide fragments thereof.

It is a further object of the present invention to provide a DNA segment that encodes autotaxin and a recombinant DNA molecule comprising same. It is a further object of the present invention to provide a cell that contains such a recombinant molecule and a method of producing autotaxin using that cell.

Another object of the present invention is the identification of a transmembrane domain of the human liver autotaxin protein and its apparent absence in tumorous forms of autotaxin. The tumorous form of autotaxin appears to be a secreted protein. The present invention relates to utilization of the different sites of localization for diagnosis and prognosis of the stages of tumor progression. Further, the invention relates to treatment methods, designed to advantageously block the secreted form of autotaxin activity while having little effect on the membrane-bound form of autotaxin.

Yet another object of the present invention relates to the identification of a highly variable region within the autotaxin gene, called a "hot spot". The variations in sequence apparently result in mutations, insertions, deletions and premature termination of translation. The present invention relates to manipulating this region so as to alter the activity of the protein. Further, the hot spot can serve as a marker in tumor diagnosis differentiating between different forms of the autotaxin protein.

It is yet another object of the present invention to provide a method of purifying autotaxin.

It is a further object of the present invention to provide cloned DNA segments encoding autotaxin and fragments thereof. The cDNA encoding the entire autotaxin protein contains 3251 base pairs, and has an mRNA size of approximately 3.3 kb. The full-length deduced amino acid sequence of autotaxin comprises a protein of 915 amino acids. Database analysis of the ATX sequence revealed a 45% amino acid identity (including 30 out of 33 cysteines) with PC-1, a pyrophosphatase/type I phosphodiesterase expressed on the surface of activated B cells and plasma cells. ATX, like PC-1, was found to hydrolyze the type I phosphodiesterase substrate p-nitrophenyl thymidine-5'monophosphate. Autotaxin now defines a novel motility-regulating function for this class of ecto/exo-enzymes.

Further objects and advantages of the present invention will be clear from the description that follows.

BRIEF DESCRIPTION OF THE DRAWINGS

FIG. 13. Schematic Diagram of autotaxin gene region.

For A2058: 4C11 is the original DNA clone obtained by screening an A2058 cDNA expression library in λgt11 with anti-peptide ATX-102. Upstream ATX peptide sequences were utilized for PCR amplification of A2058 mRNA, using the technique of reverse transcription/PRC. These peptides include ATX-101, ATX-103, and ATX-224. The approximate localization of each of peptide was obtained by matching the peptide with its homologous region on PC-1.

For N-tera 2D1, a λgt10 cDNA library was amplified and the cDNA inserts were isolated. PCR amplification, based on homologies with A2058 sequence, was utilized for DNA sequencing.

For normal human liver, a mRNA from liver was amplified with 5'RACE using primers from the known ATX-224 region of A2058 and N-tera 2D1.

Figure 14:
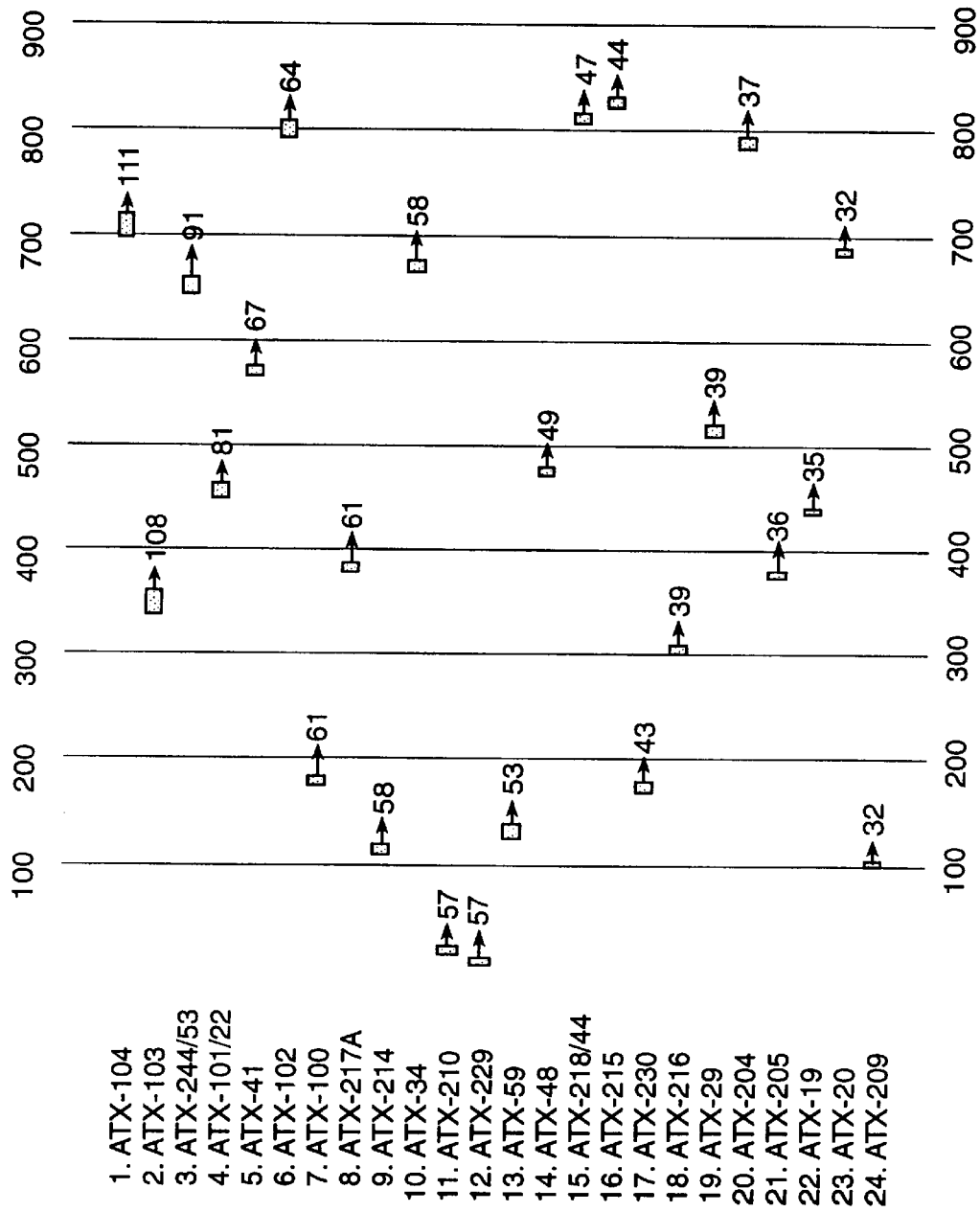

FIG. 14. Schematic match-up of ATX peptides with putative A2058 protein sequence.

Figure 15:
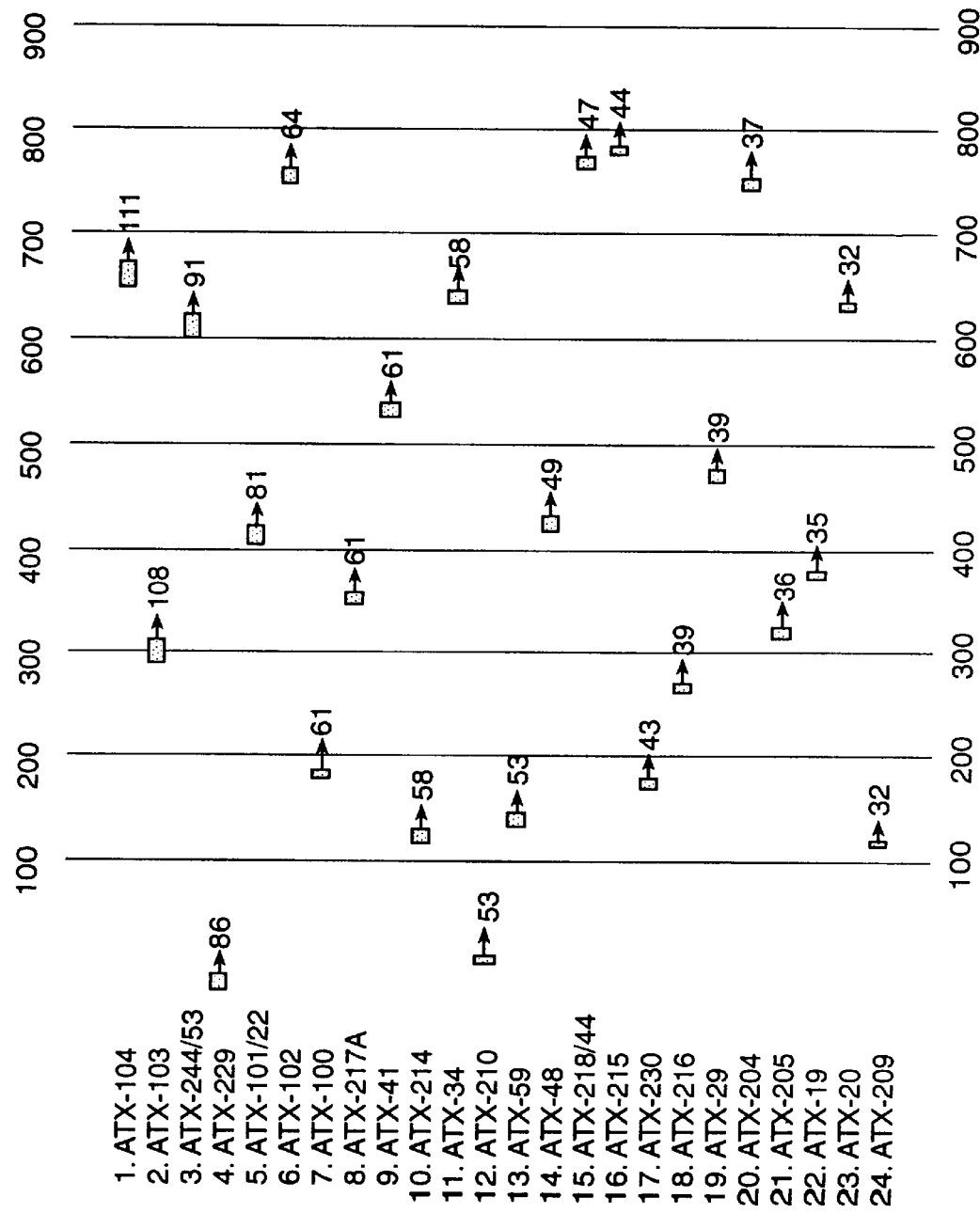

FIG. 15. Schematic match-up of ATX peptides with putative N-tera 2D1 protein sequence.

Figure 16:
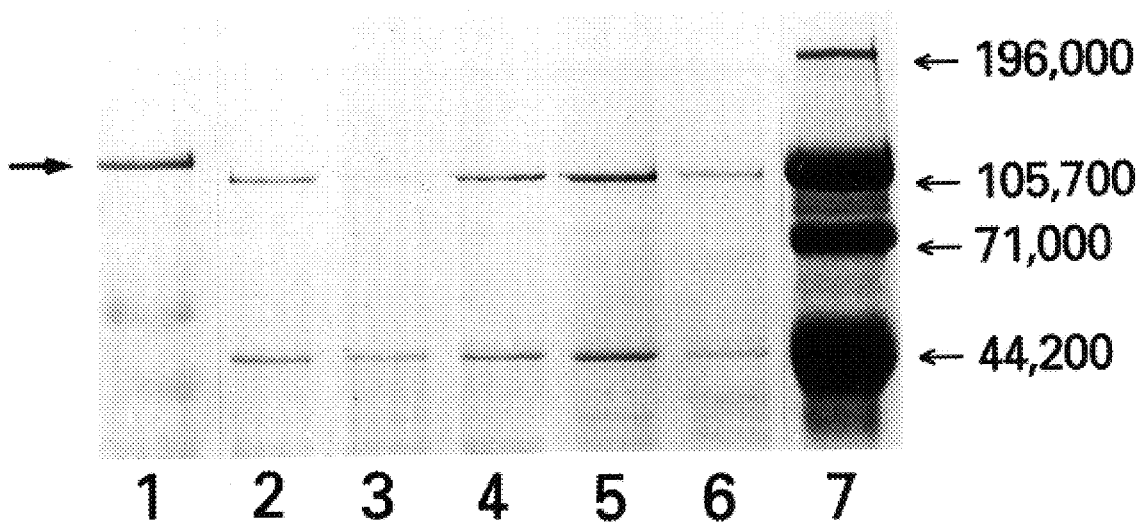

FIG. 16: ATX Treatment with PGNase F. Partially purified ATX was treated with 60 mU/ml PNGase F at 37° C. for 16 hr under increasingly denaturing conditions. The treated ATX samples were separated by SDS polyacrylamide gel electrophoresis run under reducing conditions and stained with Coomassie blue G-250. Lane 1 contains untreated ATX (arrow) with no enzyme added. Lane 2 contains the reaction mixture run under non-denaturing conditions (50 mM tris/10% ethylene glycol, pH 7). Lanes 3 and 4 have added 0.1M β-mercaptoethanol and 0.5% Nonidet-P40, respectively. Lanes 5 and 6 contain the reaction mixtures in which the ATX sample was first boiled for 3 min in 0.1% SDS with (lane 6) or without (lane 5) 0.1M β-mercaptoethanol, then had 0.5% Nonidet-P40 added to prevent enzyme denaturation. The enzyme can be detected as an ~44 kDa band in lanes 2–6.

Figure 17A:
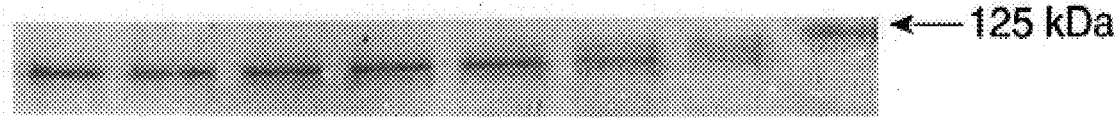
Figure 17B:
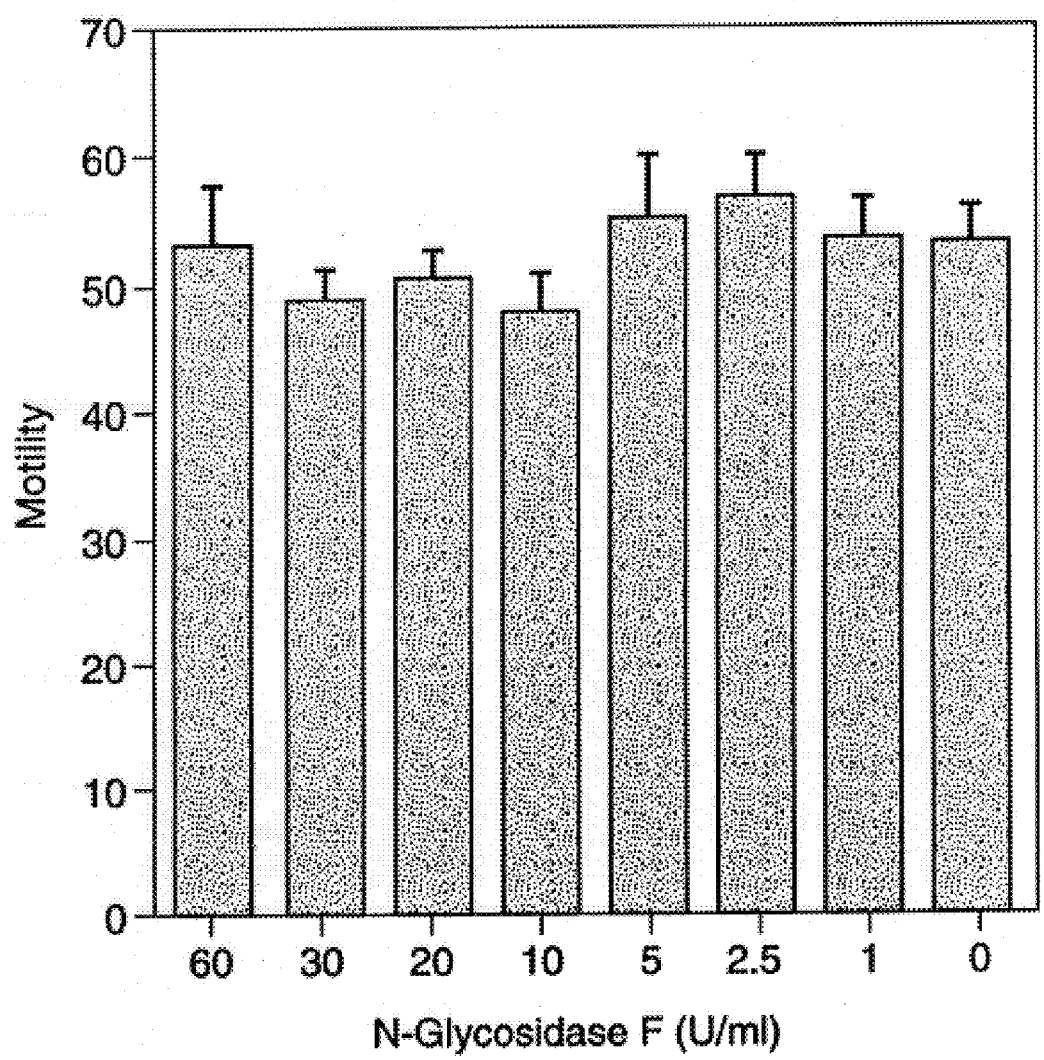

FIG. 17: Effect of varying concentrations of PNGase F on ATX molecular weight and motility-stimulating activity. Partially purified ATX was treated with various concentrations (range 0–60 mU/ml, shown on horizontal axis) of PNGase F at 37° C. for 16 hr. FIG. 17A shows the effect of the different treatments on ATX molecular weight. At concentrations of enzyme ≧30 mU/ml, the deglycosylation reaction appears to be complete. FIG. 17B shows the effect of the identical reaction mixtures on motility-stimulating capacity (immediately below the corresponding protein band of FIG. 17A). There is no significant difference between any of the treatment groups.

FIG. 18: Comparison of amino acid sequences of ATX (SEQ ID NO:69) and PC-1. The amino acid sequences of ATX and PC-1 (Buckley, et al., 1990) are compared. Amino acid identity is indicated by a vertical line between the sequences. The location of the putative transmembrane/signal sequence is shown by a solid line. The two somatomedin B domains are identified by dashed lines. The putative phosphodiesterase active site is indicated by emboldened lines. The loop region of a single EF hand loop region is identified with double lines. The presumed cleavage site for each protein is indicated with arrows.

FIG. 19: Domain structure of ATX and PC-1. Putative domains are indicated for the two homologous proteins, ATX and PC-1.

DETAILED DESCRIPTION OF THE INVENTION

Tumor cell motility is a critical component of invasion and metastasis, but the regulation of this motility is still poorly understood. At least some tumor cells secrete autocrine motility factors (AMF's) that stimulate motility in the producing cells. Like the analogous autocrine growth factors, these AMF's allow tumor cells independence from the host in this important component of the metastatic cascade. One AMF, autotaxin (ATX), has recently been purified to homogeneity from the human melanoma cell line, A2058 (Stracke, et al., 1992). The purified protein was enzymatically digested and the peptide fragments were separated by reverse phase HPLC. A number of these peptides have been sequenced by standard Edman degradation (Table 6) from different purifications and different enzymatic digestion. Sequence information, obtained initially on 19 purified tryptic peptides, confirmed that the protein is unique with no significant homology to growth factors or previously described motility factors. These peptide sequences have now been used as the basis for identifying and sequencing the cDNA clone for ATX. The present invention comprises an amino acid sequence of ATX as well as a nucleic acid sequence coding for the ATX protein.

TABLE 6

PEPTIDE SEQUENCES FOR AUTOTAXIN.

| PEPTIDE NO. | AMINO ACID SEQUENCE | SEQ ID: NO: |
| --- | --- | --- |
| ATX-18 | WHVAR | SEQ ID NO: 1 |
| ATX-19 | PLDVYK | SEQ ID NO: 2 |
| ATX-20 | YPAFK | SEQ ID NO: 3 |
| ATX-29 | PEEVTRPNYL | SEQ ID NO: 5 |
| ATX-34B | RVWNYFQR | SEQ ID NO: 38 |
| ATX-41 | HLLYGRPAVLY | SEQ ID NO: 29 |
| ATX-48 | VPPFENIELY | SEQ ID NO: 7 |
| ATX-59 | TFPNLYTFATGLY | SEQ ID NO: 32 |
| ATX-100 | GGQPLWITATK | SEQ ID NO: 8 |

TABLE 6-continued

PEPTIDE SEQUENCES FOR AUTOTAXIN.

| PEPTIDE NO. | AMINO ACID SEQUENCE | SEQ ID: NO: |
|---|---|---|
| ATX-101/223A | VNSMQTVFVGYGPTFK | SEQ ID NO: 9 |
| ATX-102 | DIEHLTSLDFFR | SEQ ID NO: 10 |
| ATX-103 | TEFLSNYLTNVDDITLVPETLGR | SEQ ID NO: 11 |
| ATX-104 | VNVISGPIDDYDYDGLHDTEDK | SEQ ID NO: 33 |
| ATX-204 | MHTARVRD | SEQ ID NO: 39 |
| ATX-205 | FSNNAKYD | SEQ ID NO: 40 |
| ATX-209 | VMPNIEK | SEQ ID NO: 41 |
| ATX-210 | TARGWECT | SEQ ID NO: 42 |
| ATX-212 | (N)DSPWT(N)ISGS | SEQ ID NO: 43 |
| ATX-214 | LRSCGTHSPYM | SEQ ID NO: 44 |
| ATX-215/34A | TYLHTYES | SEQ ID NO: 45 |
| ATX-213/217A | AIIANLTCKKPDQ | SEQ ID NO: 46 |
| ATX-216 | IVGQLMDG | SEQ ID NO: 47 |
| ATX-218/44 | TSRSYPEIL | SEQ ID NO: 48 |
| ATX-223B/24 | QAEVSSVPD | SEQ ID NO: 49 |
| ATX-224 | RCFELQEAGPPDDC | SEQ ID NO: 50 |
| ATX-229 | SYTSCCHDFDEL | SEQ ID NO: 51 |
| ATX-244/53 | QMSYGFLFPPYLSSSP | SEQ ID NO: 52 |

ATX is a glycosylated protein due to its high affinity for concanavalin A and amino acid sequence analysis of the ATX peptides. ATX has been demonstrated to be a 125 kDa glycoprotein whose molecular weight reduced to 100–105 kDa after deglycosylation with N-glycosidase F. The calculated molecular weight of the cloned protein is 100 kDa (secreted form) or 105 kDa (full length protein). Based on amino acid composition, the estimated pI is 9.0 which is higher than the pI determined by 2-D gel electrophoresis analysis (7.7–8.0) of purified ATX. This difference can be explained by the presence of sialic acid residues on the sugar moieties.

Autotaxin is secreted by A2058 human melanoma cells cultured in low abundance in serum-free conditioned medium. Autotaxin is a potent new cytokine with molecular mass 125 kDa which has been purified to homogeneity from the conditioned medium of the human melanoma cell line, A2058, utilizing sequential chromatographic methods as described herein. This new cytokine, termed autotaxin (ATX), is a basic glycoprotein with pI ~7.8. ATX is active in the high picomolar to low nanomolar range, stimulating both chemotactic and chemokinetic responses in the ATX-producing A2058 cells as well as other tumor cells. This motile response is abolished by pretreatment of the cells with pertussis toxin. ATX may therefore act through a G protein-linked cell surface receptor. These characteristics distinguish ATX from several small growth factors and interleukins which are implicated in tumor cell motility (Stracke et al., 1988; Ruff et al., 1985; Maciag et al., 1984; Gospodarowicz, 1984; Van Snick, 1990; Yoshimura 1987).

The protein of the present invention, which in one embodiment is derived from A2058 human melanoma cells, can be prepared substantially free from proteins with which it is normally associated using, for example, the purification protocol disclosed herein. Alternatively, the protein of the present invention can be prepared substantially free from proteins, by cloning and expressing the cDNA encoding autotaxin as disclosed herein.

A large volume of serum-free conditioned medium from appropriate producer cells (e.g., tumor cells) is collected and concentrated approximately 500-fold. This concentrated conditioned medium is then separated from other contaminating proteins by techniques that rely on the chemical and physical characteristics of the protein. These include the molecular weight, relative hydrophobicity, net charge, isoelectric focusing point, and the presence of lectin-binding sugar residues on the protein.

Alternatively, the protein, or functional portion thereof, can be synthesized using chemical or recombinant means.

The protein of the present invention has a potent biological activity. Purified ATX is active in the picomolar range and 1 unit of activity corresponds to a concentration of approximately 500 pM as assessed by the cell motility assay described herein and elsewhere (Stracke et al., 1989).

The protein of the present invention has a molecular size, as determined by two dimensional gel electrophoresis, of from 120 to 130 kDa, or more specifically, about 125 kDa. Further, the protein of the present invention can have a pI in the range of 7.5 to 8.0, preferably, approximately 7.7. The present invention relates to autotaxin and peptides thereof having cell motility properties as described herein. These proteins and peptides thereof can be produced by isolation from a natural host or isolation as an expression product from a recombinant host.

The present invention also relates to a DNA segment coding for a polypeptide comprising an amino acid sequence corresponding to ATX, or a unique portion of such a sequence (unique portion being defined herein as at least 5, 10, 25, or 50 amino acids). In one embodiment, the DNA segment encodes any one of the amino acid sequences shown in SEQ ID NO:1 to SEQ ID NO:11 and SEQ ID NO:26 to SEQ ID NO:33. Another embodiment uses larger DNA fragments encoding amino acid sequences shown in SEQ ID NO:34, SEQ ID NO: 36 and SEQ ID NO:38. The entire coding region for autotaxin can also be used in the present invention shown in SEQ ID NO:66 through SEQ ID NO:69.

In another embodiment, the present invention relates to a recombinant DNA molecule comprising a vector (for example plasmid or viral vector) and a DNA segment coding for a polypeptide corresponding to ATX, as can be prepared by one skilled in the art. Preferably, the coding segment is present in the vector operably linked to a promoter. The present invention also relates to a recombinant protein produced from a host cell expressing a cDNA containing a coding region of ATX. Examples of ATX cDNAs from a variety of sources have been cloned and can be used for expression, including inter alia A2058 carcinoma cells, N-tera 2D1 cells and human liver.

In a further embodiment, the present invention relates to a cell containing the above-described recombinant DNA molecule. Suitable host cells include procaryotic cells (such as bacteria, including E. coli) and both lower eucaryotic cells (for example, yeast) and higher eucaryotic cells (for example, mammalian cells). Introduction of the recombinant molecule into the host cells can be effected using methods known in the art.

In another embodiment, the present invention relates to a method of producing a polypeptide having an amino acid sequence corresponding to ATX. The method comprises culturing the above-described cells under conditions such that the DNA segment is expressed, and isolating ATX thereby produced.

In a further embodiment, the present invention relates to an antibody having affinity for ATX or peptide fragments thereof. The invention also relates to binding fragments of such antibodies. In one preferred embodiment, the antibodies are specific for ATX peptides having an amino acid sequence set forth in one of SEQ ID NO:1 through SEQ ID NO:11 and SEQ ID NO:26 through SEQ ID NO:34, SEQ ID NO: 36 and SEQ ID NO:38 through SEQ ID NO:52. In addition, the antibodies may recognize an entire autotaxin protein.

Antibodies can be raised to autotaxin or its fragment peptides, either naturally-occurring or recombinantly produced, using methods known in the art.

The ATX protein and peptide fragments thereof described above can be joined to other materials, particularly polypeptides, as fused or covalently joined polypeptides to be used as carrier proteins. In particular, ATX fragments can be fused or covalently linked to a variety of carrier proteins, such as keyhole limpet hemocyanin, bovine serum albumin, tetanus toxoid, etc. See for example, Harper and Row, (1969); Landsteiner, (1962); and Williams et al., (1967), for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts. Description of techniques for preparing such monoclonal antibodies may be found in Stites et al., and references cited therein, and in particular in Kohler and Milstein (1975), which discusses one method of generating monoclonal antibodies.

In another embodiment, the present invention relates to an oligonucleotide probe synthesized according to the sense or antisense degenerative sequence set forth in one of SEQ ID NO:1 through SEQ ID NO:11, SEQ ID NO:26 through SEQ ID NO:33, SEQ ID NO:39 through SEQ ID NO:52, and SEQ ID NO:55 through SEQ ID NO:65.

Protein database searches of this sequence revealed a 45% amino acid identity with the plasma cell membrane marker protein, PC-1. ATX and PC-1 appear to share a number of domains, including two somatomedin B domains, the loop region of an EF hand, and the enzymatic site of type I phosphodiesterase/nucleotide pyrophosphatase. Like PC-1, ATX hydrolyzes p-nitrophenyl thymidine-5'-monophosphate, a type 1 phosphodiesterase substrate. This enzymatic function of ATX suggests a newly identified function for ecto/exo-enzymes in cellular motility.

In a further embodiment, the present invention relates to a method of diagnosing cancer metastasis and to a kit suitable for use in such a method. Preferably, antibodies to ATX can be used in, but not limited to, ELISA, RIA or immunoblots configurations to detect the presence of ATX in body fluids of patients (e.g. serum, urine, pleural effusions, etc.). These antibodies can also be used in immunostains of patient samples to detect the presence of ATX.

In yet another embodiment, the present invention relates to in vivo and in vitro diagnostics. ATX may be radiolabelled, by means known to one skilled in the art, and injected in cancer patients with appropriate ancillary substances also known to one skilled in the art, in order to ultimately detect distant metastatic sites by appropriate imagery. The level of ATX in tissue or body fluids can be used to predict disease outcomes and/or choice of therapy which may also include ATX inhibitors.

In a further embodiment, the present invention relates to a treatment of cancer. ATX antibodies can be cross-linked to toxins (e.g., Ricin A), by means known to one skilled in the art, wherein the cross-linked complex is administered to cancer patients with appropriate ancillary agents by means known to one skilled in the art, so that when the antibody complex binds to the cancer cell, the cell is killed by the cross-linked toxin.

In another embodiment, the different localizations of the normal versus tumorous forms of the ATX proteins within the tissue can be used as a tool for diagnosis and prognosis. The stage of disease progression can be monitored by elevated levels of ATX in the extracellular space as opposed to its normal cell membranes association. In addition, treatment methods for control of tumor progression can be designed to specifically block the activity of the secreted form of ATX. Such methods would have a preferential effect upon secreted ATX during tumor progression while not effecting normal ATX formation.

Yet another embodiment utilizes the hot spot located in the region from approximately nucleotides 1670 through 1815, as a marker gene for identification of tissues carrying a tumorous form of ATX.

The present invention is described in further detail in the following non-limiting examples.

EXAMPLES

The following protocols and experimental details are referenced in the Examples that follow:

Materials. The polycarbonate Nuclepore membranes and the 48-well microchemotaxis chambers were obtained from Neuro Probe, Inc. Pertussis toxin (PT), ethylene glycol (biotechnology grade), methyl α-D-mannopyranoside were obtained from commercial vendors. The ampholyte, pH 3–10 Bio-Lyte and pH 8–10 Bio-Lyte, were obtained from Bio-Rad. Phenyl Sepharose CL-4B; affi-Gel concanavalin A; ZORBAX BioSeries-WAX (weak anion exchange) column (9.4 mm×24 cm); Spherogel-TSK 4000SW, 3000SW and 2000SW columns (each 7.5 mm×30 cm); the Pro-Pac PA1 (4×50 mm) strong anion exchange column; the Aquapore RP300 C-8 reverse phase column (220×2.1 mm); and the AminoQuant C-18 reverse phase column (200×2.1 mm) were also obtained from commercial sources.

Affi-Gel 10 affinity resin was from Bio-Rad. The Gene-Amp PCR Reagent kit with AmpliTaq and the GeneAmp RNA PCR kit were purchased from Perkin-Elmer. The 5' RACE kit came from Gibco BRL Life Technologies, Inc. The p-nitrophenyl thymidine-5'monophosphate was obtained from Calbiochem Biochemicals.

Ethylene glycol (biotechnology grade) was from Fisher Biochemicals (Pittsburg, Pa.). Peptide N-glycosidase F ("PNGase F"), O-glycosidase, neuraminidase (*Arthrobacter ureafaciens*), and swainsonine ("Swn") came from Boehringer-Mannheim (Indianapolis, Ind.). 1-Deoxymannojirimycin ("dMAN"), and N-methyl-1-deoxynojirimycin ("NMdNM") were from Oxford GlycoSystems, Inc. (Rosedale, N.Y.). Biotinylated concanavalin A, HRP-conjugated streptavidin, and HRP-conjugated goat anti-rabbit immunoglobulin were purchased from Pierce Chemicals (Rockford, Ill.). Polyvinyl pyrrolidone-free polycarbonate membranes and the microchemotaxis chamber were from NeuroProbe, Inc. (Cabin John, Md.).

Cell Culture. The human melanoma cell line A2058, originally isolated by Todaro (Todaro et al., 1980), was maintained as previously described by Liotta (Liotta et al., 1986). The N-tera 2 (D1 clone) was a kind gift from Dr. Maxine Singer, Laboratory of Biochemistry, National Cancer Institute, National Institutes of Health and was maintained as described (Andrews, P. W., Goodfellow, P. N. and Bronson, D. L. (1983) (*Cell surface characteristics and other markers of differentiation of human teratocarcinoma cells in culture.*).

Production of Autotaxin. A2058 cells were grown up in T-150 flasks, trypsinized, and seeded into 24,000 cm² cell factories at a cell density of 1×10¹⁰ cells/factory. After 5–6 days, the serum-containing medium was removed and the cells were washed with DPBS. The factories were maintained in DMEM without phenol red, supplemented with 4 mM glutamine, 100 units/ml penicillin, 100 μg/ml streptomycin, 5 μg/ml crystallized bovine serum albumin, 10 μg/ml bovine insulin, and 1 μM aprotinin. Culture supernatants were harvested every 3 days, frozen at −40° C. and replaced with fresh serum-free medium. Each cycle of supernatant was tested for ATX production with a cell motility assay detailed below. Typically, a cell factory continued to be productive for 9–11 of these cycles.

After accumulation of approximately 45–60 L of supernatant, the culture supernatants were thawed and concentrated down to 2–2.5 L using an Amicon S10Y30 spiral membrane ultrafiltration cartridge. This supernatant was further concentrated in an Amicon high performance ultrafiltration cell using Diaflo membranes. The final volume achieved from 100–200 L of conditioned medium was typically 250–400 ml. All ultrafiltrations were performed at 4° C.

Cell Motility Assays. Purification of autotaxin was monitored by testing the motility-stimulating capacity of the fractions collected from the columns. These fractions were in buffers unsuitable for a chemotaxis assay so each fraction had to be washed into an appropriate buffer, i.e., 0.1% (w/v) BSA in DPBS containing calcium and magnesium. This dialysis was performed by adding aliquots of each fraction to be tested into Centricon-30™ ultrafiltration tubes, which retain molecular species larger than 30,000 daltons.

The assay to determine motility was performed in triplicate using a 48-well microchemotaxis chamber as described elsewhere in detail (Stracke et al., 1987; Stracke, et al., 1989). The Nuclepore™ membranes used in these modified Boyden chambers were fixed and stained with Diff-Quik.™ Chemotaxis was quantitated either by reading the stained membranes with a 2202 Ultroscan laser densitometer or by counting 5 randomly chosen high power fields (HPF) under light microscopy (400×) for each replicate. Densitometer units (wavelength~633 nm) have been shown to be linearly related to the number of cells per HPF (Taraboletti, 1987; Stracke, et al., 1989). Typically, unstimulated motility (background) corresponded to 5–10 cells/HPF and highly responding cells to 70–100 cells/HPF above unstimulated background (i.e., 75–110 total cells/HPF).

For experiments using PT, the toxin was pre-incubated with the cells for 1–2 hr. at room temperature prior to the assay and maintained with the cells throughout the assay (Stracke, et al., 1987). The treated cells were tested for their motility response to the chemoattractant as well as for unstimulated random motility.

Purification of Autotaxin. Ammonium sulfate, to a final concentration of 1.2M, was added to the concentrated A2058 conditioned medium for 1 hr. at 4° C. The solution was spun in a RC2-B Ultraspeed Sorvall centrifuge at 10,000×g for 15 min. Only the supernatant had the capacity to stimulate motility.

In the first step, the sample was fractionated by hydrophobic interaction chromatography using 200 ml phenyl Sepharose CL-4B column equilibrated into 50 mM Tris (pH 7.5), 5% (v/v) methanol and 1.2M ammonium sulfate. The supernatant from the ammonium sulfate fractionation was added to this column and eluted using linear gradients of 50 mM Tris (pH 7.5), 5% (v/v) methanol, with decreasing (1.2–0.0) M ammonium sulfate and increasing (0–50) % (v/v) ethylene glycol at 1 ml/min.

The active peak was pooled, dialyzed into 50 mM Tris, 0.1M NaCl, 0.01M CaCl$_2$, 20% (v/v) ethylene glycol, and subjected to a second fractionation by lectin affinity chromatography using a 40 ml Affi-Gel concanavalin A column run at 1 ml/min. The sample was eluted in a stepwise fashion in the same buffer with 0, 10, and 500 mM methyl α-mannopyranoside added successively. Fractions from each step of the gradient were pooled and tested for their capacity to stimulate motility.

In the third purification step, the sample that eluted at 500 mM α-methyl-mannopyranoside was dialyzed into 10 mM Tris (pH 7.5) with 30% (v/v) ethylene glycol and fractionated by weak anion exchange chromatography. Chromatography was carried out on a ZORBAX BioSeries-WAX column using a Shimadzu BioLiquid chromatograph and eluted with a linear gradient of (0.0–0.4M) sodium chloride at 3 ml/min.

The active peak was pooled, dialyzed against 0.1M sodium phosphate (pH 7.2), 10% (v/v) methanol, and 10% (v/v) ethylene glycol, and subjected to a fourth fractionation step on a series of Spherigel TSK columns (4000SW, 4000SW, 3000SW, 2000SW, in that order). This molecular sieve step was run using the Shimadzu BioLiquid chromatograph at 0.4 ml/min.

The active peak was pooled and dialyzed into 10 mM Tris (pH 7.5), 5% (v/v) methanol, 20% (v/v) ethylene glycol and subjected to a fifth (strong anion exchange) chromatography step, a Pro-Pac PA1 column run at 1 ml/min using a Dionex BioLC with AI450 software. The sample was eluted with a linear gradient of (0.0–0.4M) NaCl.

In order to calculate activity yields after each step of purification, a unit of activity had to be derived. The dilution curve of ATX was biphasic with a broad peak and a linear range at sub-optimal concentrations. One unit of activity/ well (i.e., 40 units/ml) was defined as 50% of the maximal activity in a full dilution curve. This allowed calculation of the activity contained in any volume from the dilution needed to achieve 1 unit/well. Therefore, if a 1:10 dilution were needed in order to produce 1 unit of activity/well, the material contained 10×40=400 units/ml.

Gel Electrophoresis. Protein samples were analyzed by SDS-polyacrylamide gel electrophoresis using the conditions of Laemmli (Laemmli, 1970). In brief, 7 or 8% SDS-containing polyacrylamide gels were prepared or prepoured (8–16%) gradient gels were obtained commercially. Samples were prepared with or without reducing conditions (5% β-mercaptoethanol). After electrophoretic separation, the gels were stained using Coomassie Blue G-250 as previously described (Neuhoff, et al., 1988). In this staining protocol, which ordinarily requires no destaining step, the Coomassie stain appears to be able to stain as little as 10 ng of protein.

For two-dimensional electrophoresis, the protein, in 20% ethylene glycol, was dried in a Speed-vac and redissolved in loading solution: 9M urea, 1% (v/v) pH 3–10 Bio-Lyte, and 2.5% (v/v) Nonidet-P40. This sample was then subjected to isoelectric focusing (O'Farrell, 1975) using a Bio-Rad tube cell in 120×3 mm polyacrylamide tube gels containing 9M urea, 2% (v/v) pH 3–10 Bio-Lyte, 0.25% (v/v) pH 8–10 Bio-Lyte and 2.5% (v/v) Nonidet-P40. Reservoir solutions were 0.01M phosphoric acid and 0.02M NaOH. Non-equilibrium isoelectric focusing (O'Farrell, et al., 1977) was run initially with constant voltage (500 v) for 5 hr. Since the protein was basic, the procedure was repeated under equilibrium conditions (500 v for 17 hr.). Electrophoresis in the second dimension was performed on a 7.5% polyacrylamide using the conditions of Laemmli (1970). The gel was stained with Coomassie Blue G-250 as above.

Preparation of peptides for internal sequence of autotaxin. Homogeneous ATX was sequentially digested with cyanogen bromide and, following reduction and pyridylethylation, with trypsin (Stone, et al., 1989). The resulting fragments were then separated by gradient elution on an Aquapore RP300 C-8 reverse phase column: 0.1% (v/v) trifluoroacetic acid and (0–70)% acetonitrile over 85 min. at a flow rate of 0.2 ml/min. A Dionex AI450 BioLC system was utilized and fractions were collected manually while monitoring the absorbance at 215 nm.

Sequence analysis of peptides. The amino acid sequences of peptides resulting from digestion and purification of ATX peptides #1–7 and 12–18, corresponding to SEQ ID NO:1 through SEQ ID NO:7 and SEQ ID NO:26 through SEQ ID NO:32, respectively, were determined on a Porton Instruments 2020 off-line sequenator using standard program #1. Phenylthiohydantoin amino acid analysis of sequenator runs were performed on a Beckman System Gold HPLC using a modified sodium acetate gradient program and a Hewlett-Packard C-18 column. ATX-100 (SEQ ID NO:8), ATX-101 (SEQ ID NO:9), ATX-102 (SEQ ID NO:10), ATX-103 (SEQ ID NO:11) and ATX 104 (SEQ ID NO:33) were sequenced from gel-purified ATX.

Protein databases (Pearson, et al. 1988) that were searched for homologies in amino acid sequence with the ATX peptides include: GenBank (68.0), EMBL (27.0), SWISS-PROT (18.0), and GenPept (64.3).

Example 1

Purification of Autotaxin

The A2058 cells had been previously shown to produce protein factors which stimulate motility in an autocrine fashion (Liotta, et al., 1986). Conditioned medium from these cells was therefore used to identify and purify a new motility-stimulating factor, which is here named autotaxin and referred to as ATX. Since the purification was monitored with a biological assay, motility-stimulating activity had to be maintained throughout. The activity proved to be labile to freezing, acidic buffers, proteases (but not DNase or RNase), reduction, strong chaotrophic agents (e.g. >4M urea), and a variety of organic solvents (isopropanol, ethanol, acetonitrile). An organic solvent, ethylene glycol, which did not decrease bioactivity, was added for both storage and chromatographic separation.

100–200 L of serum-free conditioned medium were required in order to produce enough ATX for amino acid sequence analysis. The medium contained low concentrations of both BSA (5 $\mu$g/ml) which was needed as a carrier protein and insulin (10 $\mu$g/ml) which was required to support cell growth in low protein medium. Ultrafiltration to concentrate this large volume was performed with low protein-binding YM30 membranes which retain molecular species with $M_r$>30,000. As seen in Table 1, 200 L of conditioned medium prepared in this manner resulted in 10×10$^6$ units of activity. However, the initial unfractionated conditioned medium contained additional substances known to stimulate activity, particularly insulin, which does not completely wash out in the ultrafiltration step and which is additive to the motility stimulating activity in a complex manner (Stracke, et al., 1989). This had to be taken into account in order to determine yields for subsequent steps in which insulin had been removed.

TABLE 1

PURIFICATION OF AUTOTAXIN

| Purification Step | Protein (mg) | Activity[a] (total units) | Specific Activity (units/mg) | Recovery (%)[b] |
|---|---|---|---|---|
| 200 L Conditioned Medium | 33,000 | 10,000,000[c] | 300 | |
| Phenyl Sepharose | 1,235 | 460,000 | 370 | 100 |
| Concanavalin A | 58 | 660,000 | 11,400 | 100 |
| Weak Anion Exchange | 4.5 | 490,000 | 110,000 | 100 |
| TSK Molecular Sieves | ~0.4[d] | 220,000 | 550,000 | 48 |
| Strong Anion Exchange | ~0.04[d] | 24,000[e] | 600,000 | 5.2 |

[a]Activity calculated from Boyden chamber assay. The dilution which resulted in 50% of maximal activity (generally approximately 20 laser density units or ~40 cells/HPF) was chosen to have 1 unit of activity per well (equivalent to 40 units/ml).
[b]Recovery was estimated from activity, after the first purification column (i.e., phenyl sepharose).
[c]Initial activity in the unfractionated conditioned medium reflected the fact that insulin was used in the medium as a necessary growth factor under low protein conditions.
[d]Estimated protein is based on quantification by amino acid analysis.
[e] This specific activity for purified protein corresponds to ~10 fmol ATX/ unit of motility activity (in a Boyden chamber well).

Figure 1:
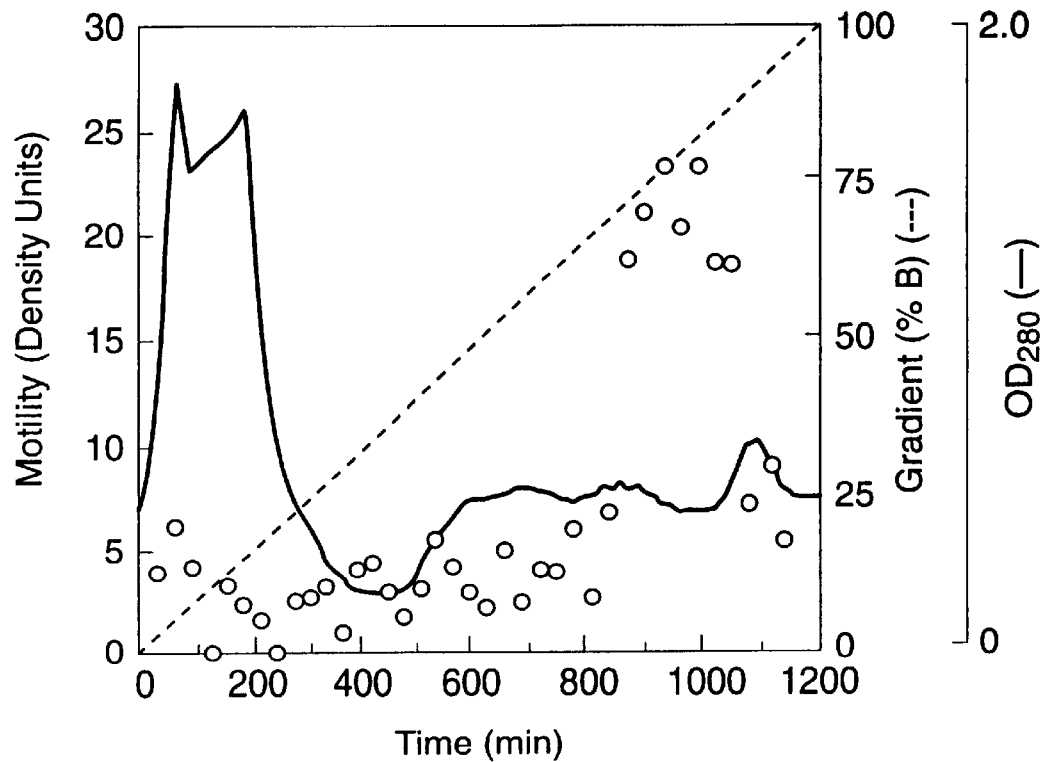
FIG. 1. Fractionation of ATX by hydrophobic interaction. A 200 ml sample of A2058 conditioned media was chromatographed on a 200 mL column of phenyl Sepharose-4B. Buffer A was 50 mM Tris (pH 7.5), 5% methanol, and 1.2M ammonium sulfate. Buffer B was 50 mM Tris (pH 7.5), 5% methanol and 50% ethylene glycol. The gradient (—) represents a double linear gradient with decreasing ammonium sulfate (1.2 to 0.0M) and increasing ethylene glycol (0 to 50%). Absorbance was monitored at 280 nm (_) and indicated that most of the protein did not bind to the column. Ten ml fractions were assayed for motility stimulating capacity using the Boyden Chamber assay (o). The peak of motility activity occurred between 900 and 1050 minutes, ~12% of the gradient.

The first step in the purification involved fractionation by hydrophobic interaction chromatography using a phenyl Sepharose CL-4B column. The results are shown in FIG. 1. Most proteins, including insulin, eluted from the column in early fractions or in the void. However, the peak of activity eluted relatively late. The activity which was purified was estimated as 460,000 units ±20% (Table 1). As the pooled peak of activity from the phenyl Sepharose fractionation is considered to be the first sample without significant insulin contamination, subsequent yields are measured against its total activity. Gel electrophoresis of a small portion of the pooled peak of activity (FIG. 6A, column 2) revealed a large number of protein bands with BSA predominant from the original conditioned medium.

Figure 2:
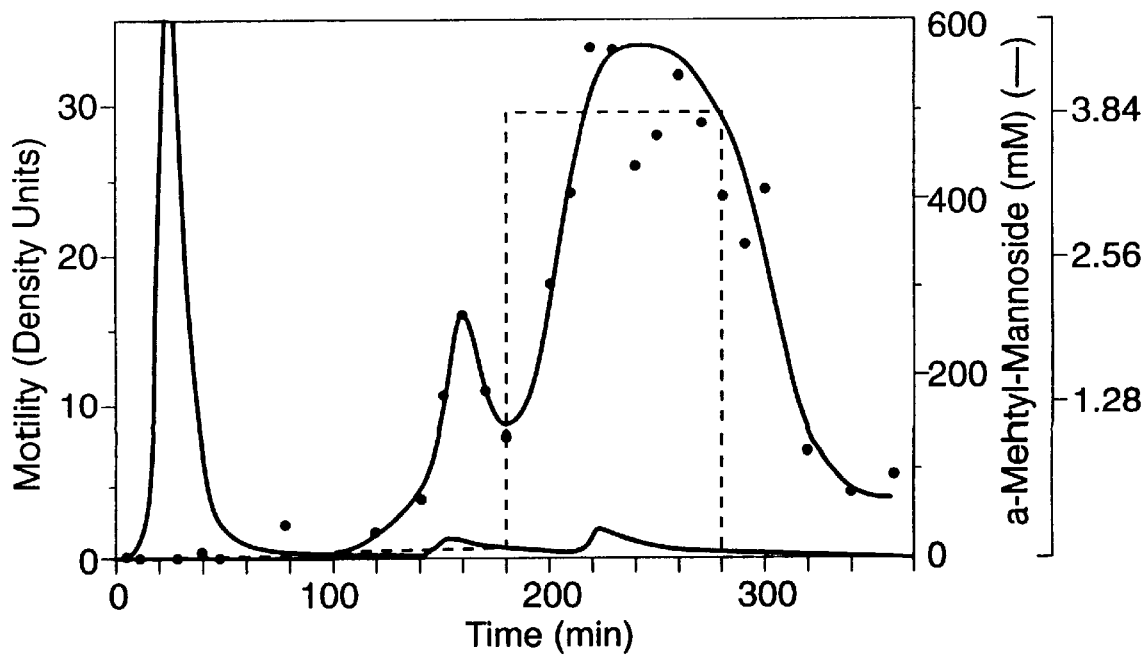
FIG. 2. Isolation of ATX by lectin affinity chromatography. 20 ml portions of the phenyl Sepharose activity peak were affinity purified on a 40 ml Concanavalin A Affi-Gel column. The bound components were eluted with a step gradient (—) of methyl α-D-mannopyranoside (0.0 mM, 10 mM, and 500 mM) in a buffer consisting of 0.05M Tris (pH 7.5), 0.1M NaCl, 0.01M $CaCl_2$ and 20% ethylene glycol. Absorbance was monitored at 280 nm (_) and indicated that the majority of the protein components did not bind to the column. Motility was assayed in 10 mL fractions ( . . . o . . . ) and was found predominantly in the 500 mM elution concentration. One of seven chromatographic runs is shown.

In the second step of purification, the active peak was applied to the lectin affinity column, Affi-Gel concanavalin A. As shown in FIG. 2, most protein (estimated to be 90% of the total absorbance at 280 nm) failed to bind to the column at all. The non-binding fraction contained essentially no motility-stimulating activity (see dotted line in FIG. 2). When a linear gradient of methyl α-D-mannopyranoside was applied to the column, chemotactic activity eluted off in a prolonged zone, beginning at a concentration of approximately 20 mM sugar. Consequently, a step gradient was used to elute. Pure BSA failed to bind to con A.

Activity was found primarily in the 500 mM step of methyl α-D-mannopyranoside. There appeared to be no significant loss of activity as seen in Table 1; however, specific activity (activity/mg total protein) increased thirty-fold. Gel electrophoresis of the pooled and concentrated peak (FIG. 6A, column 3) revealed that the BSA overload was no longer apparent and the number of bands were much reduced. When the unbound protein was concentrated and applied to a gel, it appeared identical to the active peak from phenyl Sepharose-4B with a large BSA band.

Figure 3:
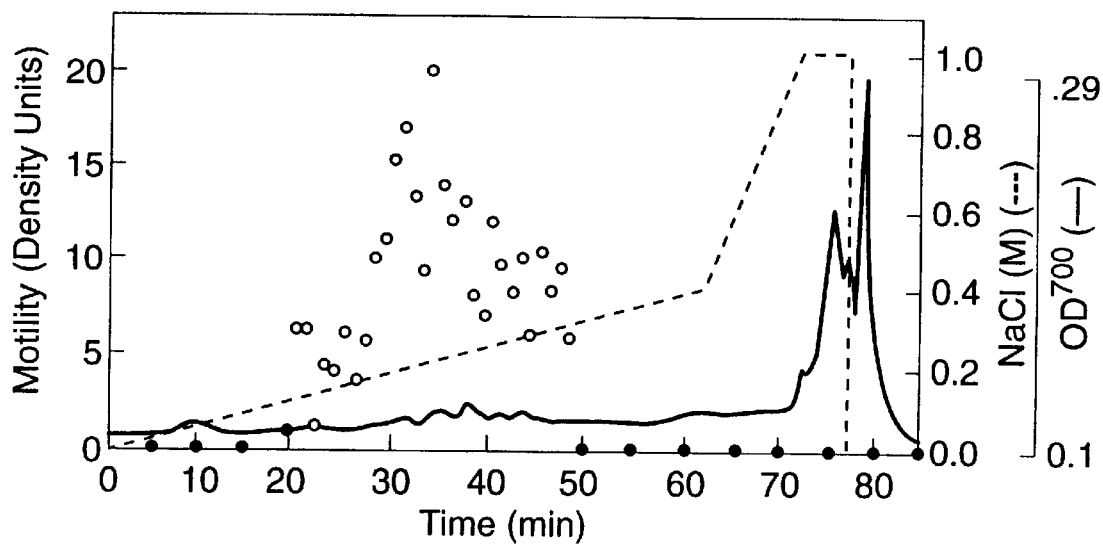
FIG. 3. Purification of ATX by weak anionic exchange chromatography. Approximately 30% of the activity peak eluted from the Con A affinity column was applied to a ZORBAX BioSeries-WAX column. The bound components were eluted with an NaCl gradient (—) in a buffer consisting of 10 mM Tris (pH 7.5) and 30% ethylene glycol. Motility (o) was assayed in 1.0 ml fractions. The peak of activity eluted in a discrete but broad region in the shallow portion of the gradient. Absorbance was monitored at 230 nm (_). The majority of the protein components not associated with activity bound strongly to the column were eluted at 1.0M NaCl. One of two chromatographic runs is shown.
Figure 6A:
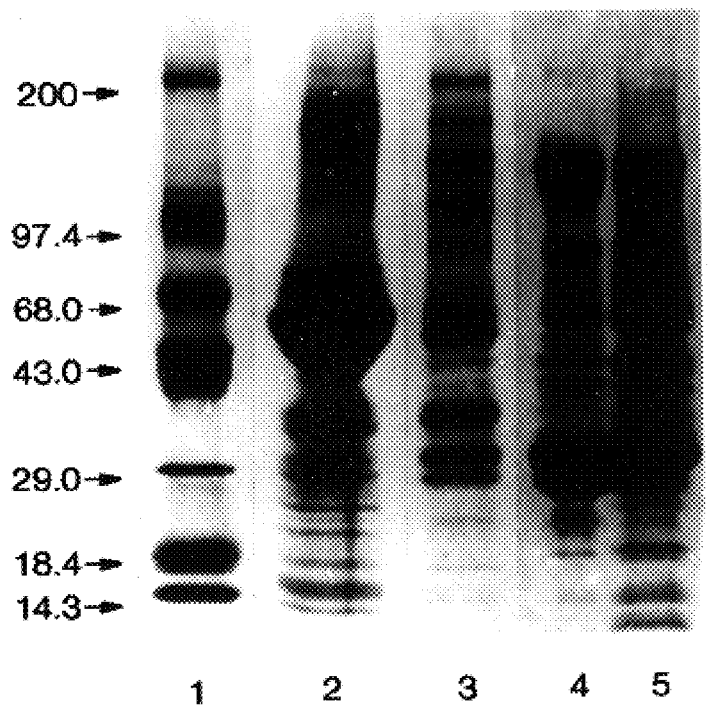
FIGS. 6A, 6B and 6C. Protein components associated with the activity peaks from various stages of purification. The activity peak from each chromatographic fractionation was pooled, concentrated and analyzed by SDS-polyacrylamide gel electrophoresis. Molecular weight standards are in Lane 1 for each panel. Panel 6A) 8–16% gradient gel of the first three purification steps, run under non-reducing conditions. Lane 2 is an aliquot of the pooled activity peak eluted from the phenyl sepharose fractionation. Lane 3 is an aliquot of the pooled activity peak eluted from the Con A affinity purification. Lanes 4 and 5 show the "peak" and "shoulder" of activity fractionated by weak anion exchange chromatography (FIG. 3). Panel 6B) 7% gel of the activity peak fractionated by molecular sieve exclusion chromatography. Lanes 2 and 3 show the protein separation pattern of the total pooled activity peak when the gel was run under non-reducing and reducing conditions, respectively. Panel 6C) 8–16% gradient gel of the final strong anionic exchange chromatographic separation, run under non-reducing conditions. Lane 2 comprises ~1% of the total pooled activity peak eluted from the column.

The third purification step involved fractionating the previous active peak by weak anion exchange chromatography as shown in FIG. 3. Under the running conditions, activity eluted in a broad peak-shoulder or double peak in the middle of the shallow portion (0.0–0.4M) of the NaCl gradient. The largest proportion of protein, lacking in motility-stimulating capacity, bound strongly to the column and eluted off in high salt (1M NaCl). There appeared to be no significant loss of activity, though specific activity increased by twenty-fold (Table 1). Analysis by gel electrophoresis of both the peak (28–34 min. in FIG. 3) and the shoulder (35–45 min. in FIG. 3) is shown in FIG. 6A (columns 4 and 5, respectively). Two predominant protein bands resulted: a broad doublet around 25–35 kDa and a second doublet around 110–130 kDa.

Figure 4:
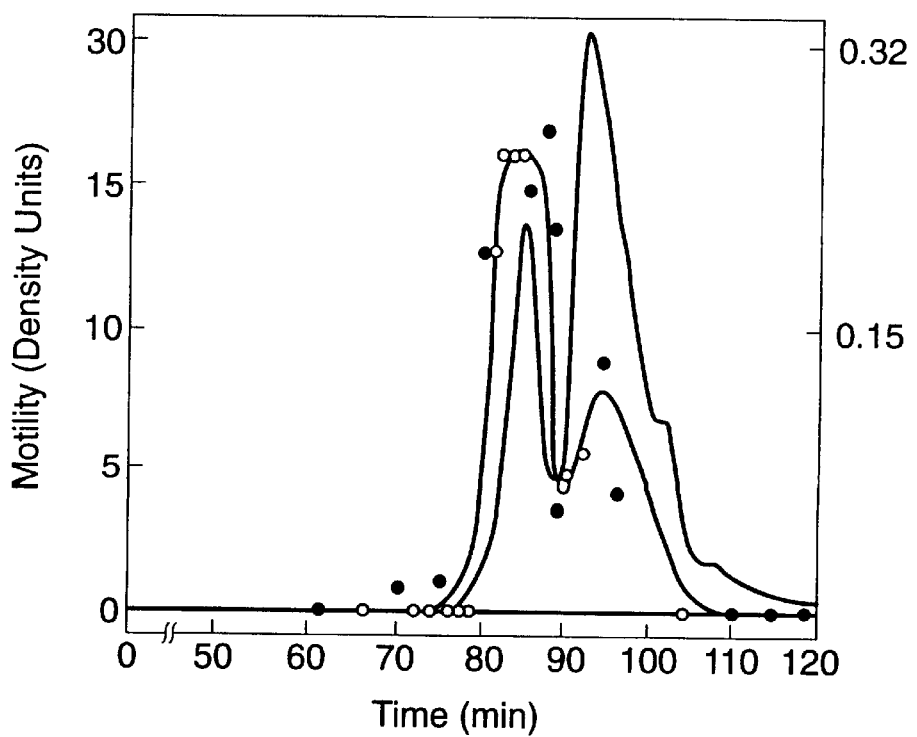
FIG. 4. Purification of ATX by molecular sieve exclusion chromatography. The entire activity peak eluted from the weak anion exchange column was applied to a series of TSK columns (4000SW, 4000SW, 3000SW, and 2000SW, in this order). Proteins were eluted in a buffer consisting of 0.1M $NaPO_4$ (pH 7.2) with 10% methanol and 10% ethylene glycol. Two major protein peaks were evident by monitoring the absorbance at 235 nm (_). Motility ( . . . o . . . ) was assayed in 0.4 ml samples and found predominantly in the first, smaller, protein peak.
Figure 6B:
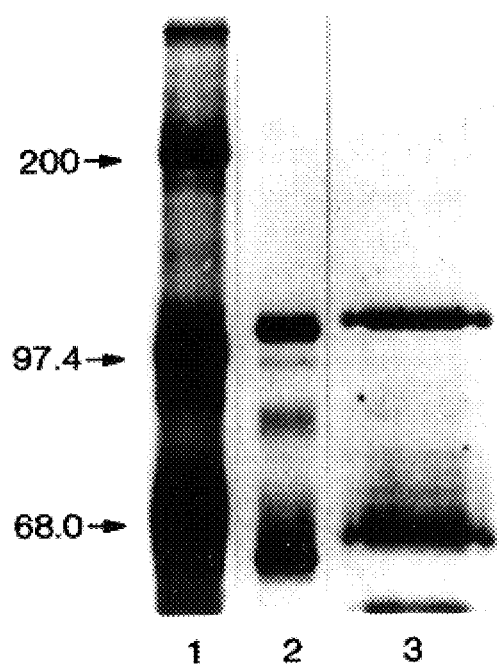

In the fourth purification step, the active peak was applied to a series of molecular sieves. Spectrophotometric monitoring of the eluant revealed two large peaks of protein (FIG. 4). Activity corresponded to the first, higher molecular weight peak. Recovery of activity was ~48% with a five-fold increase in specific activity. Analysis by gel electrophoresis was performed under non-reducing and reducing conditions as shown in FIG. 6B (columns 2 and 3, respectively). This fractionation step had essentially removed all contaminating protein of molecular weight <55 kDa. The predominant band remaining has a molecular weight of 120 kDa unreduced and 125 kDa reduced; there are two minor bands with molecular weights 85 kDa and 60 kDa. The fact that the 120 kDa protein changes so little in electrophoretic mobility after reduction would tend to indicate a paucity of disulfide bonds. However, the existing disulfide bonds have functional significance because motility-stimulating activity is labile to reduction.

Figure 5:
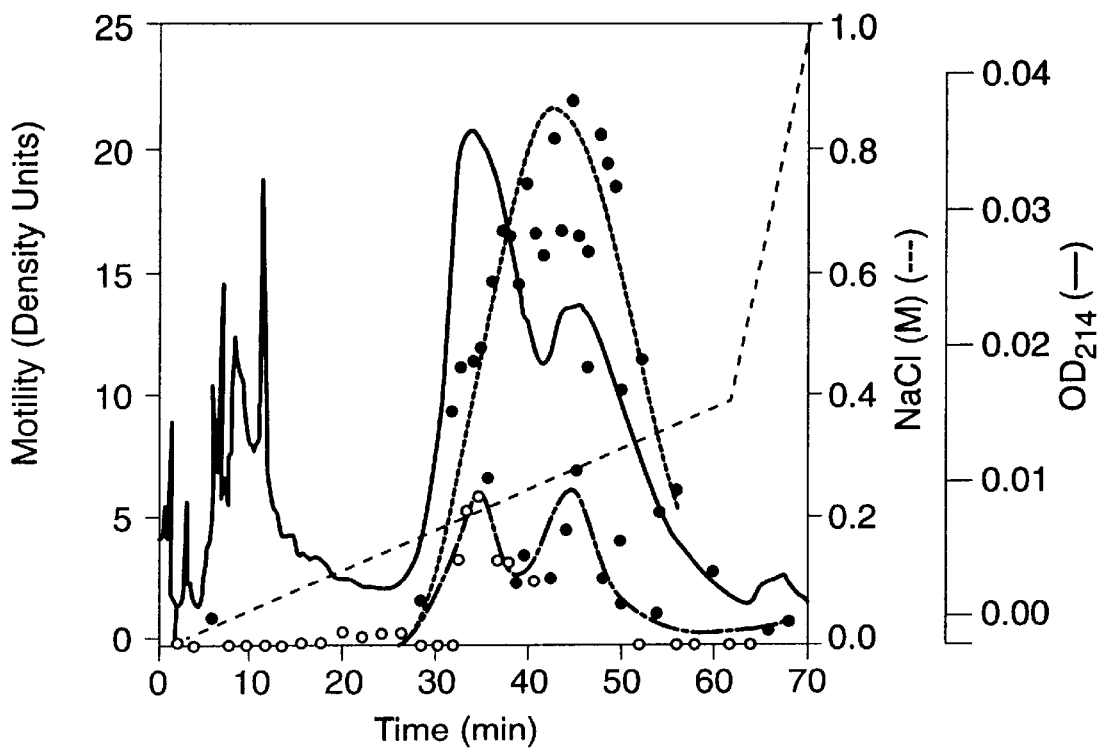
FIG. 5. Final purification of ATX by strong anionic exchange chromatography. Approximately 15% of the activity peak from the molecular sieve exclusion series was applied to a Pro-Pac PA1 column. Protein which bound to the column was eluted with a NaCl gradient (—) in a buffer consisting of 10 mM Tris (pH 7.5), 5% methanol and 20% ethylene glycol. Absorbance was monitored at 215 nM (_). Motility activity was assayed in 1.0 ml fractions at two different dilutions: 1/5 ( . . . o . . . ) or 1/15 (._.o._.). Activity was found to correspond to a double protein peak in the central region of the gradient.
Figure 6C:
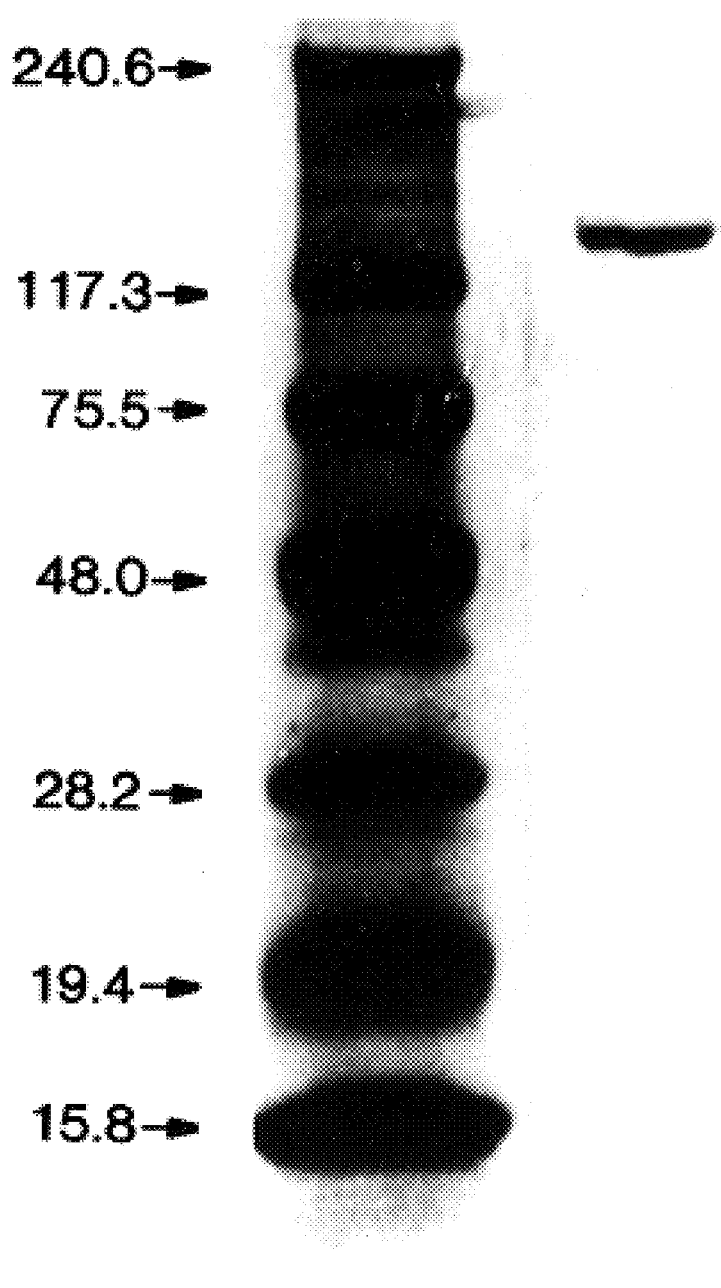

The fifth purification step involved fractionation of the active peak by strong anion exchange chromatography. As shown in FIG. 5, activity corresponds to two broad optical absorbance peaks in the middle of the gradient with contaminating proteins eluting earlier. These two peaks were identical by amino acid analysis and by polyacrylamide gel electrophoretic separation. They presumably represent different glycosylation states of the same parent protein. Activity is shown in FIG. 5 at two different sample dilutions. Several dilutions of the fractionated samples were often necessary in order to resolve the true "peak" of activity as the shape of the ATX dilution curve was not sharp due to saturation and down regulation at high concentrations. Recovery from this chromatographic step is lower (5% compared to phenyl Sepharose), as might be expected when a minute quantity of protein is applied to a column; however, specific activity again increased (Table 1). Analysis by gel electrophoresis revealed a single protein band at molecular weight 120 kDa, unreduced (FIG. 6C, column 2).

Example 2

Characterization of Autotaxin

Figure 7:
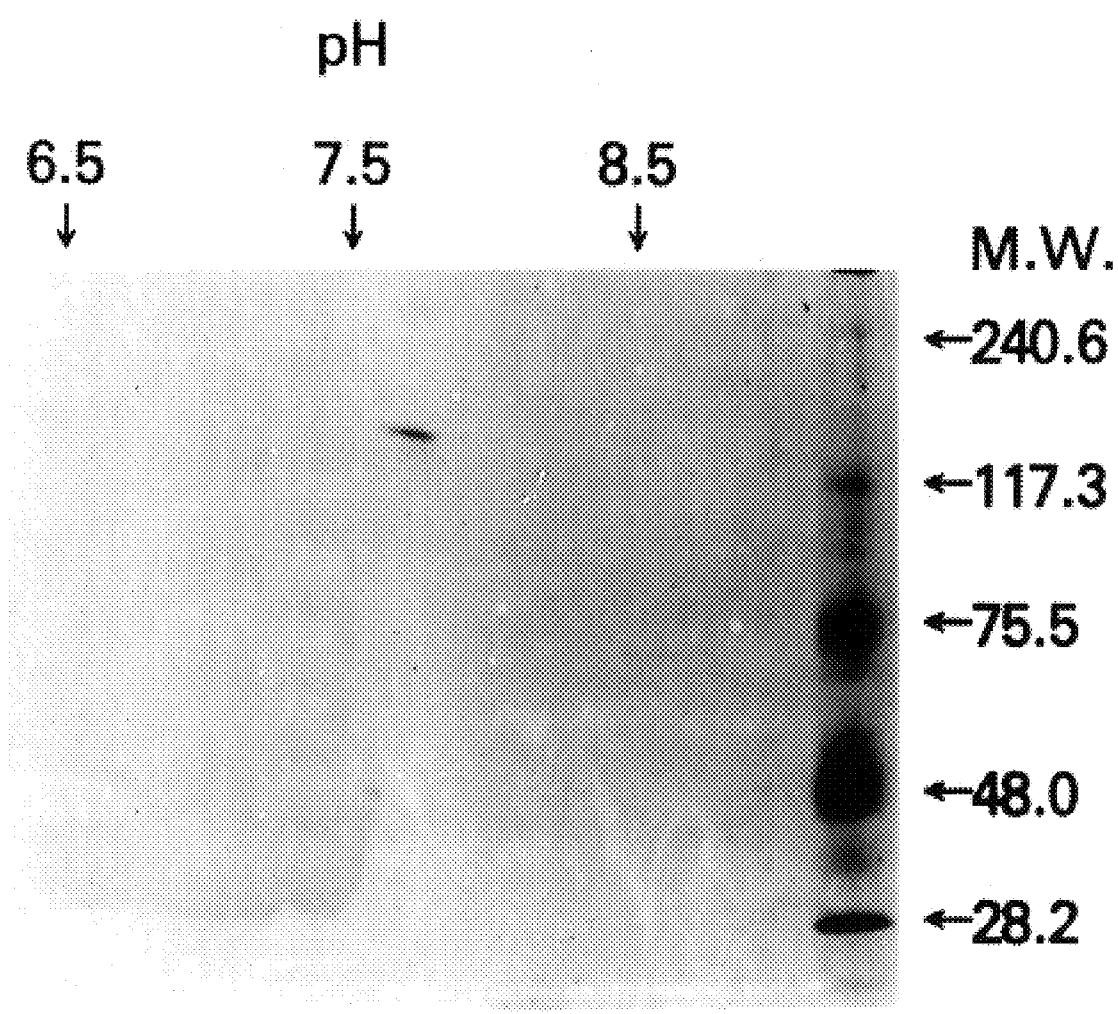
FIG. 7. Two-dimensional gel electrophoresis of ATX. Purified ATX (FIG. 6, Panel C) was subjected to non-equilibrium isoelectric focusing (5 hr. at 500v), then applied to a 7.5% SDS-polyacrylamide gel for the second dimension. The pH separation which resulted was measured in 0.5 cm samples of concurrently run tube gels and is shown at the top. Molecular weight standards for the second dimension are shown on the right. This analysis reveals a single component with pI=7.7±0.2 and $M_r$=120,000.

Two dimensional gel electrophoresis of the purified protein (FIG. 7) revealed a single predominant band. The band slopes downward slightly toward the basic side of the gel in a manner that is characteristic of glycosylated proteins. A basic pI of 7.7±0.2 was essentially the same whether the isoelectric focusing was run under non-equilibrium conditions (5 hr.) or was allowed to go to equilibrium (17 hr.).

Figure 8:
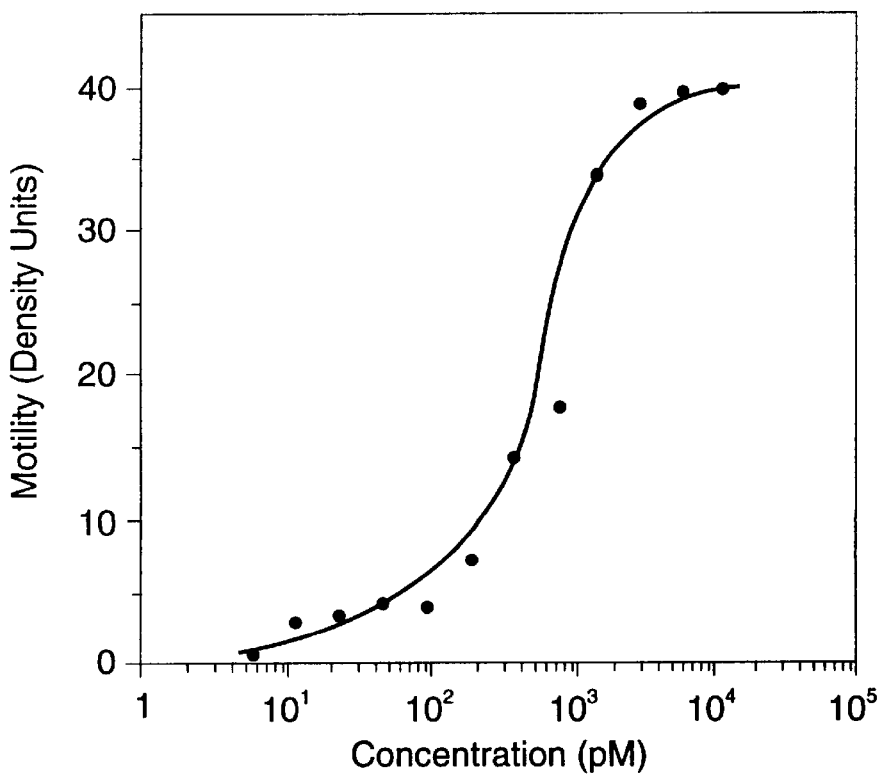
FIG. 8. Dilution curve of ATX. Purified ATX (FIG. 6, Panel C) was serially diluted and tested for motility-stimulating activity. The result, with unstimulated background motility subtracted out, shows that activity is half-maximal at ~500 pM ATX.
Figure 9:
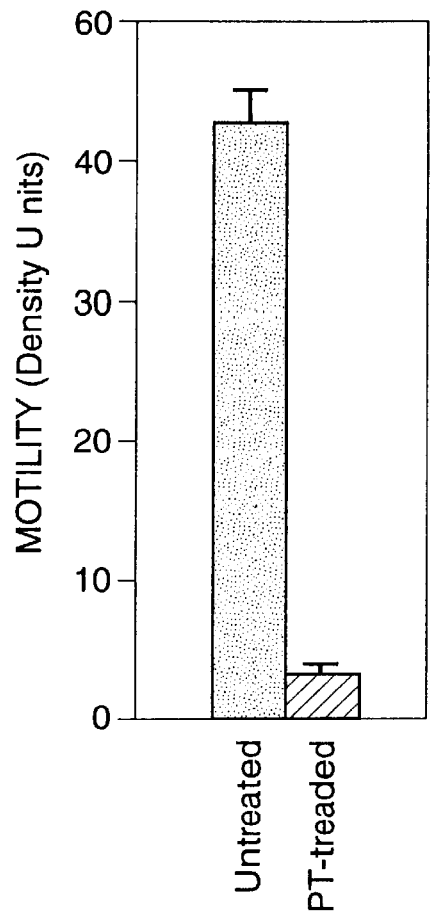
FIG. 9. Pertussis toxin (PT) sensitivity of ATX. A2058 cells were pre-treated for 1 hr. prior to the start of the motility assay with 0.5 μg/ml PT in 0.1% BSA-DMEM or with 0.1% BSA-DMEM alone (for untreated control). The motility activity stimulated by purified ATX (FIG. 6, Panel C) was then assessed for the two treatment groups. The result, expressed as cells/HPF±S.E.M. with unstimulated background motility subtracted out, reveals profound inhibition of PT-treated cells (hatched) compared to untreated cells (solid). PT had no effect on cell viability. S.E.M.'s were <10%.

A dilution curve of the purified protein is shown in FIG. 8. The protein is active in the picomolar range and 1 unit of activity appears to correspond to a concentration of 400–600 picomolar (or approximately 10 fmol of ATX/Boyden chamber well). When dilutions were begun at higher concentrations of ATX, the resultant curve showed a broad plateau with down-regulation at the highest concentrations. The motility response to purified autotaxin is highly sensitive to pertussis toxin (hereinafter referred to as "PT") (Table 2 and FIG. 9) with approximately 95% inhibition of activity at 0.5 µg/ml PT.

TABLE 2

Effect of Pertussis Toxin (PT) on Autotaxin-stimulated motility

| | A2058 Motility Response (density units[1]) | |
|---|---|---|
| | control cells[2] | Pertussis toxin-treated cells[3] |
| Condition medium[4] | 60.3 | 0.4 |
| Purified Autotaxin | 38.5 | 0.0 |

[1] Chemotaxis quantitated by motility assay (Stracke, et al., 1978).
[2] A2058 cell suspended at 2 × 10⁶ cells/ml in DMEM supplemented with 1 mg/ml bovine serum and rocked at room temperature for 1 hr.
[3] As control with 0.5 µg/ml pertussis toxin.
[4] Prepared by adding DMEM without phenol red supplemented with 0.1 mg/ml bovine serum albumin to subconfluent flasks of A2058 cells. The medium was harvested after 2 days incubation at 37° C. in a humidified atmosphere and concentrated 25–30 fold using an Amicon ultrafiltration assembly with a YM-30 membrane.

Figure 10:
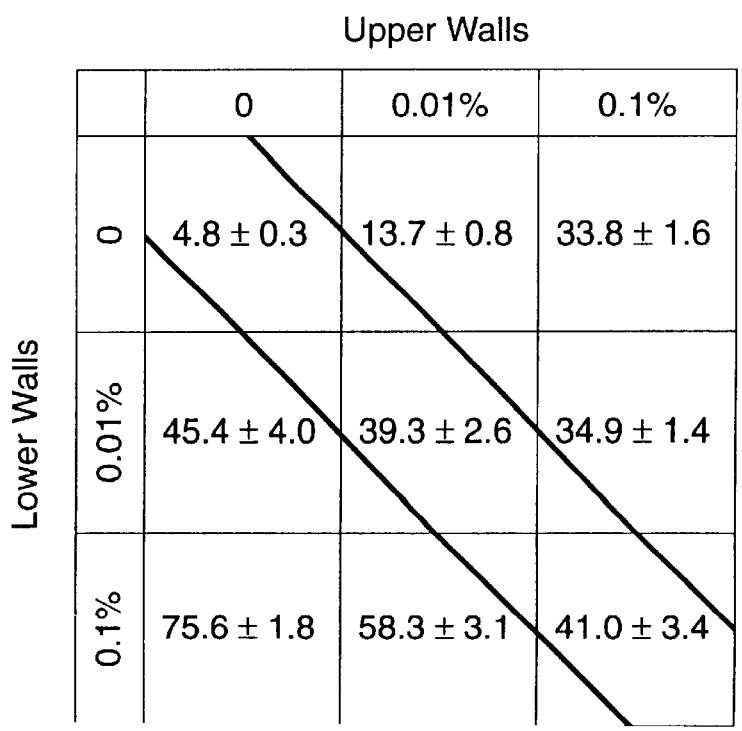
FIG. 10. Checkerboard analysis of ATX-stimulated motility. Varying dilutions of autotaxin were added to the upper chamber with the cells and/or to the lower chamber, as shown. Motility response, expressed as cells/HPF±S.E.M., was assessed for each point in the checkerboard.

Checkerboard analysis was performed to assess the random (chemokinetic) versus the directed (chemotactic) nature of the motility response to ATX. Chambers were assembled with different concentrations of ATX above and below the filter, using ATX purified through the weak anion exchange fractionation step. Squares below the diagonal reflect response to a positive gradient, squares above reflect response to a negative gradient, and squares on the diagonal reflect random motility in the absence of a gradient. ATX stimulates both chemotactic and chemokinetic responses (FIG. 10), with chemotactic responses as high as fifteen-fold above background and chemokinesis as high as eight-fold above background.

Amino acid analysis after complete acid hydrolysis was used to quantitate purified protein. This hydrolysis was carried out on protein excised from a polyacrylamide gel and presumed to be pure. The analysis indicated that 2.7 nmol of protein was present after fractionation on the molecular sieve. After fractionation by strong anion exchange chromatography, approximately 300 pmol remained. The results of the analysis are shown in Table 3.

TABLE 3

AMINO ACID COMPOSITION OF AUTOTAXIN
(CYS and TRP were not determined in this analysis)

| Amino Acid | Residues/100 |
|---|---|
| ASX | 12.5 |
| THR | 6.0 |
| SER | 5.7 |
| GLX | 9.4 |
| PRO | 7.4 |
| GLY | 7.0 |
| ALA | 3.9 |
| VAL | 6.7 |
| MET | 1.2 |
| ILE | 4.3 |
| LEU | 9.0 |
| TYR | 5.2 |
| PHE | 5.2 |
| HIS | 3.8 |
| LYS | 7.4 |
| ARG | 5.4 |

Example 3

ATX Degradation and Determination of Amino Acid Sequence

Figure 11:
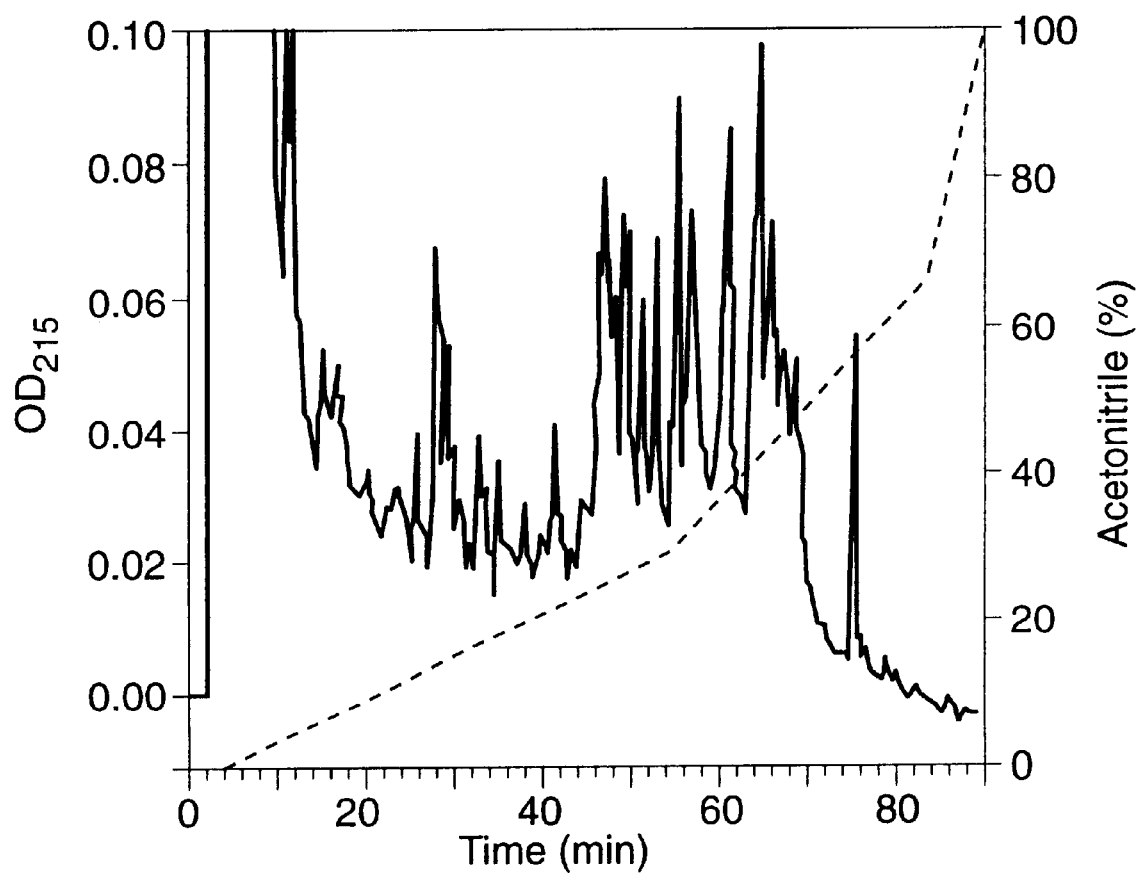
FIG. 11. Purification of ATX peptides on HPLC. ATX, purified to homogeneity by strong anionic exchange chromatography, was sequentially digested by cyanogen bromide, subjected to reduction and pyridylethylation, and digested by trypsin. The resulting peptides were purified on an Aquapore RP300 C-8 reverse phase column using a (0–70)% acetonitrile gradient in 0.1% trifluoroacetic acid (—). The absorbance was monitored at 215 nm (_) and peaks were collected. Seven peaks, chosen at random for N-terminal amino acid sequence analysis, are shown with appropriate numbers.

Attempts to obtain N-terminal sequence information from purified ATX repeatedly proved futile. The purified protein was therefore, sequentially digested and the resulting peptides fractionated by reverse phase chromatography. The results are shown in FIG. 11. Multiple sharp peaks including clusters at both the hydrophilic and hydrophobic ends of the gradient are seen.

Several of these peptide peaks were chosen randomly for Edman degradation and N-terminal amino acid sequence analysis. Seven of the eight peaks (shown in FIG. 11) chosen gave clear single sequence information as seen in Table 4. Using material from a separate digestion and purification, the remaining four sequences were also obtained.

Separate sense and antisense oligonucleotide probes were synthesized according to the fragment sequences of Table 4 by methods known to one skilled in the art. Representative probes are shown in Table 5.

TABLE 4

Peptide sequences for Autotaxin.

| PEPTIDE NO. | AMINO ACID SEQUENCE | SEQ ID: NO: | NAME |
|---|---|---|---|
| 1. | WHVA | SEQ ID NO: 1 | ATX 18 |
| 2. | PLDVYK | SEQ ID NO: 2 | ATX 19 |
| 3. | YPAFK | SEQ ID NO: 3 | ATX 20 |
| 4. | QAEVS | SEQ ID NO: 4 | ATX 24 |
| 5. | PEEVTRPNYL | SEQ ID NO: 5 | ATX 29 |
| 6. | YDVPWNETI | SEQ ID NO: 6 | ATX 47 |
| 7. | VPPFENIELY | SEQ ID NO: 7 | ATX 48 |
| 8. | GGQPLWITATK | SEQ ID NO: 8 | ATX 100 |
| 9. | VNSMQTVFVGY-GPTFK | SEQ ID NO: 9 | ATX 101 |
| 10. | DIEHLTSLDFFR | SEQ ID NO: 10 | ATX 102 |
| 11. | TEFLSNYLTNVDD-ITLVPETLGR | SEQ ID NO: 11 | ATX 103 |
| 12. | QYLHQYGSS | SEQ ID NO: 26 | ATX 37 |
| 13. | VLNYF | SEQ ID NO: 27 | ATX 39 |
| 14. | YLNAT | SEQ ID NO: 28 | ATX 40 |
| 15. | HLLYGRPAVLY | SEQ ID NO: 29 | ATX 41 |
| 16. | SYPEILTPADN | SEQ ID NO: 30 | ATX 44 |
| 17. | XYGFLFPPYLSSSP | SEQ ID NO: 31 | ATX 53 |
| 18. | TFPNLYTFATGLY | SEQ ID NO: 32 | ATX 59 |
| 19. | VNVISGPIFDYDYDGLH DTEDK | SEQ ID NO: 33 | ATX 104 |

Peptide numbers 1–7 refer to peaks numbered in FIG. 11. Peptide numbers 12–18 refer to peptides purified from the preparation which yielded peptide numbers 1–7. Peptides 8–11 and 19, are from a separate purification, not shown in FIG. 11.

X refers to potentially glycosylated residues.

TABLE 5

Oligonucleotides synthesized from peptide sequences of autotaxin (ATX). The number of the oligonucleotide corresponds to the ATX peptide number as per Table 4. The final letter suffix distinguishes whether the oligonucleotide is a sense (S) or antisense (A) sequence.

| Oligo | Sequence | SEQ ID NO: |
|---|---|---|
| A-18A | GTT-GGC-AGC-NAC-RTG-CCA | SEQ ID NO: 12 |
| A-18S | TGG-CAY-GTN-GCT-GCC-AAC | SEQ ID NO: 13 |
| A-20A | CTT-GAA-GGC-AGG-GTA | SEQ ID NO: 14 |
| A-20S | TAY-CCT-GCN-TTY-AAG | SEQ ID NO: 15 |
| A-29A | GGT-NAC-YTC-YTC-AGG | SEQ ID NO: 16 |
| A-29S | CCT-GAR-GAR-GTN-ACC | SEQ ID NO: 17 |
| A-47A | NGT-NGC-RTC-RAA-TGG-CAC-RTC | SEQ ID NO: 18 |
| A-47S | GAY-GTG-CCA-TTY-GAY-GCN-ACN | SEQ ID NO: 19 |
| A-48A | GTT-DAT-RTT-STC-RAA-TGG-GGG | SEQ ID NO: 20 |
| A-48S | CCC-CCA-TTT-GAG-AAC-ATC-AAC | SEQ ID NO: 21 |
| A-100A | CTT-NGT-NGC-NGT-DAT-CCA-NAR-GGG-YTG-GCC-GCC | SEQ ID NO: 22 |
| A-100S | GGC-GGC-CAR-CCC-YTN-TGG-ATH-ACN-GCN-ACN-AAG | SEQ ID NO: 23 |
| A-101A | CTT-RAA-GGT-GGG-GCC-RTA-GCC-CAC-RAA-GAC-TGT-YTG-CAT | SEQ ID NO: 24 |
| A-101S | ATG-CAR-ACA-GTC-TTY-GTG-GGC-TAY-GGC-CCC-ACC-TTY-AAR | SEQ ID NO: 25 |

Example 4

Antipeptide Antibodies

Rabbits were injected with ATX-101 (SEQ ID NO:10) which had been cross-linked to bovine serum albumin. Antisera from these rabbits was subjected to salt precipitation followed by purification using affinity chromatography with Affi-Gel 10 beads covalently linked to the peptide, ATX-101 (SEQ ID NO:10). This affinity purified antibody reacted with the partially purified protein on immunoblots. This same antibody has been used to perform immunohistochemical stains on human tissue.

Example 5

Enzymatic Deglycosylation of ATX

Purified ATX that was to be treated with peptide N-glycosidase F (PNGase F) was first dialyzed into 0.2M sodium phosphate, 10% (v/v) ethylene glycol pH 7.0, using Centricon-30 ultrafiltration tubes. Varying concentrations of PNGase F were added to the ATX and incubated 16–18 hr. at 37° C. Complete digestion appeared to occur at concentrations of enzyme above 30 mU/ml (where 1 U converts 1 mmol of substrate/min). For comparison, the experiments were repeated in the presence of 0.1M β-mercaptoethanol or 0.1% (w/v) SDS plus 0.5% (v/v) Nonidet-P40. ATX that was to be treated with neuraminidase or O-glycosidase was dialyzed into 20 mM sodium phosphate, 0.1 M calcium acetate, and 10% (v/v) ethylene glycol (pH 7.2). Neuraminidase was added to a final concentration of 2 U/ml. For treatment with neuraminidase alone, this mixture was incubated 16–18 hr at 37° C. Since O-glycosidase requires the removal of terminal sialic acid residues for efficient deglycosylation, ATX was pre-incubated with neuraminidase for 30–125 mU/ml and incubated 16–18 hr. at 37° C. The treated ATX was then dialyzed into 50 mM Tris with 20% ethylene glycol for storage at 5%C.

Treatment of ATX with N-Glycosylation Altering Agents

A2058 cells were split into four 150 $cm^2$ flasks and incubated until just subconfluent in DMEM supplemented with 10% fetal calf serum. The medium was then replaced with fresh 10% FCS/DMEM to which had been added DPBS for control, 1 mM dMAN, 1 mM NMdNM, or 10 mM (1.7 mg/ml) Swn. Concentrations of these pharmacological agents were similar to those previously described as inhibiting N-glycan processing enzymes in melanoma cells (Seftor, et al. 1991; Dennis, et al. 1990) as well as carcinoma cells (Ogier, et al. 1990). On the next day, each flask was washed twice with Dulbecco's phosphate buffered saline with calcium ("DPBS") then 20 ml of Dulbecco's minimum essential medium ("DMEM") supplemented with 0.01% (w/v) bovine serum albumin ("BSA") was added. The same concentration of each agent was added to the appropriate equilibrated flask and incubated for ~24 hr, after which the medium from each treatment group was collected, concentrated, washed into DPBS and stored at 5° C.

Cells from each flask were trypsinized and counted. There was no loss of viability or reduced cell number in any of the treatment groups compared to control cells.

Effect of PNGase F on ATX

ATX binds to concanavalin A ("Con A") agarose beads and is eluted with buffer containing 0.5M methyl α-D-mannopyranoside, indicating that ATX is likely to contain mannose residues. Such mannose sugar residues are most characteristic of N-linked oligosaccharides. In order to verify that ATX contained asparagine-linked oligosaccharides, we treated it with the endoglycosidase, PNGase F, which cleaves high mannose, hybrid, and complex N-linked oligosaccharides at the asparagine residue.

Partially purified ATX was treated with 60 mU/ml of enzyme under a variety of increasingly denaturing conditions and then separated by polyacrylamide gel electrophoresis (FIG. 16). Lane 1 shows untreated material; the 125 kDA band (arrow) is autotaxin. When this material is treated overnight with PNGase F under very mild conditions, the size of the 125 kDa band decreases to ~100–105 kDa. Addition of 0.1M b-mercaptoethanol (Lane 2) or 0.5% Nonidet-P40 (lane 3) to the ATX sample has no effect on the size of the resultant protein band. Even complete denaturation of ATX of boiling the sample for 3 min in 0.1% SDS with (lane 5) or without (lane 4) β-mercaptoethanol, followed by addition of 0.5% Nonidet-P40 to maintain enzymatic activity, has no effect on the final size of deglycosylated protein, indicating that the deglycosidation reaction was complete even under mild conditions.

Because these results showed that ATX contained N-linked oligosaccharide groups, it became important to see if these sugar moieties were necessary for stimulation of motility. The partially purified ATX sample was treated with varying concentrations of PNGase F (0.1 to 60 mU/ml) under mild, non-denaturing conditions. Analysis of the resulting digest by polyacrylamide gel electrophoresis is shown in FIG. 17A. As this figure shows, the digestion was incomplete using from 0.1 to 10 mU/ml of enzyme and resulted in a smear of protein between 100–125 kDa. However, at higher concentrations of enzyme, cleavage of N-linked oligosaccharides from ATX appears to be complete. When these different digestion products were compared for their capacity to stimulate motility (FIG. 17B), there was no significant difference between groups.

Example 6

Cloning the 3' End of Autotaxin (4C11)

Figure 12:
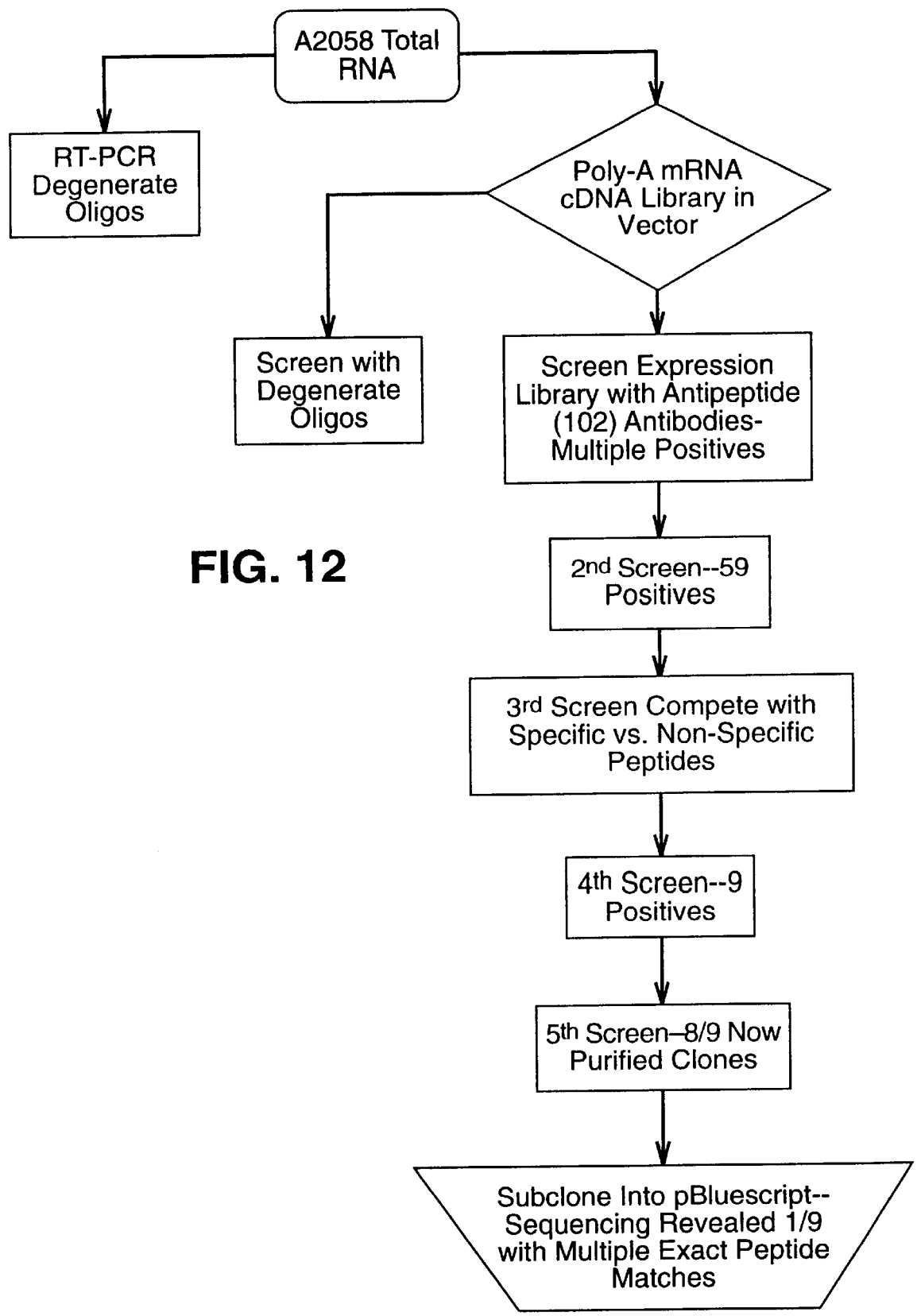
FIG. 12. Cloning Strategy, schematically depicted.

ATX is active in picomolar to nanomolar concentrations and is synthesized in very small concentrations by A2058 cells. As might be expected, the cDNA clone was relatively rare, requiring various strategies and multiple library screenings in order to identify it (FIG. 12). Attempts to utilize degenerate oligonucleotides deduced from known peptide sequences were unsuccessful—whether we used the oligo nucleotides for screening cDNA libraries or for reverse transcription of mRNA followed by amplification with the polymerase chain reaction (RT/PCR). We then utilized an affinity-purified anti-peptide ATX-102 antibodies to screen an A2058 expression library.

These anti-peptide antibodies were generated by methods well established in the art and described previously with slight modification (Wacher, et al., 1990). In brief, the previously identified peptide, ATX-102 (Stracke, et al., 1992), was synthesized on a Biosearch 9600 peptide synthesizer. It was then solubilized in 1× PBS containing 20% (v/v) DMSO and conjugated to the protein carrier, bovine serum albumin (BSA), with glutaraldehyde. For the first injection into New Zealand white rabbits, the BSA-peptide conjugate was emulsified with complete Freund's adjuvant and injected subcutaneously. For subsequent injections, the BSA-peptide conjugate was emulsified with incomplete Freund's adjuvant. The resultant antiserum was heat-inactivated at 56° C. for 30 min. Immunoglobulins were precipitated out in 47% saturated ammonium sulfate, then redissolved and dialyzed into PBS. Antibodies were adsorbed onto peptide-conjugated Affi-Gel 10 resin (made using the BioRad protocol), eluted with 0.1N acetic acid, and neutralized with 2M Tris-HCl, pH 8. The resulting affinity-purified antibodies were dialyzed into DPBS, concentrated, aliquotted, and stored at −20° C. The antibodies were found to recognize a 125 kDa protein on immunoblots of partially purified A2058 conditioned medium and to preferentially stain some breast carcinoma cells compared to normal breast using immunohistochemical techniques.

An A2058 cDNA library was prepared by purifying poly-A purified mRNA from the cells then size-selecting mRNA >1000 bp for the preparation of cDNA. The cDNA inserts were placed into λgt11 directionally, using the ProMega cDNA kit using standard methods well-established in the field. LE 392 cells were infected with the λgt11 and plaques were transferred onto nitrocellulose membranes by overnight incubation at 37° C. The antibody was incubated with the membranes in blocking buffer for 2 hr at room temperature, using approximately twice the concentration of antibody which gave a strong response on Western blot analysis. Secondary antibody was goat anti-rabbit immunoglobulin, and the blot was developed colorimetrically with 4-chloro-1-naphthol.

Positive clones were confirmed by antibody competition with specific peptides but not unrelated peptides. Using this technique and multiple subclonings, we obtained a partial cDNA clone of the autotaxin gene, which we called 4C11. The 4C11 insert was removed from λgt11 by restriction enzyme digests and subcloned into pBluescript for sequencing by standard Sanger techniques (Sanger, et al., 1977). The 4C11 clone contained bases, including the poly-adenylated tail and the AATAAA adenylation signal locus, i.e., it contained the 3' terminus of the gene. It also included a 627 base open reading frame. Database analysis of this nucleotide sequence revealed that it is unique. The predicated amino acid sequence for 4C11 is 209 amino acids long with exact matches for 7 previously identified ATX peptides: (ATX-20, ATX-34, ATX-102, ATX-104, ATX-204, ATX-215, and ATX-244).

Example 7

Cloning the 5' Terminus of ATX

Database analysis of the 3' terminus of the ATX gene demonstrated a novel protein. However, we have found an interesting homology that has helped to guide us in exploring its function. ATX had a 45% amino acid identity and a 57% nucleotide identity with PC-1, a marker of B cell activation found on the surface of plasma cells. Using the PC-1 protein sequence as a guide, we found that ATX peptide homologies were scattered throughout the length of the protein. The only exception was the far amino terminus of PC-1, which includes the transmembrane and intracellular domains, and which had no homologies. Knowing approximate localization of the ATX peptides along the length of ATX, we then amplified different segments of ATX by the PCR (FIG. 13). These amplified segments of DNA were then subcloned into plasmids utilizing the TA Cloning kit of ProMega. The PCR amplified DNA could then be sequenced using standard Sanger sequencing techniques (Sanger, et al., 1977).

Cloning of Full Length ATX Gene

A reverse transcriptase reaction was performed using total or oligo-(dT) purified RNA from A2058 or N-tera 2D1 cells as template and an anti-sense primer from the 5' end of 4C11 (GCTCAGATAAGGAGGAAAGAG) (SEQ ID NO:55). This was followed by one or two PCR amplification of the resultant cDNA using the commercially available kit from Perkin-Elmer and following manufacturer's directions. These PCR reactions utilized nested antisense primers from 4C11 (GAATCCGTAGGACATCTGCTT (SEQ ID NO:56) and TGTAGGCCAAACAGTTCTGAC) (SEQ ID NO:57) as well as degenerate, nested sense primers deduced from ATX peptides: ATX-101 (AAYTCIATGCARACIGTITTYGTIG (SEQ ID NO:58) and TTYGTIGGITAYGGICCIACITTYAA) (SEQ ID NO:59), ATX-103 (AAYTAYCTIACIAAYGTIGAYGAYAT (SEQ ID NO:60) and GAYGAYATIACICTIGTICCIGGIAC) (SEQ ID NO:61), or ATX-224 (TGYTTYGARYTICARGARGCIGGICCICC) (SEQ ID NO:62). The amplified DNA was then purified from a polyacrylamide gel using standard procedures and ligated into the pCR™ plasmid using the TA cloning kit (Invitrogen Corporation) according to manufacturer's directions.

The 5' RACE kit was utilized to extend the 5' end of ATX cDNA using total RNA from N-tera 2D1 as template and previously obtained sequence as primer (GCTGTCTTCAAACACAGC) (SEQ ID NO:63). The 5' end of the A2058 synthesized protein was obtained by using previously obtained sequence as primer (CTGGTGGCTGTAATCCATAGC) (SEQ ID NO:64) in a reverse transcriptase reaction with total A2058 RNA as template, followed by PCR amplification utilizing the 5' end of N-tera 2D1 sequence as sense primer (CGTGAAGGCAAAGAGAACACG) (SEQ ID NO:65) and a nested antisense primer (GCTGTCTTCAAACACAGC) (SEQ ID NO:63). A2058 DNA encoding ATX is set forth in a SEQ ID NO:68 and the amino acid sequence is provided in SEQ ID NO:69.

DNA sequencing: DNA sequencing was performed using dideoxy methodology (Sanger, et al. 1977) and ($^{35}$S)dATP (Du Pont, New England Nuclear).

We have found one region between the 5' end of the 4C11 and the ATX peptide designated ATX-101, also referred to as the "hot spot". This region has been sequenced five times with different sequences found each time. The hot spot appears to be located within the region from approximately nucleotide 1670 to 1815. The consensus sequence is represented by amino acids position 559 through 604. Variations found include DNA sequence that results in single and multiple amino acid insertions. One sequence had a stop codon in this region and may have represented an intron. This region has been found to be variable in forms of ATX.

Example 8

Cloning ATX in a Human Teratocarcinoma Cell Line

The fact that ATX is present in other cancer cells was confirmed by sequence information from N-tera 2D1, a human teratocarcinoma cell line. For these cells, a prepared cDNA library in λgt10 was amplified and the cDNA inserts were extracted. Using oligonucleotide primers based on known A2058 ATX sequence, DNA segments were amplified by PCR. The DNA segments were then subcloned into plasmids and sequenced as for A2058. We have 3104 bp DNA sequence for N-tera ATX (SEQ ID NO:66) and smaller portions thereof. This includes an open reading frame that codes for a putative protein containing 861 amino acids (SEQ ID NO:67) and smaller portions thereof. Like the A2058 ATX, the N-tera 2D1 sequence has homologies for multiple ATX peptides (FIG. 15). Sequence homology between the A2058 and N-tera 2D1 cells is approximately 99%.

Example 9

Cloning 5' End of ATX in Human Normal Liver

The 5' end of ATX has proven difficult to obtain from either tumor cell line to date. Normal human liver mRNA was therefore amplified using the 5' RACE kit (Clontech) with known sequence from A2058 ATX as antisense primer. A DNA segment was obtained and has been sequenced. This segment codes for 979 amino acids, including an initiating methionine (SEQ ID NO:38). The putative protein sequence also includes a 20 amino acid transmembrane domain which is different from the tumor ATX's (SEQ ID NO:54), as shown in Table 7. Both tumorous forms of ATX apparently lack a transmembrane region and are instead secreted proteins.

TABLE 7

Nucleotide and Amino Acid Sequences Encoding Liver ATX Amino Terminus containing the Transmembrane region Protein Sequence (SEQ ID NO: 54)

Met Ala Arg Arg Ser Ser Phe Gln Ser Cys Gln Asp Ile Ser Leu Phe Thr Phe Ala Val Gly Val Asn Ile Cys Leu Gly Phe Thr Ala His Arg Ile Lys Arg Ala Glu Gly Trp
DNA Sequence (SEQ ID NO: 53)

ATGGCAAGGA GGAGCTCGTT CCAGTCGTGT CAAGATATAT CCCTGTTCAC
TTTTGCCGTT GGAGTCAATA TCTGCTTAGG ATTCACTGCA CATCGAATTA
AGAGAGCAGA AGGATGG

Example 10

Domains of ATX

Searches of protein databases (Pearson, et. al. 1988) confirmed that the homology between ATX and PC-1 was present throughout the length of the extracellular portion of the molecules (Buckley, et. al., 1990; Funakoshi, et. al. 1992). There is a 45% amino acid identity and a 64% similarity between the 2 protein sequences (FIG. 18). For the cDNA sequence, the identity is ~57%.

These proteins share several interesting properties and domains (FIG. 19). Both have a number of potential N-linked glycosylation sites: four for ATX (Asn54, Asn463, Asn577, Asn859) and nine for PC-1. Both have adjacent somatomedin B domains near the amino end of the extracellular domain. This somatomedin B domain is a cysteine-rich region containing 3 presumed cystine cross-linkages. ATX has 33 Cys residues and PC-1 has 37; 30 of these Cys residues are identical in placement. Both proteins also contain the loop region of an EF hand (Buckley, et. al. 1990; Kretsinger, 1987). In addition, both proteins have a transmembrane/signal peptide region with a short intracellular peptide, common in ectoenzymes (Maroux, 1987). However, the amino acid identity between ATX and PC-1 in the intracellular and transmembrane regions is only 11%.

Finally, both proteins have a region homologous to the bovine intestinal phosphodiesterase enzymatic domain with conversation of the threonine that is thought to act as the intermediate phosphate binding site (Culp, et al. 1985). PC-1 has been demonstrated to have phosphodiesterase type I, nucleotide pyrophosphatase, and threonine-specific kinase enzymatic activities (Rebbe, et al. 1991; Oda, et al. 1991). In order to test whether purified ATX had type I phosphodiesterase activity, samples were incubated with p-nitrophenyl thymidine-5'-monophosphate at pH 8.9 for 30 min. Samples were assayed in a 100 µl volume containing 50 mM Tris-HCl, pH 8.9 and 5 mM p-nitrophenyl thymidine-5'-monophosphate. After a 30 minute incubation at 37° C. the reactions were terminated by addition of 900 ml 0.1N NaOH and the amount of product formed was determined by reading the absorbance at 410 nm. ATX was found to hydrolyze the p-nitrophenyl thymidine-5'-monophosphate (Razzell, 1963) at a rate of 10 pmol/ng/min, a reaction rate similar to that reported for PC-1 (Oda, et al. 1993).

REFERENCES

Atnip, K. D., et al. (1987) *Biochem. Biophys. Res. Comm.* 146, 996–1002
Buckley, M. F., Loveland, K. A., McKinstry, W. J., Garson, O. M. and Goding, J. W. (1990) *J. Biol. Chem.* 265, 17506–17511
Culp, J. S., Blytt, H. J., Hermodson, M. and Butler, L. G. (1985) *J. Biol. Chem.* 260, 8320–8324
Dennis, J. W., Koch, K., Yousefi, S. and VanderElst, I. (1990) *Cancer Res.* 50, 1867–1872
Funakoshi, I., Kato, H., Horie, K., Yano, T., Hori, Y., Kobayashi, H., Inoue, T., Suzuki, H., Fukui, S., Tsukahara, M., Kajii, T. and Yamashina, I. (1992) *Arch. Biochem. Biophys.* 295, 180–187
Gospodarowicz, D. (1984) *Proc. Natl. Acad. Sci. USA* 81, 6963–6967
Guirguis, R., et al. (1987) *Nature* 329, 261–263
Jouanneau, J., et al. (1991) *Proc. Natl. Acad. Sci. USA* 88, 2893–2897
Kahan, B. W. et al., (1987) *Cancer Res.* 47, 6324–6328
Kretsinger, R. H. (1987) *Cold Spring Harbor Symp. Quant. Bio.* 52, 499–510
Kohler and Milstein, (1975) *Nature* 256:495–497
Kohn, E. C., et al. (1990) *Int. J. Cancer* 46, 287–292
Laemmli U. K. (1970) *Nature* 227, 680–685
Landsteiner, *Specificity of Serological Reactions* (Dover Publications, New York, 1962)
Liotta, L. A., et al. (1986) *Proc. Natl. Acad. Sci. USA* 83, 3302–3306
Liotta, L. A., et al. (1988) *Cancer Surveys* 7, 631–652
Maciag, T., et al. (1984) *Sci.* 225, 932–935
Maroux, S. (1987) In A. J. Kenny and A. J. Turner (eds.) *Mammalian Ectoenzymes,* Elsevier Science Publishers B. V., Amsterdam, The Netherlands, 15–45
McCarthy, J. B., et al. (1984) *J. Cell Biol.* 98, 1474–1480 Microbiology, Hoeber Medical Division (*Harper and Row,* 1969)
Nabi, I. R., et al. (1990) *Cancer Res.* 50, 409–414
Neuhoff, V., et al. (1988) *Electrophoresis* 9, 255–262
Oda, Y., Kuo, M.-D., Huang, S. S. and Huang, J. S. (1991) *J. Biol. Chem.* 266, 16791–16795
Oda, Y., Kuo, M.-D., Huang, S. S. and Huang, J. S. (1993) *J. Biol. Chem.* 268, 27318–27326
O'Farrell, P. H. (1975) *J. Biol. Chem.* 250, 4007–4021
O'Farrell, P. H., et al. (1977) *Cell* 12, 1133–1142
Ogier-Denis, E., Trugnan, G., Sapin, C., Aubery, M. and Codogno, P. (1990) *J. Biol. Chem.* 265, 5366–5369
Ohnishi, T., et al. (1990) *J. Neurosurg.* 73, 881–888
Pearson, W. R., et al. (1988) *Proc. Natl. Acad. Sci. USA* 85, 2444–2448
Razzell, W. E. (1963) *Methods Enzymol.* 6, 236–258
Rebbe, N. F., Tong, B. D., Finley, E. M. and Hickman, S. (1991) *Proc. Natl. Acad. Sci. USA* 88, 5192–5196
Rosen, E. M. et al., (1989) *In Vitro Cell Devel. Biol.* 25, 163–173
Rosen, E. M., et al. (1990) *Proc. Soc. Exp. Biol. Med.* 195, 34–43
Ruff, M., et al. (1985) *Clin. Immunol. Immunopath.* 37, 387–396
Sanger, F. et al. (1977) *Proc. National Acad. Sci. USA.* 74, 5463–5467
Schnor, S. L., et al. (1988) *J. Cell Sci.* 90, 391–399
Seftor, R. E. B., Seftor, E. A., Grimes, W. J., Liotta, L. A., Stetler-Stevenson, W. G., Welch, D. R. and Hendrix, M. J. C. (1991) *Melanoma Res.* 1, 43–54
Silletti, S., et al. (1991) *Cancer Res.* 51, 3507–3511
Singer, S. J. and Kupfer, A. (1986) *Ann. Rev. Cell Biol.* 2, 337–365
Stites et al., editors, *Basic and Clinical Immunology,* (Lange Medical Publications, Los Altos, Calif., Fourth edition)
Stoker, M., et al. (1987) *Nature* 327, 239–242
Stone, M, et al. (1989) A *Practical Guide to Protein and Peptide Purification for Microsequencing* (Matsudaira, P. T., ed.) pgs. 33–47, Academic Press, N.Y.
Stracke, M. L. et al., *Biochem. Biophys. Res. Comm.* 153, 1076–1083
Stracke, M. L., et al. (1978) *Biochem. Biophys. Res. Comm.* 146, 339–345
Stracke, M. L., et al. (1987) *Biochem. Biophys. Res. Comm.* 147, 339–345
Stracke, M. L., et al. (1988) *Biochem. Biophys. Res. Comm.* 153, 1076–1083
Tamm, I., et al., (1989) *J. Exp. Med.* 170, 1649–1669
Taraboletti, G., (1987) *J. Cell Biol.* 105, 2409–2415
Todaro, G. J., et al. (1980) *Proc. Natl. Acad. Sci. USA* 77, 5258–5262
Van Snick, J. (1990) *Ann. Rev. Immunol.* 8, 253–278
Wang, J. M., et al. (1990) *Biochem. Biophys. Res. Comm.* 169, 165–170
Watanabe, H., et al. (1990) *J. Cell Biol.* 111, 2097–2108
Watanabe, H., et al. (1991) *J. Biol. Chem.* 266, 13442–13448
Weidner, K. M., et al. (1990) *J. Cell. Biol.* 111, 2097–2108
Williams et al., *Methods in Immunology and Immunochemistry,* Vol. 1 (Academic Press, New York, 1967)
Yoshimura, T. (1987) *Proc. Natl. Acad. Sci. USA* 84, 9233–9237

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the present invention and appended claims.

What is claimed is:

1. An isolated autotaxin polypeptide comprising an amino acid sequence selected from the group consisting of SEQ ID NO:2, SEQ ID NO:5 through SEQ ID NO:11, SEQ ID NO:26, SEQ ID NO:29 through SEQ ID NO:34, SEQ ID NO:36, SEQ ID NO:38 through SEQ ID NO:52, SEQ ID NO:67 and SEQ ID NO:69.

2. An isolated autotaxin polypeptide comprising an amino acid sequence selected from the group consisting of the SEQ ID NO:1 through SEQ ID NO:11, SEQ ID NO:26 through SEQ ID NO:34, SEQ ID NO:36, SEQ ID NO:38 through SEQ ID NO:52, SEQ ID NO:67 and SEQ ID NO:69.

3. An isolated polypeptide comprising an amino acid sequence corresponding to autotaxin, wherein said polypeptide is selected from the group consisting of SEQ ID NO:34, SEQ ID NO:36, SEQ ID NO:38, SEQ ID NO:67 and SEQ ID NO:69.

4. A polypeptide according to claim 2, bound to a solid support comprising an amino acid sequence corresponding to autotaxin.

5. A recombinant autotaxin polypeptide according to claim 2.

* * * * *

SEQUENCE LISTING (1) GENERAL INFORMATION:

(iii) NUMBER OF SEQUENCES: 69

(2) INFORMATION FOR SEQ ID NO:1:

(i) SEQUENCE CHARACTERISTICS:
        (A) LENGTH: 5
        (B) TYPE: amino acid
        (D) TOPOLOGY: linear (xi) SEQUENCE DESCRIPTION: SEQ ID NO:1:

Trp His Val Ala Arg
 1               5

(2) INFORMATION FOR SEQ ID NO:2:

(i) SEQUENCE CHARACTERISTICS:
        (A) LENGTH: 6
        (B) TYPE: amino acid
        (D) TOPOLOGY: linear (xi) SEQUENCE DESCRIPTION: SEQ ID NO:2:

Pro Leu Asp Val Tyr Lys
 1               5

(2) INFORMATION FOR SEQ ID NO:3:

(i) SEQUENCE CHARACTERISTICS:
        (A) LENGTH: 5
        (B) TYPE: amino acid
        (D) TOPOLOGY: linear (xi) SEQUENCE DESCRIPTION: SEQ ID NO:3:

Tyr Pro Ala Phe Lys
 1               5

(2) INFORMATION FOR SEQ ID NO:4:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:4:

Gln Ala Glu Val Ser
 1               5

(2) INFORMATION FOR SEQ ID NO:5:

(i) SEQUENCE CHARACTERISTICS:
        (A) LENGTH: 10
        (B) TYPE: amino acid
        (D) TOPOLOGY: linear (xi) SEQUENCE DESCRIPTION: SEQ ID NO:5:

Pro Glu Glu Val Thr Arg Pro Asn Tyr Leu
 1               5                   10

(2) INFORMATION FOR SEQ ID NO:6:

(i) SEQUENCE CHARACTERISTICS:
        (A) LENGTH: 9
        (B) TYPE: amino acid
        (D) TOPOLOGY: linear (xi) SEQUENCE DESCRIPTION: SEQ ID NO:6:

Tyr Asp Val Pro Trp Asn Glu Thr Ile
 1               5

(2) INFORMATION FOR SEQ ID NO:7:

(i) SEQUENCE CHARACTERISTICS:
        (A) LENGTH: 10
        (B) TYPE: amino acid
        (D) TOPOLOGY: linear (xi) SEQUENCE DESCRIPTION: SEQ ID NO:7:

Val Pro Pro Phe Glu Asn Ile Glu Leu Tyr
 1               5                   10

(2) INFORMATION FOR SEQ ID NO:8:

(i) SEQUENCE CHARACTERISTICS:
        (A) LENGTH: 11
        (B) TYPE: amino acid
        (D) TOPOLOGY: linear (xi) SEQUENCE DESCRIPTION: SEQ ID NO:8:

Gly Gly Gln Pro Leu Trp Ile Thr Ala Thr Lys
 1               5                   10

(2) INFORMATION FOR SEQ ID NO:9:

(i) SEQUENCE CHARACTERISTICS:
        (A) LENGTH: 16
        (B) TYPE: amino acid
        (D) TOPOLOGY: linear (xi) SEQUENCE DESCRIPTION: SEQ ID NO:9:

Val Asn Ser Met Gln Thr Val Phe Val Gly Tyr Gly
 1               5                   10

Pro Thr Phe Lys
         15

(2) INFORMATION FOR SEQ ID NO:10:

(i) SEQUENCE CHARACTERISTICS:
        (A) LENGTH: 12
        (B) TYPE: amino acid
        (D) TOPOLOGY: linear (xi) SEQUENCE DESCRIPTION: SEQ ID NO:10:

Asp Ile Glu His Leu Thr Ser Leu Asp Phe Phe Arg
 1               5                   10

(2) INFORMATION FOR SEQ ID NO:11:

(i) SEQUENCE CHARACTERISTICS:
        (A) LENGTH: 23
        (B) TYPE: amino acid
        (D) TOPOLOGY: linear (xi) SEQUENCE DESCRIPTION: SEQ ID NO:11:

Thr Glu Phe Leu Ser Asn Tyr Leu Thr Asn Val Asp
 1               5                   10

Asp Ile Thr Leu Val Pro Glu Thr Leu Gly Arg
         15                  20

(2) INFORMATION FOR SEQ ID NO:12:

(i) SEQUENCE CHARACTERISTICS:
    (A) LENGTH: 18
    (B) TYPE: nucleic acid
    (C) STRANDEDNESS: single
    (D) TOPOLOGY: linear (xi) SEQUENCE DESCRIPTION: SEQ ID NO:12:

GTTGGCAGCN ACRTGCCA                                             18

(2) INFORMATION FOR SEQ ID NO:13:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO:13:

TGGCAYGTNG CTGCCAAC                                             18

(2) INFORMATION FOR SEQ ID NO:14:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO:14:

CTTGAAGGCA GGGTA                                                15

(2) INFORMATION FOR SEQ ID NO:15:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO:15:

TAYCCTGCNT TYAAG                                                15

(2) INFORMATION FOR SEQ ID NO:16:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO:16:

GGTNACYTCY TCAGG                                                15

(2) INFORMATION FOR SEQ ID NO:17:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO:17:

CCTGARGARG TNACC                                                15

(2) INFORMATION FOR SEQ ID NO:18:

(i) SEQUENCE CHARACTERISTICS:
            (A) LENGTH: 21
            (B) TYPE: nucleic acid
            (C) STRANDEDNESS: single
            (D) TOPOLOGY: linear (xi) SEQUENCE DESCRIPTION: SEQ ID NO:18:

NGTNGCRTCR AATGGCACRT C                                                      21

(2) INFORMATION FOR SEQ ID NO:19:

(i) SEQUENCE CHARACTERISTICS:
            (A) LENGTH: 21
            (B) TYPE: nucleic acid
            (C) STRANDEDNESS: single
            (D) TOPOLOGY: linear (xi) SEQUENCE DESCRIPTION: SEQ ID NO:19:

GAYGTGCCAT TYGAYGCNAC N                                                      21

(2) INFORMATION FOR SEQ ID NO:20:

(i) SEQUENCE CHARACTERISTICS:
            (A) LENGTH: 21
            (B) TYPE: nucleic acid
            (C) STRANDEDNESS: single
            (D) TOPOLOGY: linear (xi) SEQUENCE DESCRIPTION: SEQ ID NO:20:

GTTDATRTTS TCRAATGGGG G                                                      21

(2) INFORMATION FOR SEQ ID NO:21:

(i) SEQUENCE CHARACTERISTICS:
            (A) LENGTH: 21
            (B) TYPE: nucleic acid
            (C) STRANDEDNESS: single
            (D) TOPOLOGY: linear (xi) SEQUENCE DESCRIPTION: SEQ ID NO:21:

CCCCCATTTG AGAACATCAA C                                                      21

(2) INFORMATION FOR SEQ ID NO:22:

(i) SEQUENCE CHARACTERISTICS:
            (A) LENGTH: 33
            (B) TYPE: nucleic acid
            (C) STRANDEDNESS: single
            (D) TOPOLOGY: linear (xi) SEQUENCE DESCRIPTION: SEQ ID NO:22:

CTTNGTNGCN GTDATCCANA RGGGYTGGCC GCC                                         33

(2) INFORMATION FOR SEQ ID NO:23:

(i) SEQUENCE CHARACTERISTICS:
            (A) LENGTH: 33
            (B) TYPE: nucleic acid
            (C) STRANDEDNESS: single
            (D) TOPOLOGY: linear (xi) SEQUENCE DESCRIPTION: SEQ ID NO:23:

GGCGGCCARC CCYTNTGGAT HACNGCNACN AAG                                         33

(2) INFORMATION FOR SEQ ID NO:24:

(i) SEQUENCE CHARACTERISTICS:

(A) LENGTH: 39
        (B) TYPE: nucleic acid
        (C) STRANDEDNESS: single
        (D) TOPOLOGY: linear (xi) SEQUENCE DESCRIPTION: SEQ ID NO:24:

CTTRAAGGTG GGGCCRTAGC CCACRAAGAC TGTYTGCAT                              39

(2) INFORMATION FOR SEQ ID NO:25:

(i) SEQUENCE CHARACTERISTICS:
        (A) LENGTH: 39
        (B) TYPE: nucleic acid
        (C) STRANDEDNESS: single
        (D) TOPOLOGY: linear (xi) SEQUENCE DESCRIPTION: SEQ ID NO:25:

ATGCARACAG TCTTYGTGGG CTAYGGCCCC ACCTTYAAR                              39

(2) INFORMATION FOR SEQ ID NO:26:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO:26:

Gln Tyr Leu His Gln Tyr Gly Ser Ser
 1               5

(2) INFORMATION FOR SEQ ID NO:27:

(i) SEQUENCE CHARACTERISTICS:
        (A) LENGTH: 5
        (B) TYPE: amino acid
        (C) STRANDEDNESS: single
        (D) TOPOLOGY: linear (xi) SEQUENCE DESCRIPTION: SEQ ID NO:27:

Val Leu Asn Tyr Phe
 1               5

(2) INFORMATION FOR SEQ ID NO:28:

(i) SEQUENCE CHARACTERISTICS:
        (A) LENGTH: 5
        (B) TYPE: amino acid
        (C) STRANDEDNESS: single
        (D) TOPOLOGY: linear (xi) SEQUENCE DESCRIPTION: SEQ ID NO:28:

Tyr Leu Asn Ala Thr
 1               5

(2) INFORMATION FOR SEQ ID NO:29:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO:29:

His Leu Leu Tyr Gly Arg Pro Ala Val Leu Tyr
 1               5                  10

```
(2) INFORMATION FOR SEQ ID NO:30:

(i) SEQUENCE CHARACTERISTICS:
        (A) LENGTH: 11
        (B) TYPE: amino acid
        (C) STRANDEDNESS: single
        (D) TOPOLOGY: linear (xi) SEQUENCE DESCRIPTION: SEQ ID NO:30:

Ser Tyr Pro Glu Ile Leu Thr Pro Ala Asp Asn
 1               5                  10

(2) INFORMATION FOR SEQ ID NO:31:

(i) SEQUENCE CHARACTERISTICS:
        (A) LENGTH: 14
        (B) TYPE: amino acid
        (C) STRANDEDNESS: single
        (D) TOPOLOGY: linear (xi) SEQUENCE DESCRIPTION: SEQ ID NO:31:

Xaa Tyr Gly Phe Leu Phe Pro Pro Tyr Leu Ser Ser
 1               5                  10
Ser Pro (2) INFORMATION FOR SEQ ID NO:32:

(i) SEQUENCE CHARACTERISTICS:
        (A) LENGTH: 13
        (B) TYPE: amino acid
        (C) STRANDEDNESS: single
        (D) TOPOLOGY: linear (xi) SEQUENCE DESCRIPTION: SEQ ID NO:32:

Thr Phe Pro Asn Leu Tyr Thr Phe Ala Thr Gly Leu
 1               5                  10
Tyr (2) INFORMATION FOR SEQ ID NO:33:

(i) SEQUENCE CHARACTERISTICS:
        (A) LENGTH: 22
        (B) TYPE: amino acid
        (C) STRANDEDNESS: single
        (D) TOPOLOGY: linear (xi) SEQUENCE DESCRIPTION: SEQ ID NO:33:

Val Asn Val Ile Ser Gly Pro Ile Asp Asp Tyr Asp
 1               5                  10
Tyr Asp Gly Leu His Asp Thr Glu Asp Lys
            15                  20

(2) INFORMATION FOR SEQ ID NO:34:

(i) SEQUENCE CHARACTERISTICS:
        (A) LENGTH:  829
        (B) TYPE:  amino acid
        (C) STRANDEDNESS:  single
        (D) TOPOLOGY:  Unknown (ii) MOLECULE TYPE:  protein (iii) HYPOTHETICAL: No (vi) ORIGINAL SOURCE:
        (A) ORGANISM: Human
        (B) STRAIN:
        (C) INDIVIDUAL ISOLATE:
```

(D) DEVELOPMENTAL STAGE:
(E) HAPLOTYPE:
(F) TISSUE TYPE:
(G) CELL TYPE: Melanoma
(H) CELL LINE: A2058
(I) ORGANELLE:

(ix) FEATURE:
(A) NAME/KEY:
(B) LOCATION:
(C) IDENTIFICATION METHOD:
(D) OTHER INFORMATION: Putative protein sequence of A2058 Autotaxin (xi) SEQUENCE DESCRIPTION: SEQ ID NO:34:

```
Cys His Asp Phe Asp Glu Leu Cys Leu Lys Thr Ala
 1               5                  10

Arg Gly Trp Glu Cys Thr Lys Asp Arg Cys Gly Glu
            15                  20

Val Arg Asn Glu Glu Asn Ala Cys His Cys Ser Glu
 25              30                  35

Asp Cys Leu Ala Arg Gly Asp Cys Cys Thr Asn Tyr
            40                  45

Gln Val Val Cys Lys Gly Glu Ser His Trp Val Asp
 50              55                          60

Asp Asp Cys Glu Glu Ile Lys Ala Ala Glu Cys Pro
            65                  70

Ala Gly Phe Val Arg Pro Pro Leu Ile Ile Phe Ser
        75                  80

Val Asp Gly Phe Arg Ala Ser Tyr Met Lys Lys Gly
 85              90                  95

Ser Lys Val Met Pro Asn Ile Glu Lys Leu Arg Ser
            100                 105

Cys Gly Thr His Ser Pro Tyr Met Arg Pro Val Tyr
        110                 115                 120

Pro Thr Lys Thr Phe Pro Asn Leu Tyr Thr Leu Ala
            125                 130

Thr Gly Leu Tyr Pro Glu Ser His Gly Ile Val Gly
        135                 140

Asn Ser Met Tyr Asp Pro Val Phe Asp Ala Thr Phe
 145             150                 155

His Leu Arg Gly Arg Glu Lys Phe Asn His Arg Trp
            160                 165

Trp Gly Gly Gln Pro Leu Trp Ile Thr Ala Thr Lys
        170                 175                 180

Gln Gly Val Lys Ala Gly Thr Phe Phe Trp Ser Val
            185                 190

Val Ile Pro His Glu Arg Arg Ile Leu Thr Ile Leu
        195                 200

Arg Trp Leu Thr Leu Pro Asp His Glu Arg Pro Ser
 205                 210                 215

Val Tyr Ala Phe Tyr Ser Glu Gln Pro Asp Phe Ser
            220                 225

Gly His Lys Tyr Gly Pro Phe Gly Pro Glu Glu Ser
        230                 235                 240

Ser Tyr Gly Ser Pro Phe Thr Pro Ala Lys Arg Pro
            245                 250
```

```
Lys Arg Lys Val Ala Pro Lys Arg Arg Gln Glu Arg
            255                 260
Pro Val Ala Pro Pro Lys Lys Arg Arg Arg Lys Ile
265                 270                 275
His Arg Met Asp His Tyr Ala Ala Glu Thr Arg Gln
                280                 285
Asp Lys Met Thr Asn Pro Leu Arg Glu Ile Asp Lys
        290                 295                 300
Ile Val Gly Gln Leu Met Asp Gly Leu Lys Gln Leu
                    305                 310
Lys Leu Arg Arg Cys Val Asn Val Ile Phe Val Gly
            315                 320
Asp His Gly Met Glu Asp Val Thr Cys Asp Arg Thr
325                 330                 335
Glu Phe Leu Ser Asn Tyr Leu Thr Asn Val Asp Asp
                340                 345
Ile Thr Leu Val Pro Gly Thr Leu Gly Arg Ile Arg
        350                 355                 360
Ser Lys Phe Ser Asn Asn Ala Lys Tyr Asp Pro Lys
                    365                 370
Ala Ile Ile Ala Asn Leu Thr Cys Lys Lys Pro Asp
            375                 380
Gln His Phe Lys Pro Tyr Leu Lys Gln His Leu Pro
385                 390                 395
Lys Arg Leu His Tyr Ala Asn Asn Arg Arg Ile Glu
                400                 405
Asp Ile His Leu Leu Val Glu Arg Arg Trp His Val
        410                 415                 420
Ala Arg Lys Pro Leu Asp Val Tyr Lys Lys Pro Ser
                    425                 430
Gly Lys Cys Phe Phe Gln Gly Asp His Gly Phe Asp
            435                 440
Asn Lys Val Asn Ser Met Gln Thr Val Phe Val Gly
445                 450                 455
Tyr Gly Pro Thr Phe Lys Tyr Lys Thr Lys Val Pro
                460                 465
Pro Phe Glu Asn Ile Glu Leu Tyr Asn Val Met Cys
        470                 475                 480
Asp Leu Leu Gly Leu Lys Pro Ala Pro Asn Asn Gly
                    485                 490
Thr His Gly Ser Leu Asn His Leu Leu Arg Thr Asn
            495                 500
Thr Phe Arg Pro Thr Met Pro Glu Glu Val Thr Arg
505                 510                 515
Pro Asn Tyr Pro Gly Ile Met Tyr Leu Gln Ser Asp
                520                 525
Asp Asp Leu Gly Cys Thr Cys Asp Asp Lys Val Glu
        530                 535                 540
Pro Lys Asn Lys Leu Asp Glu Leu Asn Lys Arg Leu
                    545                 550
His Thr Lys Gly Ser Thr Glu Glu Arg His Leu Leu
            555                 560
Tyr Gly Arg Pro Ala Val Leu Tyr Arg Thr Arg Tyr
```

```
565                     570                     575
Asp Ile Leu Tyr His Thr Asp Phe Glu Ser Gly Tyr
                580                 585
Ser Glu Ile Phe Leu Met Leu Leu Trp Thr Ser Tyr
    590                 595                 600
Thr Val Ser Lys Gln Ala Glu Val Ser Ser Val Pro
                605                 610
Asp His Leu Thr Ser Cys Val Arg Pro Asp Val Arg
                615                 620
Val Ser Pro Ser Phe Ser Gln Asn Cys Leu Ala Tyr
625                 630                 635
Lys Asn Asp Lys Gln Met Ser Tyr Gly Phe Leu Phe
                640                 645
Pro Pro Tyr Leu Ser Ser Ser Pro Glu Ala Lys Tyr
    650                 655                 660
Asp Ala Phe Leu Val Thr Asn Met Val Pro Met Tyr
                665                 670
Pro Ala Phe Lys Arg Val Trp Asn Tyr Phe Gln Arg
                675                 680
Val Leu Val Lys Lys Tyr Ala Ser Glu Arg Asn Gly
685                 690                 695
Val Asn Val Ile Ser Gly Pro Ile Phe Asp Tyr Asp
                700                 705
Tyr Asp Gly Leu His Asp Thr Glu Asp Lys Ile Lys
    710                 715                 720
Gln Tyr Val Glu Gly Ser Ser Ile Pro Val Pro Thr
                725                 730
His Tyr Tyr Ser Ile Ile Thr Ser Cys Leu Asp Phe
    735                 740
Thr Gln Pro Ala Asp Lys Cys Asp Gly Pro Leu Ser
745                 750                 755
Val Ser Ser Phe Ile Leu Pro His Arg Pro Asp Asn
                760                 765
Glu Glu Ser Cys Asn Ser Ser Glu Asp Glu Ser Lys
    770                 775                 780
Trp Val Glu Glu Leu Met Lys Met His Thr Ala Arg
                785                 790
Val Arg Asp Ile Glu His Leu Thr Ser Leu Asp Phe
    795                 800
Phe Arg Lys Thr Ser Arg Ser Tyr Pro Glu Ile Leu
805                 810                 815
Thr Leu Lys Thr Tyr Leu His Thr Tyr Glu Ser Glu
                820                 825
Ile (2) INFORMATION FOR SEQ ID NO:35:

(i) SEQUENCE CHARACTERISTICS:
        (A) LENGTH: 2946
        (B) TYPE: nucleic acid
        (C) STRANDEDNESS: double
        (D) TOPOLOGY: Unknown (ii) MOLECULE TYPE: cDNA (iii) HYPOTHETICAL: No
```

(vi) ORIGINAL SOURCE:
              (A) ORGANISM: Human
              (B) STRAIN:
              (C) INDIVIDUAL ISOLATE:
              (D) DEVELOPMENTAL STAGE:
              (E) HAPLOTYPE:
              (F) TISSUE TYPE:
              (G) CELL TYPE: Melanoma
              (H) CELL LINE: A2058
              (I) ORGANELLE:

(ix) FEATURE:
              (A) NAME/KEY:
              (B) LOCATION:
              (C) IDENTIFICATION METHOD:
              (D) OTHER INFORMATION: Partial DNA Sequence
                  of A2058 Autotaxin (xi) SEQUENCE DESCRIPTION: SEQ ID NO:35:

```
GCTGCCATGA CTTTGATGAG CTGTGTTTGA AGACAGCCCG                40

TGGCTGGGAG TGTACTAAGG ACAGATGTGG AGAAGTCAGA                80

AATGAAGAAA ATGCCTGTCA CTGCTCAGAG GACTGCTTGG              120

CCAGGGGAGA CTGCTGTACC AATTACCAAG TGGTTTGCAA              160

AGGAGAGTCG CATTGGGTTG ATGATGACTG TGAGGAAATA              200

AAGGCCGCAG AATGCCCTGC AGGGTTTGTT CGCCCTCCAT              240

TAATCATCTT CTCCGTGGAT GGCTTCCGTG CATCATACAT              280

GAAGAAAGGC AGCAAAGTCA TGCCTAATAT TGAAAAACTA              320

AGGTCTTGTG GCACACACTC TCCCTACATG AGGCCGGTGT              360

ACCCAACTAA AACCTTTCCT AACTTATACA CTTTGGCCAC              400

TGGGCTATAT CCAGAATCAC ATGGAATTGT TGGCAATTCA              440

ATGTATGATC CTGTATTTGA TGCCACTTTT CATCTGCGAG              480

GGCGAGAGAA ATTTAATCAT AGATGGTGGG GAGGTCAACC              520

GCTATGGATT ACAGCCACCA AGCAAGGGGT GAAAGCTGGA              560

ACATTCTTTT GGTCTGTTGT CATCCCTCAC GAGCGGAGAA              600

TATTAACCAT ATTGCGGTGG CTCACCCTGC CAGATCATGA              640

GAGGCCTTCG GTCTATGCCT TCTATTCTGA GCAACCTGAT              680

TTCTCTGGAC ACAAATATGG CCCTTTCGGC CCTGAGGAGA              720

GTAGTTATGG CTCACCTTTT ACTCCGGCTA AGAGACCTAA              760

GAGGAAAGTT GCCCCTAAGA GGAGACAGGA AAGACCAGTT              800

GCTCCTCCAA AGAAAAGAAG AAGAAAAATA CATAGGATGG              840

ATCATTATGC TGCGGAAACT CGTCAGGACA AAATGACAAA              880

TCCTCTGAGG GAAATCGACA AAATTGTGGG GCAATTAATG              920

GATGGACTGA ACAACTAAA ACTGCGTCGG TGTGTCAACG              960

TCATCTTTGT CGGAGACCAT GGAATGGAAG ATGTCACATG              1000

TGATAGAACT GAGTTCTTGA GTAATTACCT AACTAATGTG              1040

GATGATATTA CTTTAGTGCC TGGAACTCTA GGAAGAATTC              1080

GATCCAAATT TAGCAACAAT GCTAAATATG ACCCCAAAGC              1120

CATTATTGCC AATCTCACGT GTAAAAAACC AGATCAGCAC              1160
```

```
TTTAAGCCTT ACTTGAAACA GCACCTTCCC AAACGTTTGC                    1200

ACTATGCCAA CAACAGAAGA ATTGAGGATA TCCATTTATT                    1240

GGTGGAACGC AGATGGCATG TTGCAAGGAA ACCTTTGGAT                    1280

GTTTATAAGA AACCATCAGG AAAATGCTTT TTCCAGGGAG                    1320

ACCACGGATT TGATAACAAG GTCAACAGCA TGCAGACTGT                    1360

TTTTGTAGGT TATGGCCCAA CATTTAAGTA CAAGACTAAA                    1400

GTGCCTCCAT TTGAAAACAT TGAACTTTAC AATGTTATGT                    1440

GTGATCTCCT GGGATTGAAG CCAGCTCCTA ATAATGGGAC                    1480

CCATGGAAGT TTGAATCATC TCCTGCGCAC TAATACCTTC                    1520

AGGCCAACCA TGCCAGAGGA AGTTACCAGA CCCAATTATC                    1560

CAGGGATTAT GTACCTTCAG TCTGATTTTG ACCTGGGCTG                    1600

CACTTGTGAT GATAAGGTAG AGCCAAAGAA CAAGTTGGAT                    1640

GAACTCAACA AACGGCTTCA TACAAAAGGG TCTACAGAAG                    1680

AGAGACACCT CCTCTATGGG CGACCTGCAG TGCTTTATCG                    1720

GACTAGATAT GATATCTTAT ATCACACTGA CTTTGAAAGT                    1760

GGTTATAGTG AAATATTCCT AATGCTACTC TGGACATCAT                    1800

ATACTGTTTC CAAACAGGCT GAGGTTTCCA GCGTTCCTGA                    1840

CCATCTGACC AGTTGCGTCC GGCCTGATGT CCGTGTTTCT                    1880

CCGAGTTTCA GTCAGAACTG TTTGGCCTAC AAAAATGATA                    1920

AGCAGATGTC CTACGGATTC CTCTTTCCTC CTTATCTGAG                    1960

CTCTTCACCA GAGGCTAAAT ATGATGCATT CCTTGTAACC                    2000

AATATGGTTC CAATGTATCC TGCTTTCAAA CGGGTCTGGA                    2040

ATTATTTCCA AAGGGTATTG GTGAAGAAAT ATGCTTCGGA                    2080

AAGAAATGGA GTTAACGTGA TAAGTGGACC AATCTTCGAC                    2120

TATGACTATG ATGGCTTACA TGACACAGAA GACAAAATAA                    2160

AACAGTACGT GGAAGGCAGT TCCATTCCTG TTCCAACTCA                    2200

CTACTACAGC ATCATCACCA GCTGTCTGGA TTTCACTCAG                    2240

CCTGCCGACA AGTGTGACGG CCCTCTCTCT GTGTCCTCCT                    2280

TCATCCTGCC TCACCGGCCT GACAAAGAGG AGAGCTGCAA                    2320

TAGCTCAGAG GACGAATCAA AATGGGTAGA AGAACTCATG                    2360

AAGATGCACA CAGCTAGGGT GCGTGACATT GAACATCTCA                    2400

CCAGCCTGGA CTTCTTCCGA AAGACCAGCC GCAGCTACCC                    2440

AGAAATCCTG ACACTCAAGA CATACCTGCA TACATATGAG                    2480

AGCGAGATTT AACTTTCTGA GCATCTGCAG TACAGTCTTA                    2520

TCAACTGGTT GTATATTTTT ATATTGTTTT TGTATTTATT                    2560

AATTTGAAAC CAGGACATTA AAAATGTTAG TATTTTAATC                    2600

CTGTACCAAA TCTGACATAT TATGCCTGAA TGACTCCACT                    2640

GTTTTTCTCT AATGCTTGAT TTAGGTAGCC TTGTGTTCTG                    2680

AGTAGAGCTT GTAATAAATA CTGCAGCTTG AGAAAAAGTG                    2720

GAAGCTTCTA AATGGTGCTG CAGATTTGAT ATTTGCATTG                    2760
```

```
AGGAAATATT AATTTTCCAA TGCACAGTTG CCACATTTAG                2800

TCCTGTACTG TATGGAAACA CTGATTTTGT AAAGTTGCCT                2840

TTATTTGCTG TTAACTGTTA ACTATGACAG ATATATTTAA                2880

GCCTTATAAA CCAATCTTAA ACATAATAAA TCACACATTC                2920

AGTTTTAAAA AAAAAAAAA AAAAA                                 2946
```

(2) INFORMATION FOR SEQ ID NO:36:

(i) SEQUENCE CHARACTERISTICS:
        (A) LENGTH: 788
        (B) TYPE: amino acid
        (C) STRANDEDNESS: single
        (D) TOPOLOGY: Unknown (ii) MOLECULE TYPE: protein (iii) HYPOTHETICAL: No (vi) ORIGINAL SOURCE:
        (A) ORGANISM: Human
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE: teratocarcinoma
        (H) CELL LINE: N-tera 2D1
        (I) ORGANELLE:

(ix) FEATURE:
        (A) NAME/KEY:
        (B) LOCATION:
        (C) IDENTIFICATION METHOD:
        (D) OTHER INFORMATION: N-tera 2D1 putative
            ATX protein sequence (xi) SEQUENCE DESCRIPTION: SEQ ID NO:36:

```
Cys Asp Asn Leu Cys Lys Ser Tyr Thr Ser Cys Cys
  1               5                  10

His Asp Phe Asp Glu Leu Cys Leu Lys Thr Ala Arg
         15                  20

Ala Trp Glu Cys Thr Lys Asp Arg Cys Gly Glu Val
 25                  30                  35

Arg Asn Glu Glu Asn Ala Cys His Cys Ser Glu Asp
              40                  45

Cys Leu Ala Arg Gly Asp Cys Cys Thr Asn Tyr Gln
     50                  55                  60

Val Val Cys Lys Gly Glu Ser His Trp Val Asp Asp
                  65                  70

Asp Cys Glu Glu Ile Lys Ala Ala Glu Cys Leu Gln
         75                  80

Val Asp Ser Pro Ser Ile Asn His Leu Leu Arg Gly
 85                  90                  95

Trp Leu Pro Met Thr Ser Tyr Met Lys Lys Gly Ser
             100                 105

Lys Val Met Pro Asn Ile Glu Lys Leu Arg Ser Cys
    110                 115                 120

Gly Thr His Ser Pro Tyr Met Arg Pro Val Tyr Pro
                125                 130

Thr Lys Thr Phe Pro Asn Leu Tyr Thr Leu Ala Thr
        135                 140
```

```
Gly Leu Tyr Pro Glu Ser His Gly Ile Val Gly Asn
145                 150                 155

Ser Met Tyr Asp Pro Val Phe Asp Ala Thr Phe His
            160                 165

Leu Arg Gly Arg Glu Lys Phe Asn His Arg Trp Trp
        170                 175                 180

Ala Gly Gln Pro Leu Trp Ile Thr Ala Thr Lys Gln
                185                 190

Arg Gly Glu Ser Trp Asn Ile Leu Leu Val Cys Cys
            195                 200

His Pro Ser Arg Ala Glu Ile Leu Thr Ile Leu Gln
205                 210                 215

Trp Leu Thr Leu Pro Asp His Glu Arg Pro Ser Val
            220                 225

Tyr Ala Phe Tyr Ser Glu Gln Pro Asp Phe Ser Gly
        230                 235                 240

His Lys His Met Pro Phe Gly Pro Glu Met Pro Asn
                245                 250

Pro Leu Arg Glu Met His Lys Ile Val Gly Gln Leu
            255                 260

Met Asp Gly Leu Lys Gln Leu Lys Leu His Arg Cys
265                 270                 275

Val Asn Val Ile Phe Val Glu Thr Met Asp Gly Arg
                280                 285

Cys His Met Tyr Arg Thr Glu Phe Leu Ser Asn Tyr
        290                 295                 300

Leu Thr Asn Val Asp Asp Ile Thr Leu Val Pro Gly
                305                 310

Thr Leu Gly Arg Ile Arg Ser Lys Phe Ser Asn Asn
            315                 320

Ala Lys Tyr Asp Pro Lys Ala Ile Ile Ala Asn Leu
325                 330                 335

Thr Cys Lys Lys Pro Asp Gln His Phe Lys Pro Tyr
            340                 345

Leu Lys Gln His Leu Pro Lys Arg Leu His Tyr Ala
        350                 355                 360

Asn Asn Arg Arg Ile Glu Asp Ile His Leu Leu Val
                365                 370

Glu Arg Arg Trp His Val Ala Arg Lys Pro Leu Asp
            375                 380

Val Tyr Lys Lys Pro Ser Gly Asn Ala Phe Ser Arg
385                 390                 395

Glu Thr Thr Ala Phe Asp Asn Lys Val Asn Ser Met
            400                 405

Gln Thr Val Phe Val Gly Tyr Gly Pro Thr Phe Lys
        410                 415                 420

Tyr Lys Thr Lys Val Pro Pro Phe Glu Asn Ile Glu
                425                 430

Leu Tyr Asn Val Met Cys Asp Leu Leu Gly Leu Lys
            435                 440

Pro Ala Pro Asn Asn Gly Thr His Phe Ser Leu Asn
445                 450                 455
```

-continued

```
His Leu Leu Arg Thr Asn Thr Phe Arg Pro Thr Met
            460                 465

Pro Glu Glu Val Thr Arg Pro Asn Tyr Pro Gly Ile
    470                 475                 480

Met Tyr Leu Gln Ser Asp Phe Asp Leu Gly Cys Thr
                485                 490

Cys Asp Asp Lys Val Glu Pro Lys Asn Lys Leu Asp
            495                 500

Glu Leu Asn Lys Arg Leu His Thr Lys Gly Ser Thr
505                 510                 515

Glu Glu Arg His Leu Leu Tyr Gly Asp Arg Pro Ala
            520                 525

Val Leu Tyr Arg Thr Arg Tyr Asp Ile Leu Tyr His
        530                 535                 540

Thr Asp Phe Glu Ser Gly Tyr Ser Glu Ile Phe Leu
                545                 550

Met Pro Leu Trp Thr Ser Tyr Thr Val Ser Lys Gln
            555                 560

Ala Glu Val Ser Ser Val Pro Asp His Leu Thr Ser
565                 570                 575

Cys Val Arg Pro Asp Val Arg Val Ser Pro Ser Phe
            580                 585

Ser Gln Asn Cys Leu Ala Tyr Lys Asn Asp Lys Gln
    590                 595                 600

Met Ser Tyr Gly Gly Leu Gly Pro Pro Tyr Leu Ser
                605                 610

Ser Ser Pro Glu Ala Lys Tyr Asp Ala Phe Leu Val
        615                 620

Thr Asn Met Val Pro Met Tyr Pro Ala Phe Lys Arg
625                 630                 635

Val Trp Asn Tyr Phe Gln Arg Val Leu Val Lys Lys
            640                 645

Tyr Ala Ser Glu Arg Asn Gly Val Asn Val Ile Ser
    650                 655                 660

Gly Pro Ile Phe Asp Tyr Asp Tyr Asp Gly Leu His
                665                 670

Asp Thr Glu Asp Lys Ile Lys Gln Tyr Val Glu Gly
        675                 680

Ser Ser Ile Pro Val Pro Thr His Tyr Ser Tyr Ile
685                 690                 695

Ile Thr Ser Cys Leu Asp Phe Thr Gln Pro Ala Asp
            700                 705

Lys Cys Asp Gly Pro Leu Ser Val Ser Ser Phe Ile
    710                 715                 720

Leu Pro His Arg Pro Asp Asn Glu Glu Ser Cys Asn
                725                 730

Ser Ser Glu Asp Glu Ser Lys Trp Val Glu Glu Leu
        735                 740

Met Lys Met His Thr Ala Arg Val Arg Asp Ile Glu
745                 750                 755

His Leu Thr Ser Leu Asp Phe Phe Arg Lys Thr Ser
            760                 765

Arg Ser Tyr Pro Glu Ile Leu Thr Leu Lys Thr Tyr
```

```
                            770                 775                 780

Leu His Thr Tyr Glu Ser Glu Ile
                    785

(2) INFORMATION FOR SEQ ID NO:37:

(i) SEQUENCE CHARACTERISTICS:
        (A) LENGTH: 2712
        (B) TYPE: nucleic acid
        (C) STRANDEDNESS: double
        (D) TOPOLOGY: Unknown (ii) MOLECULE TYPE: cDNA (iii) HYPOTHETICAL: No (vi) ORIGINAL SOURCE:
        (A) ORGANISM: Human
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE: teratocarcinoma
        (H) CELL LINE: N-tera 2D1
        (I) ORGANELLE:

(ix) FEATURE:
        (A) NAME/KEY:
        (B) LOCATION:
        (C) IDENTIFICATION METHOD:
        (D) OTHER INFORMATION: N-tera 2D1 ATX DNA
            sequence (xi) SEQUENCE DESCRIPTION: SEQ ID NO:37:

TGTGACAACT TGTGTAAGAG CTATACCAGT TGCTGCCATG                              40

ACTTTGATGA GCTGTGTTTG AAGACAGCCC GTGCGTGGGA                              80

GTGTACTAAG GACAGATGTG GGGAAGTCAG AAATGAAGAA                             120

AATGCCTGTC ACTGCTCAGA GGACTGCTTG GCCAGGGGAG                             160

ACTGCTGTAA CAATTACCAA GTGGTTTGCA AAGGAGAGTC                             200

GCATTGGGTT GATGATGACT GTGAGGAAAT AAAGGCCGCA                             240

GAATGCCTGC AGGTTTGTTC GCCCTCCATT AATCATCTTC                             280

TCCGTGGATG GCTTCCGATG ACATCATACA TGAAGAAAGG                             320

CAGCAAAGTC ATGCCTAATA TTGAAAAACT AAGGTCTTGT                             360

GGCACACACT CTCCCTACAT GAGGCCGGTG TACCCAACTA                             400

AAACCTTTCC TAACTTATAC ACTTTGGCCA CTGGGCTATA                             440

TCCAGAATCA CATGGAATTG TTGGCAATTC AATGTATGAT                             480

CCTGTATTTG ATGCCACTTT TCATCTGCGA GGGCGAGAGA                             520

AATTTAATCA TAGATGGTGG GGAGGTCAAC CGCTATGGAT                             560

TACAGCCACC AAGCAAAGGG GTGAAAGCTG GAACATTCTT                             600

TTGGTCTGTT GTCATCCCTC ACGAGCGGAG ATATTAACCA                             640

TATTGCAGTG GCTCACCCTG CCAGATCATG AGAGGCCTTC                             680

GGTCTATGCC TTCTATTCTG AGCAACCTGA TTTCTCTGGA                             720

CACAAACATA TGCCTTTCGG CCCTGAGATG ACAAATCCTC                             760

TGAGGGAAAT GCACAAAATT GTGGGGCAAT TAATGGATGG                             800

ACTGAAACAA CTAAAACTGC ATCGGTGTGT CAACGTCATC                             840
```

| | |
|---|---|
| TTTGTCGAGA CCATGGATGG AAGATGTCAC ATGTATAGAA | 880 |
| CTGAGTTCTT GAGTAATTAC CTAACTAATG TGGATGATAT | 920 |
| TACTTTAGTG CCTGGAACTC TAGGAAGAAT TCGATCCAAA | 960 |
| TTTAGCAACA ATGCTAAATA TCACCCCAAA GCCATTATTG | 1000 |
| CCAATCTCAC GTGTAAAAAA CCAGATCAGC ACTTTAAGCC | 1040 |
| TTACTTGAAA CAGCACCTTC CCAAACGTTT GCACTATGCC | 1080 |
| AACAACAGAA GAATTGAGGA TATCCATTTA TTGGTGGAAC | 1120 |
| GCAGATGGCA TGTTGCAAGG AAACCTTTGG ATGTTTATAA | 1160 |
| GAAACCATCA GGAAATGCTT TTTCCAGGGA GACCACGGCA | 1200 |
| TTTGATAACA AGGTCAACAG CATGCAGACT GTTTTTGTAG | 1240 |
| GTTATGGCCC AACATTTAAG TACAAGACTA AAGTDCCTCC | 1280 |
| ATTTGAAAAC ATTGAACTTT AAAATGTTAT GTGTGATCTC | 1320 |
| CTGGGATTGA AGCCAGCTCC TAATAATGGG ACCCATGGAA | 1360 |
| GTTTGAATCA TCTCCTGCGC ACTAATACCT TCAGGCCAAC | 1400 |
| CATGCCAGAG GAAGTTACCA GACCCTATTA TCCAGGGATT | 1440 |
| ATGTACCTTC AGTCTGATTT TGACCTGGGC TGCACTTGTG | 1480 |
| ATGATAAGGT AGAGCCAAAG AACAAGTTGG ATGAACTCAA | 1520 |
| CAAACGGCTT CATACAAAAG GGTCTACAGA AGAGAGACAC | 1560 |
| CTCCTCTATG GGGATCGACC TGCAGTGCTT TATCGGACTA | 1600 |
| GATATGATAT CTTATATCAC ACTGACTTTG AAAGTGGTTA | 1640 |
| TAGTGAAATA TTCCTAATGC CACTCTGGAC ATCATATACT | 1680 |
| GTTTCCAAAC AGGCTGAGGT TTCCAGCGTT CCTGACCATC | 1720 |
| TGACCAGTTG CGTCCGGCCT GATGTCCGTG TTTCTCCGAG | 1760 |
| TTTCAGTCAG AACTGTTTGG CCTACAAAAA TGATAAGCAG | 1800 |
| ATGTCCTACG GATTCCTCTT TCCTCCTTAT CTGAGCTCTT | 1840 |
| CACCAGAGGC TAAATATGAT GCATTCCTTG TAACCAATAT | 1880 |
| GGTTCCAATG TATCCTGCTT TCAAACGGGT CTGGAATTAT | 1920 |
| TTCCAAAGGG TATTGGTGAA GAAATATGCT TCGGAAAGAA | 1960 |
| ATGGAGTTAA CGTGATAAGT GGACCAATCT TCGACTATGA | 2000 |
| CTATGATGGC TTACATGACA CAGAAGACAA AATAAAACAG | 2040 |
| TACGTGGAAG GCAGTTCCAT TCCTGTTCCA ACTCACTACT | 2080 |
| ACAGCATCAT CACCAGCTGT CTGGATTTCA CTCAGCCTGC | 2120 |
| CGACAAGTGT GACGGCCCTC TCTCTGTGTC CTCCTTCATC | 2160 |
| CTGCCTCACC GGCCTGACAA CGAGGAGAGC TGCAATAGCT | 2200 |
| CAGAGGACGA ATCAAAATGG GTAGAAGAAC TCATGAAGAT | 2240 |
| GCACACAGCT AGGGTGCGTG ACATTGAACA TCTCACCAGC | 2280 |
| CTGGACTTCT TCCGAAAGAC CAGCCGCAGC TACCCAGAAA | 2320 |
| TCCTGACACT CAAGACATAC CTGCATACAT ATGAGAGCGA | 2360 |
| GATTTAACTT TCTGAGCATC TGCAGTACAG TCTTATCAAC | 2400 |

```
TGGTTGTATA TTTTTATATT GTTTTTGTAT TTATTAATTT                    2440

GAAACCAGGA CATTAAAAAT GTTAGTATTT TAATCCTGTA                    2480

CCAAATCTGA CATATTATGC CTGAATGACT CCACTGTTTT                    2520

TCTCTAATGC TTGATTTAGG TAGCCTTGTG TTCTGAGTAG                    2560

AGCTTGTAAT AAATACTGCA GCTTGAGTTT TTAGTGGAAG                    2600

CTTCTAAATG GTGCTGCAGA TTTGATATTT GCATTGAGGA                    2640

AATATTAATT TTCCAATGCA CAGTTGCCAC ATTTAGTCCT                    2680

GTACTGTATG GAAACACTGA TTTTGTAAAG TT                            2712

(2) INFORMATION FOR SEQ ID NO:38:

(i) SEQUENCE CHARACTERISTICS:
        (A) LENGTH: 979
        (B) TYPE: amino acid
        (C) STRANDEDNESS: single
        (D) TOPOLOGY: Unknown (ii) MOLECULE TYPE: protein (iii) HYPOTHETICAL: No (vi) ORIGINAL SOURCE:
        (A) ORGANISM: Human
        (B) STRAIN:
        (C) INDIVIDUAL ISOLATE:
        (D) DEVELOPMENTAL STAGE:
        (E) HAPLOTYPE:
        (F) TISSUE TYPE: Liver
        (G) CELL TYPE:
        (H) CELL LINE:
        (I) ORGANELLE:

(ix) FEATURE:
        (A) NAME/KEY:
        (B) LOCATION:
        (C) IDENTIFICATION METHOD:
        (D) OTHER INFORMATION: putative autotaxin
            protein sequence from human liver (xi) SEQUENCE DESCRIPTION: SEQ ID NO:38:

Met Ala Arg Arg Ser Ser Phe Gln Ser Cys Gln Asp
 1               5                  10

Ile Ser Leu Phe Thr Phe Ala Val Gly Val Asn Ile
            15                  20

Cys Leu Gly Phe Thr Ala His Arg Ile Lys Arg Ala
    25                  30                  35

Glu Gly Trp Glu Glu Gly Pro Pro Thr Val Leu Ser
                40                  45

Asp Ser Pro Trp Thr Asn Ile Ser Gly Ser Cys Lys
    50                  55                  60

Gly Arg Cys Phe Glu Leu Gln Glu Ala Gly Pro Pro
                65                  70

Asp Cys Arg Cys Asp Asn Leu Cys Lys Ser Tyr Thr
        75                  80

Ser Cys Cys His Asp Phe Asp Glu Leu Cys Leu Lys
    85                  90                  95

Thr Ala Arg Ala Trp Glu Cys Thr Lys Asp Arg Cys
                100                 105

Gly Glu Val Arg Asn Glu Glu Asn Ala Cys His Cys
        110                 115                 120
```

```
Ser Glu Asp Cys Leu Ala Arg Gly Asp Cys Cys Thr
            125                 130

Asn Tyr Gln Val Val Cys Lys Gly Glu Ser His Trp
            135                 140

Val Asp Asp Asp Cys Glu Glu Ile Lys Ala Ala Glu
145                 150                 155

Cys Leu Gln Val Cys Ser Pro Ser Ile Asn His Leu
            160                 165

Leu Arg Gly Trp Leu Pro Met Thr Ser Tyr Met Lys
            170                 175                 180

Lys Gly Ser Lys Val Met Pro Asn Ile Glu Lys Leu
                185                 190

Arg Ser Cys Gly Thr His Ser Pro Tyr Met Arg Pro
            195                 200

Val Tyr Pro Thr Lys Thr Phe Pro Asn Leu Tyr Thr
205                 210                 215

Leu Ala Thr Gly Leu Tyr Pro Glu Ser His Gly Ile
            220                 225

Val Gly Asn Ser Met Tyr Asp Pro Val Phe Asp Ala
230                 235                 240

Thr Phe His Leu Arg Gly Arg Glu Lys Phe Asn His
            245                 250

Arg Trp Trp Gly Gly Gln Pro Leu Trp Ile Thr Ala
            255                 260

Thr Lys Gln Arg Gly Glu Ser Trp Asn Ile Leu Leu
265                 270                 275

Val Cys Cys His Pro Ser Arg Ala Glu Ile Leu Thr
            280                 285

Ile Leu Gln Trp Leu Thr Leu Pro Asp His Glu Arg
            290                 295                 300

Pro Ser Val Tyr Ala Phe Tyr Ser Glu Gln Pro Asp
            305                 310

Phe Ser Gly His Lys His Met Pro Phe Gly Pro Glu
            315                 320

Met Thr Asn Pro Leu Arg Glu Met His Lys Ile Val
325                 330                 335

Gly Gln Leu Met Asp Gly Leu Lys Gln Leu Lys Leu
            340                 345

His Arg Cys Val Asn Val Ile Phe Val Glu Thr Met
            350                 355                 360

Asp Gly Arg Cys His Met Tyr Arg Thr Glu Phe Leu
            365                 370

Ser Asn Tyr Leu Thr Asn Val Asp Asp Ile Thr Leu
            375                 380

Val Pro Gly Thr Leu Gly Arg Ile Arg Ser Lys Phe
385                 390                 395

Ser Asn Asn Ala Lys Tyr Asp Pro Lys Ala Ile Ile
            400                 405

Ala Asn Leu Thr Cys Lys Lys Pro Asp Gln His Phe
            410                 415                 420

Lys Pro Tyr Leu Lys Gln His Leu Pro Lys Arg Leu
            425                 430

His Tyr Ala Asn Asn Arg Arg Ile Glu Asp Ile His
```

```
                    435                 440
Leu Leu Val Glu Arg Arg Trp His Val Ala Arg Lys
445                 450                 455

Pro Leu Asp Val Tyr Lys Lys Pro Ser Gly Asn Ala
            460                 465

Phe Ser Arg Glu Thr Thr Ala Phe Asp Asn Lys Val
    470                 475                 480

Asn Ser Met Gln Thr Val Phe Val Gly Tyr Gly Pro
                485                 490

Thr Phe Lys Tyr Lys Thr Lys Val Pro Pro Phe Glu
            495                 500

Asn Ile Glu Leu Tyr Asn Val Met Cys Asp Leu Leu
505                 510                 515

Gly Leu Lys Pro Ala Pro Asn Asn Gly Thr His Gly
            520                 525

Ser Leu Asn His Leu Leu Arg Thr Asn Thr Phe Arg
    530                 535                 540

Pro Thr Met Pro Glu Glu Val Thr Arg Pro Asn Tyr
                545                 550

Pro Gly Ile Met Tyr Leu Gln Ser Asp Phe Asp Leu
            555                 560

Gly Cys Thr Cys Asp Asp Lys Val Glu Pro Lys Asn
565                 570                 575

Lys Leu Asp Glu Leu Asn Lys Arg Leu His Thr Lys
            580                 585

Gly Ser Thr Glu Glu Arg His Leu Leu Tyr Gly Asp
    590                 595                 600

Arg Pro Ala Val Leu Tyr Arg Thr Arg Tyr Asp Ile
                605                 610

Leu Tyr His Thr Asp Phe Glu Ser Gly Tyr Ser Glu
            615                 620

Ile Phe Leu Met Pro Leu Trp Thr Ser Tyr Thr Val
625                 630                 635

Ser Lys Gln Ala Glu Val Ser Ser Val Pro Asp His
            640                 645

Leu Thr Ser Cys Val Arg Pro Asp Val Arg Val Ser
650                 655                 660

Pro Ser Phe Ser Gln Asn Cys Leu Ala Tyr Lys Asn
            665                 670

Asp Lys Gln Met Ser Tyr Gly Phe Leu Phe Pro Pro
            675                 680

Tyr Leu Ser Ser Ser Pro Glu Ala Lys Tyr Asp Ala
685                 690                 695

Phe Leu Val Thr Asn Met Val Pro Met Tyr Pro Ala
                700                 705

Phe Lys Arg Val Trp Asn Tyr Phe Gln Arg Val Leu
            710                 715                 720

Val Lys Lys Tyr Ala Ser Glu Arg Asn Gly Val Asn
                725                 730

Val Ile Ser Gly Pro Ile Phe Asp Tyr Asp Tyr Asp
            735                 740

Gly Leu His Asp Thr Glu Asp Lys Ile Lys Gln Tyr
745                 750                 755
```

Val Glu Gly Ser Ser Ile Pro Val Pro Thr His Tyr
            760                 765

Tyr Ser Ile Ile Thr Ser Cys Leu Asp Phe Thr Gln
            770             775             780

Pro Ala Asp Lys Cys Asp Gly Pro Leu Ser Val Ser
                785             790

Ser Phe Ile Leu Pro His Arg Pro Asp Asn Glu Glu
            795             800

Ser Cys Asn Ser Ser Glu Asp Glu Ser Lys Trp Val
805             810              815

Glu Glu Leu Met Lys Met His Thr Ala Arg Val Arg
            820             825

Asp Ile Glu His Leu Thr Ser Leu Asp Phe Phe Arg
            830             835             840

Lys Thr Ser Arg Ser Tyr Pro Glu Ile Leu Thr Leu
                845             850

Lys Thr Tyr Leu His Thr Tyr Glu Ser Glu Ile Xaa
            855             860

Leu Ser Glu His Leu Gln Tyr Ser Leu Ile Asn Trp
865             870             875

Leu Tyr Ile Phe Ile Leu Phe Leu Tyr Leu Leu Ile
                880             885

Xaa Asn Gln Asp Ile Lys Asn Val Ser Ile Leu Ile
            890             895             900

Leu Tyr Gln Ile Xaa His Ile Met Pro Glu Xaa Leu
                905             910

His Cys Phe Ser Leu Met Leu Asp Leu Gly Ser Leu
            915             920

Val Phe Xaa Val Glu Leu Val Ile Asn Thr Ala Ala
925             930             935

Xaa Val Phe Ser Gly Ser Phe Xaa Met Val Leu Gln
                940             945

Ile Xaa Tyr Leu His Xaa Gly Asn Ile Asn Phe Pro
950             955             960

Met His Ser Cys His Ile Xaa Ser Cys Thr Val Trp
            965             970

Lys His Xaa Phe Cys Lys Val
            975

(2) INFORMATION FOR SEQ ID NO:39:

(i) SEQUENCE CHARACTERISTICS:
        (A) LENGTH:8
        (B) TYPE: amino acids
        (C) STRANDEDNESS: single
        (D) TOPOLOGY: linear (ii) MOLECULE TYPE:
        (A) DESCRIPTION: peptide (iii) HYPOTHETICAL: No (ix) FEATURE:
        (A) NAME/KEY: ATX-204
        (B) LOCATION:
        (C) IDENTIFICATION METHOD:
        (D) OTHER INFORMATION:

(xi) SEQUENCE DESCRIPTION: SEQ ID NO:39:

```
Met His Thr Ala Arg Val Arg Asp
                5

(2) INFORMATION FOR SEQ ID NO:40:

(i) SEQUENCE CHARACTERISTICS:
        (A) LENGTH: 8
        (B) TYPE:  amino acid
        (C) STRANDEDNESS:  single
        (D) TOPOLOGY:  linear (ii) MOLECULE TYPE:  peptide (iii) HYPOTHETICAL: No (ix) FEATURE:
        (A) NAME/KEY: ATX-205
        (B) LOCATION:
        (C) IDENTIFICATION METHOD:
        (D) OTHER INFORMATION:

(xi) SEQUENCE DESCRIPTION: SEQ ID NO:40:

Phe Ser Asn Asn Ala Lys Tyr Asp
                5

(2) INFORMATION FOR SEQ ID NO:41:

(i) SEQUENCE CHARACTERISTICS:
        (A) LENGTH:  7
        (B) TYPE:  amino acids
        (C) STRANDEDNESS:  single
        (D) TOPOLOGY:  linear (ii) MOLECULE TYPE:
        (A) DESCRIPTION:  Peptide (iii) HYPOTHETICAL: No (ix) FEATURE:
        (A) NAME/KEY: ATX-209
        (B) LOCATION:
        (C) IDENTIFICATION METHOD:
        (D) OTHER INFORMATION:

(xi) SEQUENCE DESCRIPTION: SEQ ID NO:41:

Val Met Pro Asn Ile Glu Lys
                5

(2) INFORMATION FOR SEQ ID NO:42:

(i) SEQUENCE CHARACTERISTICS:
        (A) LENGTH: 8
        (B) TYPE: amino acids
        (C) STRANDEDNESS:  single
        (D) TOPOLOGY:  linear (ii) MOLECULE TYPE:
        (A) DESCRIPTION:  Peptide (iii) HYPOTHETICAL: No (ix) FEATURE:
        (A) NAME/KEY: ATX-210
        (B) LOCATION:
        (C) IDENTIFICATION METHOD:
        (D) OTHER INFORMATION:

(xi) SEQUENCE DESCRIPTION: SEQ ID NO:42:

Thr Ala Arg Gly Trp Glu Cys Thr
                5
```

```
(2) INFORMATION FOR SEQ ID NO:43:

(i) SEQUENCE CHARACTERISTICS:
        (A) LENGTH:  11
        (B) TYPE:  amino acid
        (C) STRANDEDNESS:  single
        (D) TOPOLOGY:  linear (ii) MOLECULE TYPE:
        (A) DESCRIPTION: Peptide (iii) HYPOTHETICAL: No (ix) FEATURE:
        (A) NAME/KEY: ATX-212
        (B) LOCATION:
        (C) IDENTIFICATION METHOD:
        (D) OTHER INFORMATION:

(xi) SEQUENCE DESCRIPTION: SEQ ID NO:43:

Xaa Asp Ser Pro Trp Thr Xaa Ile Ser Gly Ser
                  5                  10

(2) INFORMATION FOR SEQ ID NO:44:

(i) SEQUENCE CHARACTERISTICS:
        (A) LENGTH:  11
        (B) TYPE:  amino acids
        (C) STRANDEDNESS:  single
        (D) TOPOLOGY:  linear (ii) MOLECULE TYPE:
        (A) DESCRIPTION: Peptide (iii) HYPOTHETICAL: No (ix) FEATURE:
        (A) NAME/KEY: ATX-214
        (B) LOCATION:
        (C) IDENTIFICATION METHOD:
        (D) OTHER INFORMATION:

(xi) SEQUENCE DESCRIPTION: SEQ ID NO:44:

Leu Arg Ser Cys Gly Thr His Ser Pro Tyr Met
                  5                  10

(2) INFORMATION FOR SEQ ID NO:45:

(i) SEQUENCE CHARACTERISTICS:
        (A) LENGTH:  8
        (B) TYPE:  amino acid
        (C) STRANDEDNESS:  single
        (D) TOPOLOGY:  linear (ii) MOLECULE TYPE:
        (A) DESCRIPTION: Peptide (iii) HYPOTHETICAL: No (ix) FEATURE:
        (A) NAME/KEY: ATX-215/34A
        (B) LOCATION:
        (C) IDENTIFICATION METHOD:
        (D) OTHER INFORMATION:

(xi) SEQUENCE DESCRIPTION: SEQ ID NO:45:

Thr Tyr Leu His Thr Tyr Glu Ser
                  5

(2) INFORMATION FOR SEQ ID NO:46:

(i) SEQUENCE CHARACTERISTICS:
        (A) LENGTH:  13
```

```
          (B) TYPE:  amino acids
          (C) STRANDEDNESS:  single
          (D) TOPOLOGY:  linear (ii) MOLECULE TYPE:
          (A) DESCRIPTION:  Peptide (iii) HYPOTHETICAL: No (ix) FEATURE:
          (A) NAME/KEY:
          (B) LOCATION:
          (C) IDENTIFICATION METHOD:
          (D) OTHER INFORMATION:

(xi) SEQUENCE DESCRIPTION: SEQ ID NO:46:

Ala Ile Ile Ala Asn Leu Thr Cys Lys Lys Pro Asp Gln
                 5                  10

(2) INFORMATION FOR SEQ ID NO:47:

(i) SEQUENCE CHARACTERISTICS:
          (A) LENGTH:  8
          (B) TYPE:  amino acids
          (C) STRANDEDNESS:  single
          (D) TOPOLOGY:  linear (ii) MOLECULE TYPE:
          (A) DESCRIPTION:  Peptide (iii) HYPOTHETICAL: No (ix) FEATURE:
          (A) NAME/KEY: ATX-216
          (B) LOCATION:
          (C) IDENTIFICATION METHOD:
          (D) OTHER INFORMATION:

(xi) SEQUENCE DESCRIPTION: SEQ ID NO:47:

Ile Val Gly Gln Leu Met Asp Gly
                 5

(2) INFORMATION FOR SEQ ID NO:48:

(i) SEQUENCE CHARACTERISTICS:
          (A) LENGTH:  9
          (B) TYPE:  amino acids
          (C) STRANDEDNESS:  single
          (D) TOPOLOGY:  linear (ii) MOLECULE TYPE:
          (A) DESCRIPTION:  Peptide (iii) HYPOTHETICAL: No (ix) FEATURE:
          (A) NAME/KEY: ATX-218/44
          (B) LOCATION:
          (C) IDENTIFICATION METHOD:
          (D) OTHER INFORMATION:

(xi) SEQUENCE DESCRIPTION: SEQ ID NO:48:

Thr Ser Arg Ser Tyr Pro Glu Ile Leu
                 5

(2) INFORMATION FOR SEQ ID NO:49:

(i) SEQUENCE CHARACTERISTICS:
          (A) LENGTH:  9
          (B) TYPE:  amino acids
          (C) STRANDEDNESS:  single
          (D) TOPOLOGY:  linear
```

(ii) MOLECULE TYPE:
        (A) DESCRIPTION: Peptide (iii) HYPOTHETICAL: No (ix) FEATURE:
        (A) NAME/KEY: ATX-223B/24
        (B) LOCATION:
        (C) IDENTIFICATION METHOD:
        (D) OTHER INFORMATION:

(xi) SEQUENCE DESCRIPTION: SEQ ID NO:49:

Gln Ala Glu Val Ser Ser Val Pro Asp
                5

(2) INFORMATION FOR SEQ ID NO:50:

(i) SEQUENCE CHARACTERISTICS:
        (A) LENGTH: 14
        (B) TYPE: amino acids
        (C) STRANDEDNESS: single
        (D) TOPOLOGY: linear (ii) MOLECULE TYPE:
        (A) DESCRIPTION: Peptide (iii) HYPOTHETICAL: No (ix) FEATURE:
        (A) NAME/KEY: ATX-224
        (B) LOCATION:
        (C) IDENTIFICATION METHOD:
        (D) OTHER INFORMATION:

(xi) SEQUENCE DESCRIPTION: SEQ ID NO:50:

Arg Cys Phe Glu Leu Gln Glu Ala Gly Pro Pro Asp Asp Cys
                5                   10

(2) INFORMATION FOR SEQ ID NO:51:

(i) SEQUENCE CHARACTERISTICS:
        (A) LENGTH: 12
        (B) TYPE: amino acid
        (C) STRANDEDNESS: single
        (D) TOPOLOGY: linear (ii) MOLECULE TYPE:
        (A) DESCRIPTION: Peptide (iii) HYPOTHETICAL: No (ix) FEATURE:
        (A) NAME/KEY: ATX-229
        (B) LOCATION:
        (C) IDENTIFICATION METHOD:
        (D) OTHER INFORMATION:

(xi) SEQUENCE DESCRIPTION: SEQ ID NO:51:

Ser Tyr Thr Ser Cys Cys His Asp Phe Asp Glu Leu
                5                   10

(2) INFORMATION FOR SEQ ID NO:52:

(i) SEQUENCE CHARACTERISTICS:
        (A) LENGTH: 16
        (B) TYPE: amino acid
        (C) STRANDEDNESS: single
        (D) TOPOLOGY: linear (ii) MOLECULE TYPE:
        (A) DESCRIPTION: Peptide (iii) HYPOTHETICAL: No

```
       (ix) FEATURE:
             (A) NAME/KEY: ATX-224/53
             (B) LOCATION:
             (C) IDENTIFICATION METHOD:
             (D) OTHER INFORMATION:

(xi) SEQUENCE DESCRIPTION: SEQ ID NO:52:

Gln Met Ser Tyr Gly Phe Leu Phe Pro Pro Tyr Leu
 1               5                  10

Ser Ser Ser Pro
        15

(2) INFORMATION FOR SEQ ID NO:53:

(i) SEQUENCE CHARACTERISTICS:
             (A) LENGTH:  117
             (B) TYPE:  nucleic acid
             (C) STRANDEDNESS:  single
             (D) TOPOLOGY:  Unknown (ii) MOLECULE TYPE:
             (A) DESCRIPTION:  cDNA (iii) HYPOTHETICAL: No (iv) ANTI-SENSE:

(vi) ORIGINAL SOURCE:
             (A) ORGANISM: Human
             (B) STRAIN:
             (C) INDIVIDUAL ISOLATE:
             (D) DEVELOPMENTAL STAGE:
             (E) HAPLOTYPE:
             (F) TISSUE TYPE: Liver
             (G) CELL TYPE:
             (H) CELL LINE:
             (I) ORGANELLE:

(ix) FEATURE:
             (A) NAME/KEY:
             (B) LOCATION:
             (C) IDENTIFICATION METHOD:
             (D) OTHER INFORMATION: 5' end of human liver
                 ATX gene (xi) SEQUENCE DESCRIPTION: SEQ ID NO:53:

ATGGCAAGGA GGAGCTCGTT CCAGTCGTGT CAAGATATAT                    40

CCCTGTTCAC TTTTGCCGTT GGAGTCAATA TCTGCTTAGG                    80

ATTCACTGCA CATCGAATTA AGAGAGCAGA AGGATGG                      117

(2) INFORMATION FOR SEQ ID NO:54:

(i) SEQUENCE CHARACTERISTICS:
             (A) LENGTH:  39
             (B) TYPE:  amino acids
             (C) STRANDEDNESS:  single
             (D) TOPOLOGY:  Unknown (ii) MOLECULE TYPE:
             (A) DESCRIPTION:  Peptide (iii) HYPOTHETICAL: No (v) FRAGMENT TYPE: N-terminal fragment (vi) ORIGINAL SOURCE:
             (A) ORGANISM: Human
             (B) STRAIN:
             (C) INDIVIDUAL ISOLATE:
             (D) DEVELOPMENTAL STAGE:
             (E) HAPLOTYPE:
```

```
            (F) TISSUE TYPE: Liver
            (G) CELL TYPE:
            (H) CELL LINE:
            (I) ORGANELLE:

(ix) FEATURE:
            (A) NAME/KEY:
            (B) LOCATION:
            (C) IDENTIFICATION METHOD:
            (D) OTHER INFORMATION: N-terminal region
                including transmembrane domain of liver
                ATX protein (xi) SEQUENCE DESCRIPTION: SEQ ID NO:54:

Met Ala Arg Arg Ser Ser Phe Gln Ser Cys Gln Asp
 1               5                  10

Ile Ser Leu Phe Thr Phe Ala Val Gly Val Asn Ile
            15                  20

Cys Leu Gly Phe Thr Ala His Arg Ile Lys Arg Ala
 25                  30                  35

Glu Gly Trp (2) INFORMATION FOR SEQ ID NO:55:

(i) SEQUENCE CHARACTERISTICS:
            (A) LENGTH: 21
            (B) TYPE: nucleic acid
            (C) STRANDEDNESS: single
            (D) TOPOLOGY: linear (ii) MOLECULE TYPE: cDNA (iii) HYPOTHETICAL: No (iv) ANTI-SENSE: Yes (ix) FEATURE:
            (A) NAME/KEY:
            (B) LOCATION:
            (C) IDENTIFICATION METHOD:
            (D) OTHER INFORMATION: Primer from 5' end of
                4C11

(xi) SEQUENCE DESCRIPTION: SEQ ID NO:55:

GCTCAGATAA GGAGGAAAGA G                                              21

(2) INFORMATION FOR SEQ ID NO:56:

(i) SEQUENCE CHARACTERISTICS:
            (A) LENGTH: 21
            (B) TYPE: nucleic acid
            (C) STRANDEDNESS: single
            (D) TOPOLOGY: linear (ii) MOLECULE TYPE: cDNA (iii) HYPOTHETICAL: No (iv) ANTI-SENSE: Yes (ix) FEATURE:
            (A) NAME/KEY:
            (B) LOCATION:
            (C) IDENTIFICATION METHOD:
            (D) OTHER INFORMATION: Nested primers from
                4C11

(xi) SEQUENCE DESCRIPTION: SEQ ID NO:56:

GAATCCGTAG GACATCTGCT T                                              21
```

(2) INFORMATION FOR SEQ ID NO:57:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: Yes (ix) FEATURE:
        (A) NAME/KEY:
        (B) LOCATION:
        (C) IDENTIFICATION METHOD:
        (D) OTHER INFORMATION: Nested primers from
            4C11

(xi) SEQUENCE DESCRIPTION: SEQ ID NO:57:

TGTAGGCCAA ACAGTTCTGA C                                         21

(2) INFORMATION FOR SEQ ID NO:58:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: No (ix) FEATURE:
        (A) NAME/KEY:
        (B) LOCATION:
        (C) IDENTIFICATION METHOD:
        (D) OTHER INFORMATION: Nested sense primer
            deduced from ATX-101, wherein N is
            inosine (xi) SEQUENCE DESCRIPTION: SEQ ID NO:58:

AAYTCNATGC ARACNGTNTT YGTNG                                     25

(2) INFORMATION FOR SEQ ID NO:59:

(i) SEQUENCE CHARACTERISTICS:
        (A) LENGTH: 26
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: No (ix) FEATURE:
        (A) NAME/KEY:
        (B) LOCATION:
        (C) IDENTIFICATION METHOD:
        (D) OTHER INFORMATION: Nested primer of ATX
            -101, wherein N is inosine (xi) SEQUENCE DESCRIPTION: SEQ ID NO:59:

TTYGTNGGNT AYGGNCCNAC NTTYAA                                    26

(2) INFORMATION FOR SEQ ID NO:60:

(i) SEQUENCE CHARACTERISTICS:
        (A) LENGTH:  26
        (B) TYPE:  nucleic acid
        (C) STRANDEDNESS:  single
        (D) TOPOLOGY:  linear (ii) MOLECULE TYPE:  cDNA (iii) HYPOTHETICAL:  No (iv) ANTI-SENSE:  No (ix) FEATURE:
        (A) NAME/KEY:
        (B) LOCATION:
        (C) IDENTIFICATION METHOD:
        (D) OTHER INFORMATION: Nested primer deduced
            from ATX-103, wherein N is inosine (xi) SEQUENCE DESCRIPTION: SEQ ID NO:60:

AAYTAYCTNA CNAAYGTNGA YGAYAT                                    26

(2) INFORMATION FOR SEQ ID NO:61:

(i) SEQUENCE CHARACTERISTICS:
        (A) LENGTH:  26
        (B) TYPE:  nucleic acid
        (C) STRANDEDNESS:  single
        (D) TOPOLOGY:  linear (ii) MOLECULE TYPE:  cDNA (iii) HYPOTHETICAL:  No (iv) ANTI-SENSE:  No (ix) FEATURE:
        (A) NAME/KEY:
        (B) LOCATION:
        (C) IDENTIFICATION METHOD:
        (D) OTHER INFORMATION: Nested primer deduced
            from ATX-103, wherein N is inosine (xi) SEQUENCE DESCRIPTION: SEQ ID NO:61:

GAYGAYATNA CNCTNGTNCC NGGNAC                                    26

(2) INFORMATION FOR SEQ ID NO:62:

(i) SEQUENCE CHARACTERISTICS:
        (A) LENGTH:  29
        (B) TYPE:  nucleic acid
        (C) STRANDEDNESS:  single
        (D) TOPOLOGY:  linear (ii) MOLECULE TYPE:  cDNA (iii) HYPOTHETICAL:  No (iv) ANTI-SENSE:  No (ix) FEATURE:
        (A) NAME/KEY:
        (B) LOCATION:
        (C) IDENTIFICATION METHOD:
        (D) OTHER INFORMATION: Nested primer deduced
            from ATX-103, wherein N is inosine (xi) SEQUENCE DESCRIPTION: SEQ ID NO:62:

TGYTTYGARY TNCARGARGC NGGNCCNCC                                 29

(2) INFORMATION FOR SEQ ID NO:63:

-continued (i) SEQUENCE CHARACTERISTICS:
        (A) LENGTH:  18
        (B) TYPE:  nucleic acid
        (C) STRANDEDNESS:  single
        (D) TOPOLOGY:  linear (ii) MOLECULE TYPE: cDNA (iii) HYPOTHETICAL: No (xi) SEQUENCE DESCRIPTION: SEQ ID NO:63:

GCTGTCTTCA AACACAGC                                                 18

(2) INFORMATION FOR SEQ ID NO:64:

(i) SEQUENCE CHARACTERISTICS:
        (A) LENGTH:  21
        (B) TYPE:  nucleic acid
        (C) STRANDEDNESS:  single
        (D) TOPOLOGY:  linear (ii) MOLECULE TYPE: cDNA (iii) HYPOTHETICAL: No (xi) SEQUENCE DESCRIPTION: SEQ ID NO:64:

CTGGTGGCTG TAATCCATAG C                                             21

(2) INFORMATION FOR SEQ ID NO:65:

(i) SEQUENCE CHARACTERISTICS:
        (A) LENGTH:  21
        (B) TYPE:  nucleic acid
        (C) STRANDEDNESS:  single
        (D) TOPOLOGY:  linear (ii) MOLECULE TYPE: cDNA (iii) HYPOTHETICAL: No (iv) ANTI-SENSE:  No (ix) FEATURE:
        (A) NAME/KEY:
        (B) LOCATION:
        (C) IDENTIFICATION METHOD:
        (D) OTHER INFORMATION: Primer for 5' end of
            N-tera 2D1 sequence (xi) SEQUENCE DESCRIPTION: SEQ ID NO:65:

CGTGAAGGCA AAGAGAACAC G                                             21

(2) INFORMATION FOR SEQ ID NO:66:

(i) SEQUENCE CHARACTERISTICS:
        (A) LENGTH:  3104
        (B) TYPE:  nucleic acid
        (C) STRANDEDNESS:  double
        (D) TOPOLOGY:  Unknown (ii) MOLECULE TYPE: cDNA (iii) HYPOTHETICAL: No (ix) FEATURE:
        (A) NAME/KEY:  N-tera 2D1 ATX cDNA
        (B) LOCATION:
        (C) IDENTIFICATION METHOD:
        (D) OTHER INFORMATION:

(xi) SEQUENCE DESCRIPTION: SEQ ID NO:66:

-continued

```
AGTGCACTCC GTGAAGGCAA AGAGAACACG CTGCAAAAGG            40
CTTTCCAATA ATCCTCGACA TGGCAAGGAG GAGCTCGTTC            80
CAGTCGTGTC AGATAATATC CCTGTTCACT TTTGCCGTTG           120
GAGTCAATAT CTGCTTAGGA TTCACTGCAC ATCGAATTAA           160
GAGAGCAGAA GGATGGGAGG AAGGTCCTCC TACAGTGCTA           200
TCAGACTCCC CCTGGACCAA CATCTCCGGA TCTTGCAAGG           240
GCAGGTGCTT TGAACTTCAA GAGGCTGGAC CTCCTGATTG           280
TCGCTGTGAC AACTTGTGTA AGAGCTATAC CAGTTGCTGC           320
CATGACTTTG ATGAGCTGTG TTTGAAGACA GCCCGTGCGT           360
GGGAGTGTAC TAAGGACAGA TGTGGAGAAG TCAGAAATGA           400
AGAAAATGCC TGTCACTGCT CAGAGGACTG CTTGGCCAGG           440
GGAGACTGCT GTACCAATTA CCAAGTGGTT TGCAAAGGAG           480
AGTCGCATTG GGTTGATGAT GACTGTGAGG AAATAAAGGC           520
CGCAGAATGC CCTGCAGGGT TTGTTCGCCC TCCATTAATC           560
ATCTTCTCCG TGGATGGCTT CCGTGCATCA TACATGAAGA           600
AAGGCAGCAA AGTCATGCCT AATATTGAAA AACTAAGGTC           640
TTGTGGCACA CACTCGCCCC ACATGAGGCC GGTGTACCCA           680
ACTAAAACCT TTCCTAACTT ATACACTTTG GCCACTGGGC           720
TATATCCAGA ATCACATGGA ATTGTTGGCA ATTCAATGTA           760
TGATCCTGTA TTTGATGCCA CTTTTCATCT GCGAGGGCGA           800
GAGAAATTTA ATCATAGATG GTGGGAGGT CAACCGCTAT            840
GGATTACAGC CACCAAGCAA AGGGGTGAAA GCTGGAACAT           880
TCTTTTGGTC TGTTGTCATC CCTCACGAGC GGAGATATTA           920
ACCATATTGC AGTGGCTCAC CCTGCCAGAT CATGAGAGGC           960
TTCGGTCTAT GCCTTCTATT CTGAGCAACC TGATTTCTCT         1000
GGACACAAAT ATGCCTTTCG GCCCTGAGAT GACAAATCCT          1040
CTGAGGGAAA TCGACAAAAT TGTGGGGCAA TTAATGGATG          1080
GACTGAAACA ACTAAAACTG CATCGGTGTG TCAACGTCAT          1120
CTTTGTCGGA GACCATGGAA TGGAAGATGT CACATGTGAT          1160
AGAACTGAGT TCTTGAGTAA TTACCTAACT AATGTGGATG          1200
ATATTACTTT AGTGCCTGGA ACTCTAGGAA TTCGATCCAA          1240
ATTTAGCAAC AATGCTAAAT ATGACCCCAA AGCCATTATT          1280
GCCAATCTCA CGTGTAAAAA ACCAGATCAG CACTTTAAGC          1320
CTTACTTGAA ACAGCACCTT CCCAAACGTT TGCACTATGC          1360
CAACAACAGA AGAATTGAGG ATATCCATTT ATTGGTGGAA          1400
CGCAGATGGC ATGTTGCAAG GAAACCTTTG GATGTTTATA          1440
AGAAACCATC AGGAAAATGC TTTTTCCAGG GAGACCACGG          1480
ATTTGATAAC AAGGTCAACA GCATGCAGAC TGTTTTTGTA          1520
GGTTATGGCC CAACATTTAA GTACAAGACT AAAGTGCCTC          1560
CATTTGAAAA CATTGAACTT TACAATGTTA TGTGTGATCT          1600
```

```
CCTGGGATTG AAGCCAGCTC CTAATAATGG GACCCATGGA          1640

AGTTTGAATC ATCTCCTGCG CACTAATACC TTCAGGCCAA          1680

CCATGCCAGA GGAAGTTACC AGACCCAATT ATCCAGGGAT          1720

TATGTACCTT CAGTCTGATT TTGACCTGGG CTGCACTTGT          1760

GATGATAAGG TAGAGCCAAA GAACAAGTTG GATGAACTCA          1800

ACAAACGGCT TCATACAAAA GGGTCTACAG AAGAGAGACA          1840

CCTCCTCTAT GGGCGACCTG CAGTGCTTTA TCGGACTAGA          1880

TATGATGTCT TATATCACAC TGACTTTGAA AGTGGTTATA          1920

GTGAAATATT CCTAATGCCA CTCTGGACAT CATATACTGT          1960

TTCCAAACAG GCTGAGGTTT CCAGCGTTCC TGACCATCTG          2000

ACCAGTTGCG TCCGGCCTGA TGTCCGTGTT CTCCGAGTT           2040

TCAGTCAGAA CTGTTTGGCC TACAAAAATG ATAAGCAGAT          2080

GTCCTACGGA TTCCTCTTTC CTCCTTATCT GAGCTCTTCA          2120

CCAGAGGCTA AATATGATGC ATTCCTTGTA ACCAATATGG          2160

TTCCAATGTA TCCTGCTTTC AAACGGGTCT GGAATTATTT          2200

CCAAAGGGTA TTGGTGAAGA AATATGCTTC GGAAAGAAAT          2240

GGAGTTAACG TGATAAGTGG ACCAATCTTC GACTATGACT          2280

ATGATGGCTT ACATGACACA GAAGACAAAA TAAAACAGTA          2320

CGTGGAAGGC AGTTCCATTC CTGTTCCAAC TCACTACTAC          2360

AGCATCATCA CCAGCTGTCT GGATTTCACT CAGCCTGCCG          2400

ACAAGTGTGA CGGCCCTCTC TCTGTGTCCT CCTTCATCCT          2440

CCGTCACCGG CCTGACAACG AGGAGAGCTG CAATAGCTCA          2480

GAGGACGAAT CAAAATGGGT AGAAGAACTC ATGAAGATGC          2520

ACACGGCTAG GGTGCGTGAC ATTGAACATC TCACCAGCCT          2560

GGACTTCTTC CGAAAGACCA GCCGCAGCTA CCCAGAAATC          2600

CTGACACTCA AGACATACCT GCATACATAT GAGAGCGAGA          2640

TTTAACTTTC TGAGCATCTG CAGTACAGTC TTATCAACTG          2680

GTTGTATATT TTTATATTGT TTTTGTATTT ATTAATTTGA          2720

AACCAGGACA TTAAAAATGT TAGTATTTTA ATCCTGTACC          2760

AAATCTGACA TATTATGCCT GAATGACTCC ACTGTTTTTC          2800

TCTAATGCTT GATTTAGGTA GCCTTGTGTT CTGAGTAGAG          2840

CTTGTAATAA ATACTGCAGC TTGAGTTTTT AGTGGAAGCT          2880

TCTAAATGGT GCTGCAGATT TGATATTTGC ATTGAGGAAA          2920

TATTAATTTT CCAATGCACA GTTGCCACAT TTAGTCCTGT          2960

ACTGTATGGA AACACTGATT TTGTAAAGTT GCCTTTATTT          3000

GCTGTTAACT GTTAACTATG ACAGATATAT TTAAGCCTTA          3040

TAAACCAATC TTAAACATAA TAAATCACAC ATTCAGTTTT          3080

TTCTGGTAAA AAAAAAAAAA AAAA                          3104
```

(2) INFORMATION FOR SEQ ID NO:67:

(i) SEQUENCE CHARACTERISTICS:
    (A) LENGTH: 861
    (B) TYPE: amino acid
    (C) STRANDEDNESS: single
    (D) TOPOLOGY: Unknown (ii) MOLECULE TYPE: protein (iii) HYPOTHETICAL: No (ix) FEATURE:
    (A) NAME/KEY: N-tera 2D1 ATX protein
    (B) LOCATION:
    (C) IDENTIFICATION METHOD:
    (D) OTHER INFORMATION:

(xi) SEQUENCE DESCRIPTION: SEQ ID NO:67:

```
Met Ala Arg Arg Ser Ser Phe Gln Ser Cys Gln Ile Ile Ser Leu Phe
 1               5                  10                  15

Thr Phe Ala Val Gly Val Asn Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
    50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Ala Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
    130                 135                 140

Val Asp Asp Asp Cys Glu Glu Ile Lys Ala Ala Glu Cys Pro Ala Gly
145                 150                 155                 160

Phe Val Arg Pro Pro Leu Ile Ile Phe Ser Val Asp Gly Phe Arg Ala
                165                 170                 175

Ser Tyr Met Lys Lys Gly Ser Lys Val Met Pro Asn Ile Glu Lys Leu
            180                 185                 190

Arg Ser Cys Gly Thr His Ser Pro His Met Arg Pro Val Tyr Pro Thr
        195                 200                 205

Lys Thr Phe Pro Asn Leu Tyr Thr Leu Ala Thr Gly Leu Tyr Pro Glu
    210                 215                 220

Ser His Gly Ile Val Gly Asn Ser Met Tyr Asp Pro Val Phe Asp Ala
225                 230                 235                 240

Thr Phe His Leu Arg Gly Arg Glu Lys Phe Asn His Arg Trp Trp Gly
                245                 250                 255

Gly Gln Pro Leu Trp Ile Thr Ala Thr Lys Gln Arg Gly Glu Ser Trp
            260                 265                 270

Asn Ile Leu Leu Val Cys Cys His Pro Ser Arg Ala Glu Ile Leu Thr
        275                 280                 285

Ile Leu Gln Trp Leu Thr Leu Pro Asp His Glu Arg Leu Arg Ser Met
    290                 295                 300

Pro Ser Ile Leu Ser Asn Leu Ile Ser Leu Asp Thr Asn Met Pro Phe
305                 310                 315                 320
```

-continued

```
Gly Pro Glu Met Thr Asn Pro Leu Arg Glu Ile Asp Lys Ile Val Gly
                325                 330                 335

Gln Leu Met Asp Gly Leu Lys Gln Leu Lys Leu His Arg Cys Val Asn
            340                 345                 350

Val Ile Phe Val Gly Asp His Gly Met Glu Asp Val Thr Cys Asp Arg
        355                 360                 365

Thr Glu Phe Leu Ser Asn Tyr Leu Thr Asn Val Asp Asp Ile Thr Leu
    370                 375                 380

Val Pro Gly Thr Leu Gly Ile Arg Ser Lys Phe Ser Asn Asn Ala Lys
385                 390                 395                 400

Tyr Asp Pro Lys Ala Ile Ile Ala Asn Leu Thr Cys Lys Lys Pro Asp
                405                 410                 415

Gln His Phe Lys Pro Tyr Leu Lys Gln His Leu Pro Lys Arg Leu His
            420                 425                 430

Tyr Ala Asn Asn Arg Arg Ile Glu Asp Ile His Leu Leu Val Glu Arg
        435                 440                 445

Arg Trp His Val Ala Arg Lys Pro Leu Asp Val Tyr Lys Lys Pro Ser
    450                 455                 460

Gly Lys Cys Phe Phe Gln Gly Asp His Gly Phe Asp Asn Lys Val Asn
465                 470                 475                 480

Ser Met Gln Thr Val Phe Val Gly Tyr Gly Pro Thr Phe Lys Tyr Lys
                485                 490                 495

Thr Lys Val Pro Pro Phe Glu Asn Ile Glu Leu Tyr Asn Val Met Cys
            500                 505                 510

Asp Leu Leu Gly Leu Lys Pro Ala Pro Asn Asn Gly Thr His Gly Ser
        515                 520                 525

Leu Asn His Leu Leu Arg Thr Asn Thr Phe Arg Pro Thr Met Pro Glu
    530                 535                 540

Glu Val Thr Arg Pro Asn Tyr Pro Gly Ile Met Tyr Leu Gln Ser Asp
445                 450                 555                 560

Phe Asp Leu Gly Cys Thr Cys Asp Asp Lys Val Glu Pro Lys Asn Lys
                565                 570                 575

Leu Asp Glu Leu Asn Lys Arg Leu His Thr Lys Gly Ser Thr Glu Glu
            580                 585                 590

Arg His Leu Leu Tyr Gly Arg Pro Ala Val Leu Tyr Arg Thr Arg Tyr
        595                 600                 605

Asp Val Leu Tyr His Thr Asp Phe Glu Ser Gly Tyr Ser Glu Ile Phe
    610                 615                 620

Leu Met Pro Leu Trp Thr Ser Tyr Thr Val Ser Lys Gln Ala Glu Val
625                 630                 635                 640

Ser Ser Val Pro Asp His Leu Thr Ser Cys Val Arg Pro Asp Val Arg
                645                 650                 655

Val Ser Pro Ser Phe Ser Gln Asn Cys Leu Ala Tyr Lys Asn Asp Lys
            660                 665                 670

Gln Met Ser Tyr Gly Phe Leu Phe Pro Pro Tyr Leu Ser Ser Ser Pro
        675                 680                 685

Glu Ala Lys Tyr Asp Ala Phe Leu Val Thr Asn Met Val Pro Met Tyr
    690                 695                 700

Pro Ala Phe Lys Arg Val Trp Asn Tyr Phe Gln Arg Val Leu Val Lys
705                 710                 715                 720

Lys Tyr Ala Ser Glu Arg Asn Gly Val Asn Val Ile Ser Gly Pro Ile
                725                 730                 735

Phe Asp Tyr Asp Tyr Asp Gly Leu His Asp Thr Glu Asp Lys Ile Lys
```

|  | 740 | | | | 745 | | | | 750 | | |
|---|---|---|---|---|---|---|---|---|---|---|---|
| Gln | Tyr | Val | Glu | Gly | Ser | Ser | Ile | Pro | Val | Pro | Thr | His | Tyr | Tyr | Ser |
|  |  |  | 755 |  |  |  | 760 |  |  |  | 765 |  |  |  |  |

Ile Ile Thr Ser Cys Leu Asp Phe Thr Gln Pro Ala Asp Lys Cys Asp
770                     775                 780

Gly Pro Leu Ser Val Ser Ser Phe Ile Leu Arg His Arg Pro Asp Asn
785                 790                 795                 800

Glu Glu Ser Cys Asn Ser Ser Glu Asp Ser Lys Trp Val Glu Glu
            805                 810                 815

Leu Met Lys Met His Thr Ala Arg Val Arg Asp Ile Glu His Leu Thr
                820                 825                 830

Ser Leu Asp Phe Phe Arg Lys Thr Ser Arg Ser Tyr Pro Glu Ile Leu
            835                 840                 845

Thr Leu Lys Thr Tyr Leu His Thr Tyr Glu Ser Glu Ile
850                 855                 860

(2) INFORMATION FOR SEQ ID NO:68:

(i) SEQUENCE CHARACTERISTICS:
        (A) LENGTH: 3251
        (B) TYPE: nucleic acid
        (C) STRANDEDNESS: double
        (D) TOPOLOGY: Unknown (ii) MOLECULE TYPE: cDNA (iii) HYPOTHETICAL: No (ix) FEATURE:
        (A) NAME/KEY: A2058 ATX cDNA
        (B) LOCATION:
        (C) IDENTIFICATION METHOD:
        (D) OTHER INFORMATION:

(xi) SEQUENCE DESCRIPTION: SEQ ID NO:68:

| | |
|---|---:|
| CGTGAAGGCA AAGAGAACAC GCTGCAAAAG GCTTCCAAGA | 40 |
| ATCCTCGACA TGGCAAGGAG GAGCTCGTTC CAGTCGTGTC | 80 |
| AGATAATATC CCTGTTCACT TTTGCCGTTG GAGTCAGTAT | 120 |
| CTGCTTAGGA TTCACTGCAC ATCGAATTAA GAGAGCAGAA | 160 |
| GGATGGGAGG AAGGTCCTCC TACAGTGCTA TCAGACTCCC | 200 |
| CCTGGACCAA CATCTCCGGA TCTTGCAAGG GCAGGTGCTT | 240 |
| TGAACTTCAA GAGGCTGGAC CTCCTGATTG TCGCTGTGAC | 280 |
| AACTTGTGTA AGAGCTATAC CAGTTGCTGC CATGACTTTG | 320 |
| ATGAGCTGTG TTTGAAGACA GCCCGTGGCT GGGAGTGTAC | 360 |
| TAAGGACAGA TGTGGAGAAG TCAGAAATGA AGAAAATGCC | 400 |
| TGTCACTGCT CAGAGGACTG CTTGGCCAGG GGAGACTGCT | 440 |
| GTACCAATTA CCAAGTGGTT TGCAAAGGAG AGTCGCATTG | 480 |
| GGTTGATGAT GACTGTGAGG AAATAAAGGC CGCAGAATGC | 520 |
| CCTGCAGGGT TTGTTCGCCC TCCATTAATC ATCTTCTCCG | 560 |
| TGGATGGCTT CCGTGCATCA TACATGAAGA AAGGCAGCAA | 600 |
| AGTCATGCCT AATATTGAAA AACTAAGGTC TTGTGGCACA | 640 |
| CACTCTCCCT ACATGAGGCC GGTGTACCCA ACTAAAACCT | 680 |
| TTCCTAACTT ATACACTTTG GCCACTGGGC TATATCCAGA | 720 |

| | |
|---|---|
| ATCACATGGA ATTGTTGGCA ATTCAATGTA TGATCCTGTA | 760 |
| TTTGATGCCA CTTTTCATCT GCGAGGGCGA GAGAAATTTA | 800 |
| ATCATAGATG GTGGGAGGT CAACCGCTAT GGATTACAGC | 840 |
| CACCAAGCAA GGGGTGAAAG CTGGAACATT CTTTTGGTCT | 880 |
| GTTGTCATCC CTCACGAGCG GAGAATATTA ACCATATTGC | 920 |
| GGTGGCTCAC CCTGCCAGAT CATGAGAGGC CTTCGGTCTA | 960 |
| TGCCTTCTAT TCTGAGCAAC CTGATTTCTC TGGACACAAA | 1000 |
| TATGGCCCTT TCGGCCCTGA GGAGAGTAGT TATGGCTCAC | 1040 |
| CTTTTACTCC GGCTAAGAGA CCTAAGAGGA AAGTTGCCCC | 1080 |
| TAAGAGGAGA CAGGAAAGAC CAGTTGCTCC TCCAAAGAAA | 1120 |
| AGAAGAAGAA AAATACATAG GATGGATCAT TATGCTGCGG | 1160 |
| AAACTCGTCA GGACAAAATG ACAAATCCTC TGAGGGAAAT | 1200 |
| CGACAAAATT GTGGGCAAT TAATGGATGG ACTGAAACAA | 1240 |
| CTAAAACTGC GTCGGTGTGT CAACGTCATC TTTGTCGGAG | 1280 |
| ACCATGGAAT GGAAGATGTC ACATGTGATA GAACTGAGTT | 1320 |
| CTTGAGTAAT TACCTAACTA ATGTGGATGA TATTACTTTA | 1360 |
| GTGCCTGGAA CTCTAGGAAG AATTCGATCC AAATTTAGCA | 1400 |
| ACAATGCTAA ATATGACCCC AAAGCCATTA TTGCCAATCT | 1440 |
| CACGTGTAAA AAACCAGATC AGCACTTTAA GCCTTACTTG | 1480 |
| AAACAGCACC TTCCCAAACG TTTGCACTAT GCCAACAACA | 1520 |
| GAAGAATTGA GGATATCCAT TTATTGGTGG AACGCAGATG | 1560 |
| GCATGTTGCA AGGAAACCTT TGGATGTTTA TAAGAAACCA | 1600 |
| TCAGGAAAAT GCTTTTTCCA GGGAGACCAC GGATTTGATA | 1640 |
| ACAAGGTCAA CAGCATGCAG ACTGTTTTTG TAGGTTATGG | 1680 |
| CCCAACATTT AAGTACAAGA CTAAAGTGCC TCCATTTGAA | 1720 |
| AACATTGAAC TTTACAATGT TATGTGTGAT CTCCTGGGAT | 1760 |
| TGAAGCCAGC TCCTAATAAT GGGACCCATG GAAGTTTGAA | 1800 |
| TCATCTCCTG CGCACTAATA CCTTCAGGCC AACCATGCCA | 1840 |
| GAGGAAGTTA CCAGACCCAA TTATCCAGGG ATTATGTACC | 1880 |
| TTCAGTCTGA TTTTGACCTG GCTGCACTT GTGATGATAA | 1920 |
| GGTAGAGCCA AAGAACAAGT TGGATGAACT CAACAAACGG | 1960 |
| CTTCATACAA AAGGGTCTAC AGAAGAGAGA CACCTCCTCT | 2000 |
| ATGGGCGACC TGCAGTGCTT TATCGGACTA GATATGATAT | 2040 |
| CTTATATCAC ACTGACTTTG AAAGTGGTTA TAGTGAAATA | 2080 |
| TTCCTAATGC TACTCTGGAC ATCATATACT GTTTCCAAAC | 2120 |
| AGGCTGAGGT TTCCAGCGTT CCTGACCATC TGACCAGTTG | 2160 |
| CGTCCGGCCT GATGTCCGTG TTTCTCCGAG TTTCAGTCAG | 2200 |
| AACTGTTTGG CCTACAAAAA TGATAAGCAG ATGTCCTACG | 2240 |
| GATTCCTCTT TCCTCCTTAT CTGAGCTCTT CACCAGAGGC | 2280 |

```
TAAATATGAT GCATTCCTTG TAACCAATAT GGTTCCAATG                       2320

TATCCTGCTT TCAAACGGGT CTGGAATTAT TTCCAAAGGG                       2360

TATTGGTGAA GAAATATGCT TCGGAAAGAA ATGGAGTTAA                       2400

CGTGATAAGT GGACCAATCT TCGACTATGA CTATGATGGC                       2440

TTACATGACA CAGAAGACAA AATAAAACAG TACGTGGAAG                       2480

GCAGTTCCAT TCCTGTTCCA ACTCACTACT ACAGCATCAT                       2520

CACCAGCTGT CTGGATTTCA CTCAGCCTGC CGACAAGTGT                       2560

GACGGCCCTC TCTCTGTGTC CTCCTTCATC CTGCCTCACC                       2600

GGCCTGACAA CGAGGAGAGC TGCAATAGCT CAGAGGACGA                       2640

ATCAAAATGG GTAGAAGAAC TCATGAAGAT GCACACAGCT                       2680

AGGGTGCGTG ACATTGAACA TCTCACCAGC CTGGACTTCT                       2720

TCCGAAAGAC CAGCCGCAGC TACCCAGAAA TCCTGACACT                       2760

CAAGACATAC CTGCATACAT ATGAGAGCGA GATTTAACTT                       2800

TCTGAGCATC TGCAGTACAG TCTTATCAAC TGGTTGTATA                       2840

TTTTTATATT GTTTTTGTAT TTATTAATTT GAAACCAGGA                       2880

CATTAAAAAT GTTAGTATTT TAATCCTGTA CCAAATCTGA                       2920

CATATTATGC CTGAATGACT CCACTGTTTT TCTCTAATGC                       2960

TTGATTTAGG TAGCCTTGTG TTCTGAGTAG AGCTTGTAAT                       3000

AAATACTGCA GCTTGAGAAA AAGTGGAAGC TTCTAAATGG                       3040

TGCTGCAGAT TTGATATTTG CATTGAGGAA ATATTAATTT                       3080

TCCAATGCAC AGTTGCCACA TTTAGTCCTG TACTGTATGG                       3120

AAACACTGAT TTTGTAAAGT TGCCTTTATT TGCTGTTAAC                       3160

TGTTAACTAT GACAGATATA TTTAAGCCTT ATAAACCAAT                       3200

CTTAAACATA ATAAATCACA CATTCAGTTT TAAAAAAAAA                       3240

AAAAAAAAAA A                                                      3251

(2) INFORMATION FOR SEQ ID NO:69:

(i) SEQUENCE CHARACTERISTICS:
        (A) LENGTH: 915
        (B) TYPE: amino acid
        (C) STRANDEDNESS: single
        (D) TOPOLOGY: Unknown (ii) MOLECULE TYPE: cDNA (iii) HYPOTHETICAL: No (ix) FEATURE:
        (A) NAME/KEY: A2058 ATX protein
        (B) LOCATION:
        (C) IDENTIFICATION METHOD:
        (D) OTHER INFORMATION:

(xi) SEQUENCE DESCRIPTION: SEQ ID NO:69:

Met Ala Arg Arg Ser Ser Phe Gln Ser Cys Gln Ile
 1               5                  10

Ile Ser Leu Phe Thr Phe Ala Val Gly Val Ser Ile
            15                  20

Cys Leu Gly Phe Thr Ala His Arg Ile Lys Arg Ala
25                  30                  35
```

-continued

```
Glu Gly Trp Glu Gly Pro Pro Thr Val Leu Ser
            40              45

Asp Ser Pro Trp Thr Asn Ile Ser Gly Ser Cys Lys
    50              55                      60

Gly Arg Cys Phe Glu Leu Gln Glu Ala Gly Pro Pro
            65              70

Asp Cys Arg Cys Asp Asn Leu Cys Lys Ser Tyr Thr
        75              80

Ser Cys Cys His Asp Phe Asp Glu Leu Cys Leu Lys
85              90                      95

Thr Ala Arg Gly Trp Glu Cys Thr Lys Asp Arg Cys
            100             105

Gly Glu Val Arg Asn Glu Glu Asn Ala Cys His Cys
        110             115                 120

Ser Glu Asp Cys Leu Ala Arg Gly Asp Cys Cys Thr
            125             130

Asn Tyr Gln Val Val Cys Lys Gly Glu Ser His Trp
        135             140

Val Asp Asp Asp Cys Glu Glu Ile Lys Ala Ala Glu
145             150                 155

Cys Pro Ala Gly Phe Val Arg Pro Pro Leu Ile Ile
            160             165

Phe Ser Val Asp Gly Phe Arg Ala Ser Tyr Met Lys
    170             175                     180

Lys Gly Ser Lys Val Met Pro Asn Ile Glu Lys Leu
            185             190

Arg Ser Cys Gly Thr His Ser Pro Tyr Met Arg Pro
        195             200

Val Tyr Pro Thr Lys Thr Phe Pro Asn Leu Tyr Thr
205             210                 215

Leu Ala Thr Gly Leu Tyr Pro Glu Ser His Gly Ile
            220             225

Val Gly Asn Ser Met Tyr Asp Pro Val Phe Asp Ala
    230             235                     240

Thr Phe His Leu Arg Gly Arg Glu Lys Phe Asn His
            245             250

Arg Trp Trp Gly Gly Gln Pro Leu Trp Ile Thr Ala
            255             260

Thr Lys Gln Gly Val Lys Ala Gly Thr Phe Phe Trp
265             270                 275

Ser Val Val Ile Pro His Glu Arg Arg Ile Leu Thr
            280             285

Ile Leu Arg Trp Leu Thr Leu Pro Asp His Glu Arg
    290             295                     300

Pro Ser Val Tyr Ala Phe Tyr Ser Glu Gln Pro Asp
            305             310

Phe Ser Gly His Lys Tyr Gly Pro Phe Gly Pro Glu
        315             320

Glu Ser Ser Tyr Gly Ser Pro Phe Thr Pro Ala Lys
325             330                 335

Arg Pro Lys Arg Lys Val Ala Pro Lys Arg Arg Gln
            340             345
```

```
Glu Arg Pro Val Ala Pro Lys Lys Arg Arg
350             355             360

Lys Ile His Arg Met Asp His Tyr Ala Ala Glu Thr
            365             370

Arg Gln Asp Lys Met Thr Asn Pro Leu Arg Glu Ile
        375             380

Asp Lys Ile Val Gly Gln Leu Met Asp Gly Leu Lys
385             390             395

Gln Leu Lys Leu Arg Arg Cys Val Asn Val Ile Phe
            400             405

Val Gly Asp His Gly Met Glu Asp Val Thr Cys Asp
        410             415             420

Arg Thr Glu Phe Leu Ser Asn Tyr Leu Thr Asn Val
            425             430

Asp Asp Ile Thr Leu Val Pro Gly Thr Leu Gly Arg
            435             440

Ile Arg Ser Lys Phe Ser Asn Ala Lys Tyr Asp
445             450             455

Pro Lys Ala Ile Ile Ala Asn Leu Thr Cys Lys Lys
            460             465

Pro Asp Gln His Phe Lys Pro Tyr Leu Lys Gln His
        470             475             480

Leu Pro Lys Arg Leu His Tyr Ala Asn Asn Arg Arg
            485             490

Ile Glu Asp Ile His Leu Leu Val Glu Arg Arg Trp
            495             500

His Val Ala Arg Lys Pro Leu Asp Val Tyr Lys Lys
505             510             515

Pro Ser Gly Lys Cys Phe Phe Gln Gly Asp His Gly
            520             525

Phe Asp Asn Lys Val Asn Ser Met Gln Thr Val Phe
        530             535             540

Val Gly Tyr Gly Pro Thr Phe Lys Tyr Lys Thr Lys
            545             550

Val Pro Pro Phe Glu Asn Ile Glu Leu Tyr Asn Val
            555             560

Met Cys Asp Leu Leu Gly Leu Lys Pro Ala Pro Asn
565             570             575

Asn Gly Thr His Gly Ser Leu Asn His Leu Leu Arg
            580             585

Thr Asn Thr Phe Arg Pro Thr Met Pro Glu Glu Val
        590             595             600

Thr Arg Pro Asn Tyr Pro Gly Ile Met Tyr Leu Gln
                605             610

Ser Asp Phe Asp Leu Gly Cys Thr Cys Asp Asp Lys
            615             620

Val Glu Pro Lys Asn Lys Leu Asp Glu Leu Asn Lys
625             630             635

Arg Leu His Thr Lys Gly Ser Thr Glu Glu Arg His
            640             645

Leu Leu Tyr Gly Arg Pro Ala Val Leu Tyr Arg Thr
650             655             660

Arg Tyr Asp Ile Leu Tyr His Thr Asp Phe Glu Ser
```

```
                        665                     670
Gly Tyr Ser Glu Ile Phe Leu Met Leu Leu Trp Thr
        675                 680

Ser Tyr Thr Val Ser Lys Gln Ala Glu Val Ser Ser
685                 690                 695

Val Pro Asp His Leu Thr Ser Cys Val Arg Pro Asp
            700                 705

Val Arg Val Ser Pro Ser Phe Ser Gln Asn Cys Leu
        710             715                 720

Ala Tyr Lys Asn Asp Lys Gln Met Ser Tyr Gly Phe
            725                 730

Leu Phe Pro Pro Tyr Leu Ser Ser Ser Pro Glu Ala
        735                 740

Lys Tyr Asp Ala Phe Leu Val Thr Asn Met Val Pro
745                 750                 755

Met Tyr Pro Ala Phe Lys Arg Val Trp Asn Tyr Phe
            760                 765

Gln Arg Val Leu Val Lys Lys Tyr Ala Ser Glu Arg
        770             775                 780

Asn Gly Val Asn Val Ile Ser Gly Pro Ile Phe Asp
            785                 790

Tyr Asp Tyr Asp Gly Leu His Asp Thr Glu Asp Lys
        795                 800

Ile Lys Gln Tyr Val Glu Gly Ser Ser Ile Pro Val
805                 810                 815

Pro Thr His Tyr Tyr Ser Ile Ile Thr Ser Cys Leu
            820                 825

Asp Phe Thr Gln Pro Ala Asp Lys Cys Asp Gly Pro
        830             835                 840

Leu Ser Val Ser Ser Phe Ile Leu Pro His Arg Pro
                845             850

Asp Asn Glu Glu Ser Cys Asn Ser Ser Glu Asp Glu
            855                 860

Ser Lys Trp Val Glu Glu Leu Met Lys Met His Thr
865                 870                 875

Ala Arg Val Arg Asp Ile Glu His Leu Thr Ser Leu
            880                 885

Asp Phe Phe Arg Lys Thr Ser Arg Ser Tyr Pro Glu
        890             895                 900

Ile Leu Thr Leu Lys Thr Tyr Leu His Thr Tyr
                905             910

Glu Ser Glu Ile
        916
```